(12) United States Patent
Inberg et al.

(10) Patent No.: US 11,666,056 B2
(45) Date of Patent: Jun. 6, 2023

(54) METHODS AND COMPOSITIONS FOR CONTROL OF ARTHROPOD PESTS

(71) Applicant: GREENLIGHT BIOSCIENCES, INC., Medford, MA (US)

(72) Inventors: Alex Inberg, Chesterfield, MO (US); James Masucci, Manchester, MO (US)

(73) Assignee: GREENLIGHT BIOSCIENCES, INC., Lexington, MA (US)

( * ) Notice: Subject to any disclaimer, the term of this patent is extended or adjusted under 35 U.S.C. 154(b) by 0 days.

(21) Appl. No.: 17/013,330

(22) Filed: Sep. 4, 2020

(65) Prior Publication Data
US 2021/0068402 A1 Mar. 11, 2021

Related U.S. Application Data

(60) Provisional application No. 62/896,289, filed on Sep. 5, 2019.

(51) Int. Cl.
| | | |
|---|---|---|
| *C07H 21/02* | (2006.01) | |
| *C07H 21/04* | (2006.01) | |
| *A01N 63/60* | (2020.01) | |
| *A61K 31/713* | (2006.01) | |
| *C12N 15/113* | (2010.01) | |

(52) U.S. Cl.
CPC .......... *A01N 63/60* (2020.01); *A61K 31/713* (2013.01); *C12N 15/113* (2013.01); *C12N 2310/11* (2013.01); *C12N 2310/14* (2013.01); *C12N 2320/30* (2013.01)

(58) Field of Classification Search
CPC .............. C12N 15/113; C12N 2310/11; C12N 2310/14
See application file for complete search history.

(56) References Cited

U.S. PATENT DOCUMENTS

| | | | |
|---|---|---|---|
| 8,097,712 B2 | 1/2012 | Paldi et al. | |
| 8,507,457 B2 | 8/2013 | Paldi et al. | |
| 8,822,426 B2 | 9/2014 | Paldi et al. | |
| 8,968,584 B2 | 3/2015 | Yamamuro et al. | |
| 9,540,642 B2 | 1/2017 | Inberg et al. | |
| 9,662,348 B2 | 5/2017 | Sela et al. | |
| 9,932,579 B2 | 4/2018 | Paldi et al. | |
| 10,100,306 B2 | 10/2018 | Inberg et al. | |
| 10,557,138 B2 | 2/2020 | Gleit-Kielmanowicz | |
| 10,801,028 B2 | 10/2020 | Sela et al. | |
| 10,888,579 B2 | 1/2021 | Paldi et al. | |
| 10,907,152 B2 | 2/2021 | Inberg et al. | |
| 10,927,374 B2 | 2/2021 | Inberg et al. | |
| 10,980,238 B2* | 4/2021 | Hannus ................. A01N 37/36 | |
| 2012/0157512 A1* | 6/2012 | Ben-Chanoch ......... A61P 31/10 514/44 A |
| 2019/0015528 A1* | 1/2019 | Moran ................. A61K 9/0053 |

FOREIGN PATENT DOCUMENTS

WO  2011045796 A1  4/2011

OTHER PUBLICATIONS

Elbashir et al. (The EMBO Journal, vol. 20, No. 23, pp. 6877-6888, 2001).*
Campbell et al. (Parasites & Vectors, 2010, 3, 73, 1-10).*
Wang, Ruiwu et al. Molecular characterization of an arachnid sodium channel gene from the varroa mite (*Varrao destructor*), Insect Biochemistry and Molecular, 2003, vol. 33, pp. 733-739.
Maori, E. et al., "IAPV, a bee-affecting virus associated with Colony Collapse Disorder can be silenced by dsRNA ingestion", Insect Molecular Biology, 2009, vol. 18, No. 1, pp. 55-60.
Cambell, Ewan M. et al., "Gene-knockdown in the honey bee mite *Varroa destructor* by a non-invasive approach studies on a glutathione S-tranferase", Paraites & Vectors, 2010, vol. 3, No. 73, 10 pages.
Dietemann, Vincent et al., "Varroa destructor: research avenues towards sustainable control", Journal of Apicultural Research, 2010, vol. 51, No. 1, pp. 125-132.
Garbian, Yael et al., "Bidirectional Transfer of RNAi between Honey Bee and Varroa destructor: Varroa Gene Silencing Reduces Varroa Population", PLOS Pathog, 2012, vol. 8, No. 12, 9 pages.
Liu, Zhiqi et al., "Effect of a fluvalinate-resistance-associated sodium channel mutation from varroa mites on cockroach sodium channel sensitivity to fluvalinate, a pyrethroid insecticide", Insect Biochemistry and Molecular Biology, 2006, vol. 36, pp. 885-889.

* cited by examiner

*Primary Examiner* — Amy H Bowman
(74) *Attorney, Agent, or Firm* — Timothy H. Van Dyke; Wolter, Van Dyke, Davis, PLLC

(57) ABSTRACT

The present disclosure also relates to compositions and methods relating to reducing the potency of arthropods using double-stranded RNA and agents to control pests of bees and beehives.

17 Claims, 24 Drawing Sheets
Specification includes a Sequence Listing.

METHODS AND COMPOSITIONS FOR CONTROL OF ARTHROPOD PESTS

CROSS-REFERENCE TO RELATED APPLICATION AND INCORPORATION OF SEQUENCE LISTING

This application claims the benefit of U.S. Provisional Application No. 62/896,289, filed Sep. 5, 2019, which is incorporated by reference in its entirety herein. A sequence listing contained in the file named "P34522US01_SL.TXT" which is 2,311 bytes (measured in MS-Windows®) and created on Sep. 11, 2017 is filed electronically herewith and incorporated by reference in its entirety.

FIELD

The present disclosure also relates to compositions and methods relating to reducing the potency of arthropod pests and vectors.

BACKGROUND

Bee colony losses are influenced by several factors, among which are *Varroa destructor* mites (*Varroa* mites) and bee viruses, which can be transmitted by *Varroa* mites. *Varroa* mites are considered to be the biggest threat to managed bee health and they frequently cause unsustainably high bee colony losses if left unchecked. Several treatment options to prevent or treat *Varroa* mite infestations are available to beekeepers, including synthetic miticides, non-selective organic acids, essential oils, and other products. Synthetic products, including pyrethroid, organophosphate, and amitraz-based solutions provide the first line of treatment. However, many of these products have lost, or are losing, efficacy due to rapidly developing resistance. In addition, many synthetic pesticides used to control *Varroa* mites appear to negatively impact the health of bees.

RNA interference is a promising technology that can be used to control bee viruses and *Varroa* mites. In order to control *Varroa* mites in beehives, dsRNA specifically targeting mite genes is applied to a beehive and eventually delivered to *Varroa*. The active RNA molecules are processed by the *Varroa destructor* intracellular RNAi machinery, resulting in *Varroa* mite mortality and/or disruption of *Varroa* mite physiological processes, which eventually leads to suppression of *Varroa* mite population in hives and improves bee colony survival. However, dsRNAs can be rapidly degraded by the microbiota found in beehives, and methods and compositions useful for stabilizing dsRNAs in beehives are needed.

SUMMARY

Figures 1, 1A:
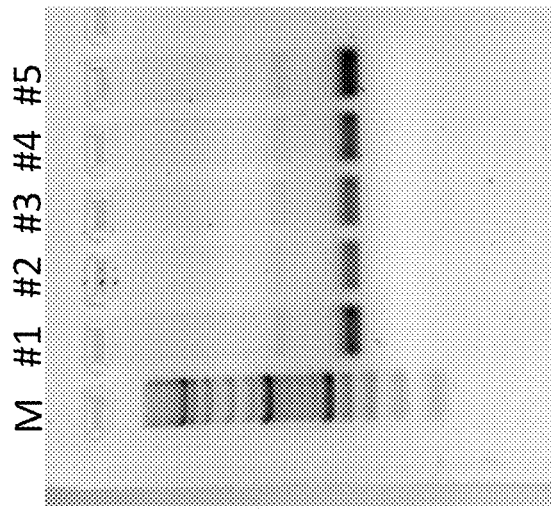
FIG. 1 shows CAM376 electrophoresed on 2% TAE (Tris base, acetic acid, EDTA) agarose gels. The agarose gels depict CAM376 at various time points in the presence of a contaminating microbiota solution and also in the presence or absence of food-grade preservatives and/or citric buffer at various time points. A starting concentration of 0.4 mg/mL was used for CAM376 in each experimental group. In all parts of FIG. 1: M represents the nucleic acid length marker; #1 represents CAM376 in an 80% sucrose solution; #2 represents CAM376 in an 80% sucrose solution with 0.1% (w/v) sodium benzoate and 0.1% (w/v) potassium sorbate; #3 represents CAM376 in an 80% sucrose solution with citric buffer; #4 represents CAM376 in an 80% sucrose solution with 0.1% (w/v) sodium benzoate, 0.1% (w/v) potassium sorbate, and citric buffer; and #5 represents CAM376 in an 80% sucrose solution with 0.1% (w/v) sodium benzoate, 0.05% (w/v) potassium sorbate, and citric buffer.
FIG. 1A depicts CAM376 at Day 0 (prior to the addition of the contaminating microbiota solution).
Figures 1, 1B:
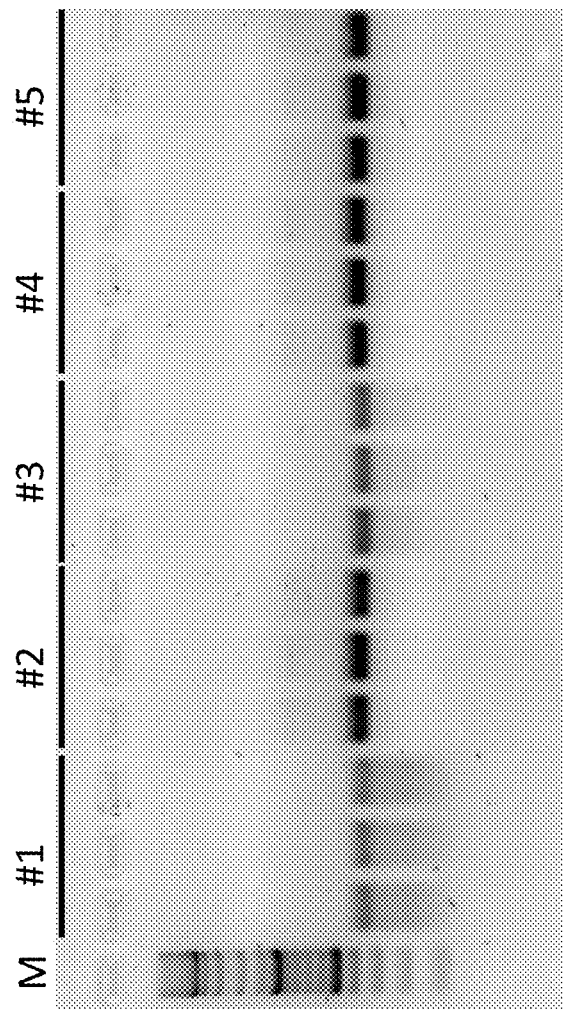
FIG. 1B depicts CAM376 at Day 4.

In one aspect, this disclosure provides a method of treating or preventing an *Varroa destructor* infestation of a beehive or bee colony comprising: (a) providing to the beehive or bee colony a composition comprising a nucleic acid molecule that is complementary or identical to at least 21 contiguous nucleotides of a *Varroa destructor* messenger RNA (mRNA); and (b) providing an agent to control mites to the beehive or bee colony, thereby treating or preventing the *Varroa destructor* infestation of the beehive or bee colony.

In one aspect, this disclosure provides a method of causing mortality or reducing the fecundity of a *Varroa destructor* mite comprising: (a) providing a composition comprising a nucleic acid molecule complementary to a *Varroa destructor* mite messenger RNA (mRNA) to a *Varroa destructor* mite; and (b) providing an agent to control mites to the *Varroa destructor* mite, thereby causing mortality or reducing the fecundity of the *Varroa destructor* mite.

DETAILED DESCRIPTION

Unless defined otherwise herein, terms are to be understood according to conventional usage by those of ordinary skill in the relevant art. Examples of resources describing many of the terms related to molecular biology used herein can be found in Alberts et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007. The nomenclature for DNA bases as set forth at 37 C.F.R. § 1.822 is used.

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if a selection is made from the group consisting of A, B, C, and D, the inventors also specifically envision each alternative individually, as well as combinations such as A, B, and D; A and C; B and C; etc.

Bees and Mites

As used herein, terms in the singular and the singular forms "a," "an," and "the," for example, include plural referents unless the content clearly dictates otherwise. Thus, for example, reference to "bee," "honeybee," or "a bee" also includes a plurality of bees or honeybees.

As used herein, the term "arthropod" refers to an invertebrate animal comprising an exoskeleton, a segmented body, and jointed appendages. Arthropods are members of the Phylum Arthropoda, which includes, without being limiting, Class Arachnida (e.g., spiders, scorpions, mites, etc.), Class Merostomata (e.g., horseshoe crabs), Class Pycnogonida (e.g., sea spiders), Class Chilopoda (e.g., centipedes), Class Diplopoda (e.g., millipedes); Class Maxillopoda (e.g., barnacles, copepods), Class Malacostraca (e.g., shrimp, lobsters, crabs), Class Insecta (e.g., insects), and Class Entognatha (e.g., springtails).

In one aspect, an arthropod provided herein is an arachnid (e.g., Class Arachnida). In another aspect, an arthropod provided herein is in the Subclass Acari (e.g., ticks and mites). In still a further aspect, an arthropod provided herein is in the Order Parasitiformes (e.g., ticks and mites). In an aspect, an arthropod provided herein is in the Suborder Mesostigmata (e.g., free-living, predatory mites). In another aspect, an arthropod provided herein is in the Family Varroidae.

As used herein, the term "mite" refers to any arthropod belonging to the Subclass Acari. Non-limiting examples of mites include *Varroa destructor, Varroa jacobsoni, Varroa rindereri, Varroa sinhai, Varroa underwoodi, Varroa wongsirii, Acarapis woodi* (tracheal mite), *Tropilaelaps clareae, Tropilaelaps koenigerum, Tropilaelaps mercedesae,* and *Tropilaelaps thaii.*

In one aspect, an arthropod provided herein is in the Genus *Tropilaelaps.* In another aspect, an arthropod provided herein is selected from the group consisting of *Tropilaelaps clareae, Tropilaelaps koenigerum, Tropilaelaps mercedesae,* and *Tropilaelaps thaii.* In yet another aspect, an arthropod provided herein is *Acarapis woodi.* In still another aspect, an arthropod provided herein is in the Genus *Varroa.* In yet a further aspect, an arthropod provided herein is *Varroa destructor.* In an aspect, an arthropod provided herein is selected from the group consisting of *Varroa destructor, Varroa jacobsoni, Varroa rindereri, Varroa sinhai, Varroa underwoodi,* and *Varroa wongsirii.*

As used herein, the term "bee" refers to an insect in a family selected from the group consisting of Family Andrenidae, Family Apidae, Family Colletidae, Family Halictidae, Family Megachilidae, Family Melittidae, and Family Stenotritidae. In an aspect, a member of Family Apidae is selected from the group consisting of *Apis* (e.g., honeybees), *Bombus* (e.g., bumblebees), *Osmia* (e.g., mason bees), *Trigona* (e.g., stingless bees), and *Xylocopa* (e.g., carpenter bees).

In one aspect, a bee species is selected from the group consisting of *Apis andreniformis*, *Apis florea*, *Apis dorsata*, *Apis cerana*, *Apis koschevnikovi*, *Apis mellifera*, and *Apis nigrocincta*. In another aspect, a bee species is selected from the group consisting of *Apis cerana* and *Apis mellifera*. In still another aspect, a bee is *Apis mellifera*. In a further aspect, a bee is *Apis cerana*.

The term "bee" refers to all stages of the bee life cycle (e.g., adult bees, larval bees, pupal bees, bee eggs). In one aspect, a bee is an adult bee. In another aspect, a bee is a larval bee. In an aspect a bee is a pupal bee. In another aspect, a bee is a worker bee. As used herein, a "worker bee" refers to a bee that is not a queen bee or a drone bee. For instance, a worker bee can refer to a forager bee or a hive bee. A "drone bee" refers to a male bee that is the product of an unfertilized egg. Without being limiting, the primary role of a drone bee is to mate with a queen bee.

In an aspect, a bee is a forager bee. As used herein, a "forager bee" refers to a bee that leaves a hive or colony to collect and/or scout for water, nectar, pollen, or resin. Typically, forager bees are at least 21 days old. In another aspect a bee is a hive bee. As used herein, a "hive bee" refers to a bee that does not leave the hive to scout for or collect resources. Typically, hive bees are less than 21 days old. Without being limiting, hive bees care for young bees/larvae, feed young bees/larvae, care for the queen bee and/or drones, produce honey, produce royal jelly, produce wax, regulate hive temperature, defend the hive from intruders, and build/repair/clean hive structure (e.g., honeycomb).

In still a further aspect, a bee is a bee of a bee colony. As used herein, a "bee colony" refers to a collection of a queen bee and worker bees. A bee colony can further comprise drone bees. Typically, hive and forager bees of a colony are descendent from the colony's queen, but this is not required of a bee colony. A bee colony can comprise anywhere from 1 to over 100,000 individual bees, although 20,000 to 60,000 bees is most common.

In an aspect a bee is a bee of a beehive. As used herein, a "beehive" refers to an enclosed, often manmade, structure that houses a bee colony. Without being limiting, a beehive typically comprises a queen bee, hive bees, forager bees, and drone bees. In an aspect, a beehive provided herein comprises a composition provided herein. In one aspect, a beehive provided here comprises an *Apis cerana* bee or an *Apis mellifera* bee. In another aspect, a beehive provided herein is infested by at least one mite. In yet another aspect, a beehive provided herein is infested by at least one *Varroa destructor* mite. In still a further aspect, a beehive further comprises a feeder.

The terms "*Varroa destructor* mite" and "*Varroa* mite" are used interchangeably to refer to any life stage of the mite species *Varroa destructor*. *Varroa* mites are external parasites of *Apis cerana* and *Apis mellifera*, although they may parasitize other bee species as well. Adult *Varroa* mites feed on bee hemolymph and/or brood food in brood cells. Female *Varroa* mites deposit eggs on larval bees after the brood cell is capped, and the *Varroa* mite eggs hatch and feed on the developing larval bee.

Bee/Mite Feeding Compositions

Bee feeding is common practice amongst bee-keepers, for providing both nutritional and other, for example, supplemental needs. Bees typically feed on honey and pollen, but are known to ingest non-natural feeds as well. Bees can be fed various compositions including, but not limited to Wheast (a dairy yeast grown on cottage cheese), soybean flour, yeast (e.g. brewer's yeast, torula yeast) and yeast products products-fed singly or in combination and soybean flour fed as a dry mix or moist cake inside the hive or as a dry mix in open feeders outside the hive. Also useful is sugar, or sugar syrup. The addition of 10 to 12 percent pollen to a composition to bees improves palatability. The addition of 25 to 30 percent pollen improves the quality and quantity of essential nutrients that are required by bees for vital activity.

Cane or beet sugar, isomerized corn syrup, and type-50 sugar syrup are satisfactory substitutes for honey in the natural diet of honey bees. Isomerized corn syrup, and type-50 sugar syrup can be supplied only as a liquid to bees.

Feeders are often used to provide food and/or supplements to bee colonies. Non-limiting examples of feeders include open feeders, friction-top pails, combs within brood chambers of a beehive, division board feeders, boardman feeders, and pans or trays. In one aspect, a feeder comprises a composition provided herein. In an aspect, a feeder provided herein is selected from the group consisting of an open feeder, a friction-top pail, a comb within a brood chamber of a beehive, a division board feeder, a boardman feeder, a pan, and a tray.

Liquid feed can be supplied to bees inside the hive by, for example, any of the following methods: friction-top pail, combs within the brood chamber, division board feeder, boardman feeder, etc. Dry sugar may be fed by placing it on the inverted inner cover. A supply of water must be available to bees at all times. In one embodiment, pan or trays in which floating supports-such as wood chips, cork, or plastic sponge—are present are envisaged. Detailed descriptions of supplemental feeds for bees can be found in, for example, USDA publication by Standifer et al., 1977, "Supplemental Feeding of Honey Bee Colonies," USDA Agriculture Information Bulletin No. 413.

In one aspect, a composition provided herein is a liquid. In another aspect, a composition provided herein is a solid.

Arthropods, including bees and *Varroa* mites, are capable of ingesting and/or absorbing the compositions provided herein. In one aspect, a composition provided herein is ingestible by an arthropod. In another aspect, a composition provided herein is ingestible by a bee. In another aspect, a composition provided herein is ingestible by a bee selected from the group consisting of *Apis cerana* and *Apis mellifera*. In a further aspect, a composition provided herein is ingestible by a mite. In another aspect, a composition provided herein is ingestible by a *Varroa destructor* mite. In one aspect, a composition provided herein is absorbable by an arthropod. In another aspect, a composition provided herein is absorbable by a bee. In another aspect, a composition provided herein is absorbable by a bee selected from the group consisting of *Apis cerana* and *Apis mellifera*. In a further aspect, a composition provided herein is absorbable by a mite. In another aspect, a composition provided herein is absorbable by a *Varroa destructor* mite.

It was discovered by the inventors of the present application that dsRNAs provided to beehives rapidly degrade in the presence of beehive microbiota communities. Compositions to improve stability of a nucleic acid molecule are provided herein. In another aspect, a composition provided herein comprises at least one carbohydrate, at least one food-grade preservative, and a nucleic acid molecule. In an aspect, a composition provided herein comprises at least one carbohydrate, at least one food-grade preservative, and a nucleic acid molecule. In an aspect, a composition provided herein comprises at least one oligosaccharide, at least one food-grade preservative, and a nucleic acid molecule. In an aspect, a composition provided herein comprises at least one monosaccharide, at least one food-grade preservative, and a nucleic acid molecule. In an aspect, a composition provided herein comprises at least one disaccharide, at least one food-grade preservative, and a nucleic acid molecule. In an aspect, a composition provided herein comprises at least one polyol, at least one food-grade preservative, and a nucleic acid molecule.

In another aspect, a composition provided herein comprises at least one carbohydrate, at least two food-grade preservatives, and a nucleic acid molecule. In an aspect, a composition provided herein comprises at least one carbohydrate, at least two food-grade preservatives, and a nucleic acid molecule. In an aspect, a composition provided herein comprises at least one oligosaccharide, at least two food-grade preservatives, and a nucleic acid molecule. In an aspect, a composition provided herein comprises at least one monosaccharide, at least two food-grade preservatives, and a nucleic acid molecule. In an aspect, a composition provided herein comprises at least one disaccharide, at least two food-grade preservatives, and a nucleic acid molecule. In an aspect, a composition provided herein comprises at least one polyol, at least two food-grade preservatives, and a nucleic acid molecule.

In an aspect, this disclosure provides a method comprising administering a composition comprising at least one carbohydrate, at least one food-grade preservative, and a nucleic acid molecule to a bee or a *Varroa destructor* mite. In an aspect, this disclosure provides a method comprising administering a composition comprising at least one carbohydrate, at least one food-grade preservative, and a nucleic acid molecule to a bee or a *Varroa destructor* mite. In an aspect, this disclosure provides a method comprising administering a composition comprising at least one oligosaccharide, at least one food-grade preservative, and a nucleic acid molecule to a bee or a *Varroa destructor* mite. In an aspect, this disclosure provides a method comprising administering a composition comprising at least one monosaccharide, at least one food-grade preservative, and a nucleic acid molecule to a bee or a *Varroa destructor* mite. In an aspect, this disclosure provides a method comprising administering a composition comprising at least one disaccharide, at least one food-grade preservative, and a nucleic acid molecule to a bee or a *Varroa destructor* mite. In an aspect, this disclosure provides a method comprising administering a composition comprising at least one polyol, at least one food-grade preservative, and a nucleic acid molecule to a bee or a *Varroa destructor* mite.

As used herein, the term "administering" refers to any method of providing a composition to an arthropod, bee, mite, or *Varroa* mite. Non-limiting examples of administering a composition provided herein include feeding the composition to an organism; spraying the composition on an organism, beehive, or feeder; and topically applying the composition to a beehive, feeder, or an organism. In an aspect, administration of a composition provided herein is selected from the group consisting of feeding, spraying, and topical application. In an aspect, administration of a composition provided herein is through providing in a feeder.

In an aspect, a composition provided herein is bee-ingestible. In another aspect, a composition provided herein is mite-ingestible. In another aspect, a composition provided herein is arthropod-ingestible. In still another aspect, a composition provided herein is *Varroa destructor*-ingestible. In an aspect, a composition provided herein is bee-absorbable. In another aspect, a composition provided herein is mite-absorbable. In another aspect, a composition provided herein is arthropod-absorbable. In still another aspect, a composition provided herein is *Varroa destructor*-absorbable.

Carbohydrates are organic molecules consisting of carbon, hydrogen, and oxygen atoms. Carbohydrates are often soluble in aqueous solutions. In an aspect, a composition provided herein comprises a carbohydrate. In one aspect, a carbohydrate provided herein is selected from the group consisting of a polysaccharide, an oligosaccharide, a disaccharide, a monosaccharide, a polyol, and any combination thereof.

Monosaccharides are the simplest carbohydrates and they cannot be hydrolyzed into smaller carbohydrates. Non-limiting examples of monosaccharides include glucose, galactose, fructose, and xylose. Disaccharides comprise two joined monosaccharides. Non-limiting examples of disaccharides include sucrose, lactose, maltose, and trehalose. Polyols, or sugar alcohols, comprise multiple hydroxyl groups. Non-limiting examples of polyols include sorbitol, inositol, and mannitol. An oligosaccharide is a polymer comprising, typically, two to ten monosaccharides. Non-limiting examples of oligosaccharides include maltodextrins, raffinose, stachyose, and fructo-oligosaccharides. Polysaccharides comprise long chains of monosaccharides bound by glycosidic linkages. Non-limiting examples of polysaccharides include amylose, amylopectin, cellulose, hemicellulose, pectins, and hydrocolloids.

In an aspect a carbohydrate provided herein is a monosaccharide. In another aspect, a carbohydrate provided herein is a disaccharide. In still another aspect, a carbohydrate provided herein is a polyol. In one aspect, a carbohydrate provided herein is selected from the group consisting of arabinose, dextrose, fructose, fucose, galactose, glucose, inositol, lactose, maltose, mannitol, mannose, rhamnose, ribose, sorbitol, sucrose, trehalose, xylose, and any combination thereof. In another aspect, a carbohydrate provided herein is selected from the group consisting of high fructose corn syrup, high maltose corn syrup, sugar syrup, inverted sugar syrup, and any combination thereof. In another aspect, a carbohydrate provided herein is glucose. In another aspect, a carbohydrate provided herein is fructose. In another aspect, a carbohydrate provided herein is sucrose. In another aspect, a carbohydrate provided herein is high fructose corn syrup. In another aspect, a carbohydrate provided herein is inverted sugar syrup. In another aspect, a carbohydrate provided herein is cane sugar. In another aspect, a carbohydrate provided herein is beet sugar. In another aspect, a carbohydrate provided herein is isomerized corn syrup. In another aspect, a carbohydrate provided herein is type-50 sugar syrup.

In one aspect, a composition provided herein comprises at least 10%, at least 20%, at least 30%, at least 40%, at least 50%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89% at least 90%, at least 91%, at least 92%, at least 93%, at least 94%, at least 95%, at least 96%, at least 97%, at least 98%, or at least 99% carbohydrate by weight. In one aspect, a composition provided herein comprises at least 80% carbohydrate by weight. In another aspect, a composition provided herein comprises at least 85% carbohydrate by weight. In one aspect, a composition provided herein comprises at least 10%, at least 20%, at least 30%, at least 40%, at least 50%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 8'7%, at least 88%, at least 89% at least 90%, at least 91%, at least 92%, at least 93%, at least 94%, at least 95%, at least 96%, at least 97%, at least 98%, or at least 99% carbohydrate by volume.

In another aspect, a composition provided herein comprises between 25% and 95%, between 25% and 90%, between 25% and 85%, between 25% and 80%, between 25% and 75%, between 25% and 70%, between 25% and 65%, between 25% and 60%, between 25% and 55%, between 25% and 50% carbohydrate by weight. In still another aspect, a composition provided herein comprises between 50% and 95%, between 50% and 90%, between 50% and 85%, between 50% and 80%, between 50% and 75%, between 50% and 65%, or between 50% and 60% carbohydrate by weight. In a further aspect, a composition provided herein comprises between 60% and 90%, between 60% and 85%, between 60% and 80%, between 60% and 75%, or between 60% and 70% carbohydrate by weight. In another aspect a composition provided herein comprises between 70% and 90%, between 70% and 89%, between 70% and 88%, between 70% and 87%, between 70% and 86%, between 70% and 85%, between 70% and 84%, between 70% and 83%, between 70% and 82%, between 70% and 81%, or between 70% and 80% carbohydrate by weight. In an aspect a composition provided herein comprises between 71% and 90%, between 72% and 90%, between 73% and 90%, between 74% and 90%, between 75% and 90%, between 76% and 90%, between 77% and 90%, between 78% and 90%, between 79% and 90%, between 80% and 90%, between 81% and 90%, between 82% and 90%, between 83% and 90%, between 84% and 90%, between 85% and 90%, between 86% and 90%, between 87% and 90%, between 88% and 90%, between 89% and 90%, between 79% and 86%, or between 80% and 85% carbohydrate by weight.

In another aspect, a composition provided herein comprises between 25% and 95%, between 25% and 90%, between 25% and 85%, between 25% and 80%, between 25% and 75%, between 25% and 70%, between 25% and 65%, between 25% and 60%, between 25% and 55%, between 25% and 50% carbohydrate by volume. In still another aspect, a composition provided herein comprises between 50% and 95%, between 50% and 90%, between 50% and 85%, between 50% and 80%, between 50% and 75%, between 50% and 65%, or between 50% and 60% carbohydrate by volume. In a further aspect, a composition provided herein comprises between 60% and 90%, between 60% and 85%, between 60% and 80%, between 60% and 75%, or between 60% and 70% carbohydrate by volume. In another aspect a composition provided herein comprises between 70% and 90%, between 70% and 89%, between 70% and 88%, between 70% and 87%, between 70% and 86%, between 70% and 85%, between 70% and 84%, between 70% and 83%, between 70% and 82%, between 70% and 81%, or between 70% and 80% carbohydrate by volume. In an aspect a composition provided herein comprises between 71% and 90%, between 72% and 90%, between 73% and 90%, between 74% and 90%, between 75% and 90%, between 76% and 90%, between 77% and 90%, between 78% and 90%, between 79% and 90%, between 80% and 90%, between 81% and 90%, between 82% and 90%, between 83% and 90%, between 84% and 90%, between 85% and 90%, between 86% and 90%, between 87% and 90%, between 88% and 90%, between 89% and 90%, between 79% and 86%, or between 80% and 85% carbohydrate by volume.

Preservatives

Without being bound by any theory, the addition of a food-grade preservative to a composition comprising a nucleic acid molecule can extend the lifespan of the nucleic acid molecule in the composition. Nucleic acid molecules can be rapidly degraded in the presence of microorganisms such as bacteria, protozoans, and fungi. For example, a nucleic acid molecule may survive up to three days in a composition without a food-grade preservative, but the addition of a food-grade preservative to the composition can extend the life span of the nucleic acid several fold under the same conditions.

As used herein, "detectable" refers to being able to identify the presence of one or more nucleic acid molecules in a composition using standard methods in the art. Numerous methods suitable for detecting the presence of a nucleic acid molecule are known in the art. Without being limiting, such methods include agarose gel electrophoresis, DNA sequencing, RNA sequencing, Southern blot hybridization, Northern blot hybridization, liquid chromatography, ultra-pure liquid chromatography, high performance liquid chromatography, optical density using a spectrophotometer (e.g., NanoDrop™), and fluorometric quantitation (e.g., Qubit™). If relevant methods known to those of ordinary skill in the art fail to detect a nucleic acid molecule provided herein, those in the art would recognize that the nucleic acid molecule is not present at a detectable level.

In one aspect, a nucleic acid molecule is detectable in a composition provided herein for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, at least 50, at least 55, at least 60 days, at least 65 days, at least 70 days, at least 75 days, at least 80 days, at least 85 days, at least 90 days, at least 95 days, or at least 100 days. In another aspect, a nucleic acid molecule is detectable in a composition provided herein for between 1 and 100 days, between 1 and 90 days, between 1 and 80 days, between 1 and 70 days, between 1 and 60 days, between 1 and 50 days, between 1 and 40 days, between 1 and 30 days, between 1 and 20 days, or between 1 and 10 days. In another aspect, a nucleic acid molecule is detectable in a composition provided herein for between 5 and 100 days, between 5 and 90 days, between 5 and 80 days, between 5 and 70 days, between 5 and 60 days, between 5 and 50 days, between 5 and 40 days, between 5 and 30 days, between 5 and 20 days, or between 5 and 10 days. In another aspect, a nucleic acid molecule is present in a composition provided herein for between 10 and 100 days, between 10 and 90 days, between 10 and 80 days, between 10 and 70 days, between 10 and 60 days, between 10 and 50 days, between 10 and 40 days, between 10 and 30 days, or between 10 and 20 days.

In an aspect, a composition comprising a nucleic acid molecule provided herein comprises 100% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 100% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 100% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 95% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 95% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 95% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 90% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 90% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 90% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 85% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 85% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 85% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 80% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 80% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 80% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 75% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 75% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 75% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 70% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 70% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 70% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 65% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 65% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 65% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 60% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 60% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 60% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 55% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 55% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 55% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 50% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 50% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 50% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 45% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, or 60 days. In an aspect, a beehive comprising a nucleic acid provided herein comprises 45% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 45% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 40% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 40% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 40% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 35% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 35% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 35% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 30% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 30% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 30% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 25% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 25% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 25% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 20% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 20% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 20% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 15% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 15% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 15% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 10% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 10% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 10% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

In an aspect, a composition comprising a nucleic acid molecule provided herein comprises at least 5% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In an aspect, a beehive comprising a nucleic acid provided herein comprises 5% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days. In another aspect, a feeder comprising a nucleic acid provided herein comprises 5% of the original concentration of the nucleic acid molecule after 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days.

As used herein, a "food-grade preservative" refers to any substance that can be added to a composition to prevent or slow decomposition by microorganisms and/or prevent or slow chemical changes of the composition. In an aspect, a composition provided herein comprises a food-grade preservative. Non-limiting examples of food-grade preservatives include: 2,2-dibromo-3-nitrilopropionamide, 4-hexylresorcinol, acetic acid, ascorbic acid, ascorbyl palmitate, ascorbyl stearate, benzoic acid, butylated hydroxyanisole, butylated hydroxytoluene (3,5-ditertiarybutyl-4-hydroxytoluene), calcium ascorbate, calcium propionate, calcium sorbate, caprylic acid, citric acid, citric acid esters of diglycerides, citric acid esters of monoglycerides, dehydroacetic acid, dimethyl dicarbonate, disodium ethylenebisdithiocarbamate, erythorbic acid, ethyl lauroyl arginate, gum guaiacum, formic acid, isoascorbic acid, L-cysteine, L-cysteine hydrochloride, lactic acid, lecithin, lecithin citrate, methyl paraben, methyl-p-hydroxy benzoate, monoglyceride citrate, monoisopropyl citrate, n-heptyl p-hydroxybenzoate, natamycin, octyl gallate, potassium acetate, potassium benzoate, potassium bisulfite, potassium diacetate, potassium lactate, potassium metabisulfite, potassium nitrate, potassium nitrite, potassium sorbate, propionic acid, propyl gallate, propyl paraben, propyl-p-hydroxy benzoate, sodium acetate, sodium ascorbate, sodium benzoate, sodium bisulfite, sodium diacetate, sodium dimethyldithiocarbamate, sodium dithionite, sodium erythorbate, sodium isoascorbate, sodium lactate, sodium metabisulfite, sodium nitrate, sodium nitrite, sodium phosphate (monobasic), sodium propionate, sodium salt of methyl-p-hydroxy benzoic acid, sodium salt of propyl-p-hydroxy benzoic acid, sodium sorbate, sodium sulfite, sorbic acid, stannous chloride, stearyl citrate, sulfurous acid, sulfur dioxide, tartaric acid, tertiary butyl hydroquinone, and tocopherols.

In an aspect, a food-grade preservative used herein is citric acid. In one aspect, a food-grade preservative used herein is potassium sorbate. In another aspect, a food-grade preservative used herein is sodium benzoate. In still another aspect, a food-grade preservative used herein is selected from the group consisting of potassium sorbate and sodium benzoate.

In an aspect, a food-grade preservative provided herein is selected from the group consisting of: 2,2-dibromo-3-nitrilopropionamide, 4-hexylresorcinol, acetic acid, ascorbic acid, ascorbyl palmitate, ascorbyl stearate, benzoic acid, butylated hydroxyanisole, butylated hydroxytoluene (3,5-ditertiarybutyl-4-hydroxytoluene), calcium ascorbate, calcium propionate, calcium sorbate, caprylic acid, citric acid, citric acid esters of diglycerides, citric acid esters of monoglycerides, dehydroacetic acid, dimethyl dicarbonate, disodium ethylenebisdithiocarbamate, erythorbic acid, ethyl lauroyl arginate, gum guaiacum, formic acid, isoascorbic acid, L-cysteine, L-cysteine hydrochloride, lactic acid, lecithin, lecithin citrate, methyl paraben, methyl-p-hydroxy benzoate, monoglyceride citrate, monoisopropyl citrate, n-heptyl p-hydroxybenzoate, natamycin, octyl gallate, potassium acetate, potassium benzoate, potassium bisulfite, potassium diacetate, potassium lactate, potassium metabisulfite, potassium nitrate, potassium nitrite, potassium sorbate, propionic acid, propyl gallate, propyl paraben, propyl-p-hydroxy benzoate, sodium acetate, sodium ascorbate, sodium benzoate, sodium bisulfite, sodium diacetate, sodium dimethyldithiocarbamate, sodium dithionite, sodium erythorbate, sodium isoascorbate, sodium lactate, sodium metabisulfite, sodium nitrate, sodium nitrite, sodium phosphate (monobasic), sodium propionate, sodium salt of methyl-p-hydroxy benzoic acid, sodium salt of propyl-p-hydroxy benzoic acid, sodium sorbate, sodium sulfite, sorbic acid, stannous chloride, stearyl citrate, sulfurous acid, sulfur dioxide, tartaric acid, tertiary butyl hydroquinone, and tocopherols.

In an aspect, a composition provided herein comprises at least one food-grade preservative. In another aspect, a composition provided herein comprises at least two food-grade preservatives. In another aspect, a composition provided herein comprises at least three food-grade preservatives. In another aspect, a composition provided herein comprises at least four, at least five, at least six, at least seven, at least eight, at least nine, or at least ten food-grade preservatives. In one aspect, a composition provided herein comprises at least two food-grade preservatives, where the at least two food-grade preservatives are sodium benzoate and potassium sorbate.

In an aspect, a composition provided herein comprises a total food-grade preservative concentration of 0.2% by weight. As used herein, a "total food-grade preservative" measurement sums the amount of each different type of food-grade preservative used in a composition. In another aspect, a composition provided herein comprises a total food-grade preservative concentration of between 0.01% and 5%, between 0.01% and 4%, between 0.01% and 3%, between 0.01% and 2%, between 0.01% and 1%, between 0.01% and 0.9%, between 0.01% and 0.8%, between 0.01% and 0.7%, between 0.01% and 0.6%, between 0.01% and 0.5%, between 0.01% and 0.4%, between 0.01% and 0.3%, between 0.01% and 0.2%, or between 0.01% and 0.1% by weight. In still another aspect, a composition provided herein comprises a total food-grade preservative concentration of up to and including 5%, up to and including 4%, up to and including 3%, up to and including 2%, up to and including 1%, up to and including 0.9%, up to and including 0.8%, up to and including 0.7%, up to and including 0.6%, up to and including 0.5%, up to and including 0.4%, up to and including 0.3%, up to and including 0.2%, up to and including 0.1%, or up to and including 0.05% by weight. In one aspect, a composition provided herein comprises a food-grade preservative at a concentration of up to and including 0.3%, up to and including 0.2%, up to and including 0.15%, up to and including 0.1%, up to and including 0.09%, up to and including 0.08%, up to and including 0.07%, up to and including 0.06%, up to and including 0.05%, up to and including 0.04%, up to and including 0.03%, up to and including 0.02%, up to and including 0.01%, or up to and including 0.001% of the composition by weight.

In an aspect, a composition provided herein comprises sodium benzoate at a concentration of 0.2% by weight. In an aspect, a composition provided herein comprises sodium benzoate at a concentration of 0.1% by weight. In one aspect, a composition provided herein comprises sodium benzoate at a concentration of 0.05% by weight. In another aspect, a composition provided herein comprises sodium benzoate at a concentration between 0.01% and 0.2%, between 0.02% and 0.2%, between 0.05% and 0.2%, between 0.1% and 0.2%, between 0.01% and 0.1%, between 0.02% and 0.1%, between 0.03% and 0.1%, between 0.04% and 0.1%, between 0.05% and 0.1%, between 0.06% and 0.1%, between 0.07% and 0.1%, between 0.08% and 0.1%, between 0.09% and 0.1%, between 0.001% and 0.1%, between 0.005% and 0.1%, between 0.001% and 0.5%, or between 0.005% and 0.5% by weight. In still another aspect, a composition provided herein comprises sodium benzoate at a concentration of up to and including 0.2%, up to and including 0.15%, up to and including 0.1%, up to and including 0.09%, up to and including 0.08%, up to and including 0.07%, up to and including 0.06%, up to and including 0.05%, up to and including 0.04%, up to and including 0.03%, up to and including 0.02%, or up to and including 0.01% by weight.

In an aspect, a composition provided herein comprises potassium sorbate at a concentration of 0.2% by weight. In an aspect, a composition provided herein comprises potassium sorbate at a concentration of 0.1% by weight. In an aspect, a composition provided herein comprises potassium sorbate at a concentration of 0.05% by weight. In another aspect, a composition provided herein comprises potassium sorbate at a concentration between 0.01% and 0.2%, between 0.02% and 0.2%, between 0.05% and 0.2%, between 0.1% and 0.2%, between 0.01% and 0.1%, between 0.02% and 0.1%, between 0.03% and 0.1%, between 0.04% and 0.1%, between 0.05% and 0.1%, between 0.06% and 0.1%, between 0.07% and 0.1%, between 0.08% and 0.1%, between 0.09% and 0.1%, between 0.001% and 0.1%, between 0.005% and 0.1%, between 0.001% and 0.5%, or between 0.005% and 0.5% by weight. In still another aspect, a composition provided herein comprises potassium sorbate at a concentration of up to and including 0.2%, up to and including 0.15%, up to and including 0.1%, up to and including 0.09%, up to and including 0.08%, up to and including 0.07%, up to and including 0.06%, up to and including 0.05%, up to and including 0.04%, up to and including 0.03%, up to and including 0.02%, or up to and including 0.01% by weight.

In an aspect, a composition provided herein comprises a food-grade preservative at a concentration of 1% by weight. In an aspect, a composition provided herein comprises a food-grade preservative at a concentration of 0.5% by weight. In an aspect, a composition provided herein comprises a food-grade preservative at a concentration of 0.4% by weight. In an aspect, a composition provided herein comprises a food-grade preservative at a concentration of 0.3% by weight. In an aspect, a composition provided herein comprises a food-grade preservative at a concentration of 0.2% by weight. In an aspect, a composition provided herein comprises a food-grade preservative at a concentration of 0.1% by weight. In one aspect, a composition provided herein comprises a food-grade preservative at a concentration of 0.05% by weight. In one aspect, a composition provided herein comprises a food-grade preservative at a concentration of 0.01% by weight. In one aspect, a composition provided herein comprises a food-grade preservative at a concentration of 0.001% by weight. In one aspect, a composition provided herein comprises a food-grade preservative at a concentration of 0.0001% by weight. In another aspect, a composition provided herein comprises sodium benzoate at a concentration between 0.001% and 0.1%, between 0.002% and 0.1%, between 0.003% and 0.1%, between 0.004% and 0.1%, between 0.005% and 0.1%, between 0.006% and 0.1%, between 0.007% and 0.1%, between 0.008% and 0.1%, between 0.009% and 0.1%, between 0.0001% and 0.1%, between 0.0005% and 0.1%, between 0.00001% and 0.5%, or between 0.00005% and 0.5% by weight. In another aspect, a composition provided herein comprises a food-grade preservative at a concentration between 0.01% and 1%, between 0.02% and 1%, between 0.03% and 1%, between 0.04% and 1%, between 0.05% and 1%, between 0.06% and 1%, between 0.07% and 1%, between 0.08% and 1%, between 0.09% and 1%, between 0.001% and 1%, between 0.005% and 1%, between 0.001% and 0.5%, or between 0.005% and 5% by weight. In another aspect, a composition provided herein comprises a food-grade preservative at a concentration between 0.01% and 0.1%, between 0.02% and 0.1%, between 0.03% and 0.1%, between 0.04% and 0.1%, between 0.05% and 0.1%, between 0.06% and 0.1%, between 0.07% and 0.1%, between 0.08% and 0.1%, between 0.09% and 0.1%, between 0.001% and 0.1%, between 0.005% and 0.1%, between 0.001% and 0.5%, or between 0.005% and 0.5% by weight. In still another aspect, a composition provided herein comprises a food-grade preservative at a concentration of up to and including 5%, up to and including 4%, up to and including 3%, up to and including 2%, up to and including 1%, up to and including 0.9%, up to and including 0.8%, up to and including 0.7%, up to and including 0.6%, up to and including 0.5%, up to and including 0.4%, up to and including 0.3%, up to and including 0.2%, up to and including 0.1%, up to and including 0.09%, up to and including 0.08%, up to and including 0.07%, up to and including 0.06%, up to and including 0.05%, up to and including 0.04%, up to and including 0.03%, up to and including 0.02%, or up to and including 0.01% by weight.

In an aspect, this disclosure provides a method comprising administering a composition comprising at least one food-grade preservative and a nucleic acid molecule to a bee or a *Varroa destructor* mite. In an aspect, this disclosure provides a method comprising administering a composition comprising at least two food-grade preservatives and a nucleic acid molecule to a bee or a *Varroa destructor* mite. In an aspect, this disclosure provides a method comprising administering a composition comprising at least three food-grade preservatives and a nucleic acid molecule to a bee or a *Varroa destructor* mite. In an aspect, this disclosure provides a method comprising administering a composition comprising at least four food-grade preservatives and a nucleic acid molecule to a bee or a *Varroa destructor* mite. In an aspect, this disclosure provides a method comprising administering a composition comprising at least five food-grade preservatives and a nucleic acid molecule to a bee or a *Varroa destructor* mite.

In an aspect, a composition provided herein comprises at least one food-grade preservative and a nucleic acid molecule. In an aspect, a composition provided herein comprises at least two food-grade preservatives and a nucleic acid molecule. In an aspect, a composition provided herein comprises at least three food-grade preservatives and a nucleic acid molecule. In an aspect, a composition provided herein comprises at least four food-grade preservatives and a nucleic acid molecule. In an aspect, a composition provided herein comprises at least five food-grade preservatives and a nucleic acid molecule.

In one aspect, this disclosure provides a method of protecting a nucleic acid molecule from degradation comprising adding at least one food-grade preservative to a composition comprising a carbohydrate and the nucleic acid molecule. As used herein, "protecting" refers to eliminating or slowing the rate of degradation of a starting concentration of a nucleic acid molecule present at a given time point as compared to a non-protected control. For example, without being bound by any scientific theory, the presence of a food-grade preservative in a composition protects a nucleic acid molecule from degradation by bacteria and/or fungi. Without being limiting, a suitable "non-protected" control would be an identical starting amount of the nucleic acid molecule in a composition that lacks a food-grade preservative component.

In an aspect, a method of protecting a nucleic acid molecule from degradation comprises the detectable presence of a nucleic acid molecule in a composition for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, at least 50, at least 55, or at least 60 days longer as compared to a composition lacking the at least one preservative.

pH ("potential of hydrogen") is measured on a logarithmic scale, generally from 1 to 14, although higher and lower pH values are possible. pH is the negative base 10 logarithm of the molar concentration of hydrogen ions in a solution. A solution with an equal number of hydrogen and hydroxide ions has a pH value of 7.0 and is considered to be "neutral." Without being limiting, an example of a neutral solution is pure water. pH values below 7.0 contain more hydrogen ions than hydroxide ions and are considered to be "acidic." pH values above 7.0 contain more hydroxide ions than hydrogen ions and are considered to be "basic." or "alkaline." Methods of determining the pH value of a solution are known in the art. Without being limiting, methods suitable for determining a pH value include indicator strips (e.g., litmus paper), indicator dyes, hydrogen-electrode methods, quinhydrone-electrode methods, antimony-electrode methods, and glass-electrode methods.

Some food-grade preservatives function more effectively in a particular pH range. For example, it is known that potassium sorbate and sodium benzoate are most effective at acidic pH values (e.g., less than 7.0). Potassium sorbate is known to be most effective at pH values below 6.0, although it maintains lower levels of effectiveness up to a pH value of 6.5. Sodium benzoate is known to be effective up to a maximum pH value of about 5.5.

In an aspect, a composition provided herein comprises a pH value of equal to or less than 9.0. In still another aspect, a composition provided herein comprises a pH value of equal to or greater than 9.0. In an aspect, a composition provided herein comprises a pH value of equal to or less than 8.0. In still another aspect, a composition provided herein comprises a pH value of equal to or greater than 8.0. In an aspect, a composition provided herein comprises a pH value of equal to or less than 7.0. In still another aspect, a composition provided herein comprises a pH value of equal to or greater than 7.0. In another aspect, a composition provided herein comprises a pH value of equal to or less than 6.5. In another aspect, a composition provided herein comprises a pH value of equal to or greater than 6.5. In another aspect, a composition provided herein comprises a pH value of equal to or less than 6.0. In another aspect, a composition provided herein comprises a pH value of equal to or greater than 6.0. In another aspect, a composition provided herein comprises a pH value of equal to or less than 5.5. In another aspect, a composition provided herein comprises a pH value of equal to or greater than 5.5. In another aspect, a composition provided herein comprises a pH value of equal to or less than 5.0. In another aspect, a composition provided herein comprises a pH value of equal to or greater than 5.0. In another aspect, a composition provided herein comprises a pH value of equal to or less than 4.5. In another aspect, a composition provided herein comprises a pH value of equal to or greater than 4.5.

In one aspect, a composition provided herein comprises a pH value of 3.0. In one aspect, a composition provided herein comprises a pH value of 3.1. In one aspect, a composition provided herein comprises a pH value of 3.2. In one aspect, a composition provided herein comprises a pH value of 3.3. In one aspect, a composition provided herein comprises a pH value of 3.4. In one aspect, a composition provided herein comprises a pH value of 3.5. In one aspect, a composition provided herein comprises a pH value of 3.6. In one aspect, a composition provided herein comprises a pH value of 3.7. In one aspect, a composition provided herein comprises a pH value of 3.8. In one aspect, a composition provided herein comprises a pH value of 3.9.

In one aspect, a composition provided herein comprises a pH value of 4.0. In one aspect, a composition provided herein comprises a pH value of 4.1. In one aspect, a composition provided herein comprises a pH value of 4.2. In one aspect, a composition provided herein comprises a pH value of 4.3. In one aspect, a composition provided herein comprises a pH value of 4.4. In one aspect, a composition provided herein comprises a pH value of 4.5. In one aspect, a composition provided herein comprises a pH value of 4.6. In one aspect, a composition provided herein comprises a pH value of 4.7. In one aspect, a composition provided herein comprises a pH value of 4.8. In one aspect, a composition provided herein comprises a pH value of 4.9.

In one aspect, a composition provided herein comprises a pH value of 5.0. In one aspect, a composition provided herein comprises a pH value of 5.1. In one aspect, a composition provided herein comprises a pH value of 5.2. In one aspect, a composition provided herein comprises a pH value of 5.3. In one aspect, a composition provided herein comprises a pH value of 5.4. In one aspect, a composition provided herein comprises a pH value of 5.5. In one aspect, a composition provided herein comprises a pH value of 5.6. In one aspect, a composition provided herein comprises a pH value of 5.7. In one aspect, a composition provided herein comprises a pH value of 5.8. In one aspect, a composition provided herein comprises a pH value of 5.9.

In one aspect, a composition provided herein comprises a pH value of 6.0. In one aspect, a composition provided herein comprises a pH value of 6.1. In one aspect, a composition provided herein comprises a pH value of 6.2. In one aspect, a composition provided herein comprises a pH value of 6.3. In one aspect, a composition provided herein comprises a pH value of 6.4. In one aspect, a composition provided herein comprises a pH value of 6.5. In one aspect, a composition provided herein comprises a pH value of 6.6. In one aspect, a composition provided herein comprises a pH value of 6.7. In one aspect, a composition provided herein comprises a pH value of 6.8. In one aspect, a composition provided herein comprises a pH value of 6.9.

In one aspect, a composition provided herein comprises a pH value of 7.0. In one aspect, a composition provided herein comprises a pH value of 7.1. In one aspect, a composition provided herein comprises a pH value of 7.2. In one aspect, a composition provided herein comprises a pH value of 7.3. In one aspect, a composition provided herein comprises a pH value of 7.4. In one aspect, a composition provided herein comprises a pH value of 7.5. In one aspect, a composition provided herein comprises a pH value of 7.6. In one aspect, a composition provided herein comprises a pH value of 7.7. In one aspect, a composition provided herein comprises a pH value of 7.8. In one aspect, a composition provided herein comprises a pH value of 7.9.

In one aspect, a composition provided herein comprises a pH value of 8.0. In one aspect, a composition provided herein comprises a pH value of 8.1. In one aspect, a composition provided herein comprises a pH value of 8.2. In one aspect, a composition provided herein comprises a pH value of 8.3. In one aspect, a composition provided herein comprises a pH value of 8.4. In one aspect, a composition provided herein comprises a pH value of 8.5. In one aspect, a composition provided herein comprises a pH value of 8.6. In one aspect, a composition provided herein comprises a pH value of 8.7. In one aspect, a composition provided herein comprises a pH value of 8.8. In one aspect, a composition provided herein comprises a pH value of 8.9.

In one aspect, a composition provided herein comprises a pH value of 9.0. In one aspect, a composition provided herein comprises a pH value of 9.1. In one aspect, a composition provided herein comprises a pH value of 9.2. In one aspect, a composition provided herein comprises a pH value of 9.3. In one aspect, a composition provided herein comprises a pH value of 9.4. In one aspect, a composition provided herein comprises a pH value of 9.5. In one aspect, a composition provided herein comprises a pH value of 9.6. In one aspect, a composition provided herein comprises a pH value of 9.7. In one aspect, a composition provided herein comprises a pH value of 9.8. In one aspect, a composition provided herein comprises a pH value of 9.9.

In an aspect, a composition provided herein comprises a pH value between 1.0 and 7.0, between 2.0 and 7.0, between 3.0 and 7.0, between 4.0 and 7.0, between 4.5 and 7.0, between 5.0 and 7.0, between 5.5 and 7.0, between 6.0 and 7.0, or between 6.5 and 7.0. In one aspect, a composition provided herein comprises a pH value between 4.0 and 7.0, between 4.5 and 7.0, between 5.0 and 7.0, between 5.5 and 7.0, between 6.0 and 7.0, or between 6.5 and 7.0. In another aspect, a composition provided herein comprises a pH value between 7.0 and 14.0, between 7.0 and 13.0, between 7.0 and 12.0, between 7.0 and 11.0, between 7.0 and 10.5, between 7.0 and 10.0, between 7.0 and 9.5, between 7.0 and 9.0, between 7.0 and 8.5, between 7.0 and 8.0, or between 7.0 and 7.5. In an aspect, a composition provided herein comprises a pH value between 2.0 and 5.5, between 2.5 and 5.5, between 3.0 and 5.5, between 3.5 and 5.5, between 4.0 and 5.5, between 4.5 and 5.5, or between 5.0 and 5.5.

Other Additions

In one aspect, a composition provided herein comprises honey.

In another aspect, a composition provided herein comprises a protein. In an aspect, a protein is selected from the group consisting of soy protein, pollen protein, yeast protein, and dairy protein. In an aspect, a composition provided herein comprises irradiated pollen protein. In another aspect, a composition provided herein comprises non-irradiated pollen protein. In one aspect, a yeast protein provided herein comprises brewer's yeast (e.g., *Saccharomyces cerevisiae*) protein. In another aspect, a yeast protein provided herein comprises torula (e.g., *Candida utilis*) protein. In one aspect, a soy protein provided herein comprises soy flour. In an aspect, a dairy protein provided herein comprises dry milk powder or non-fat dry milk powder.

In one aspect, a composition provided herein comprises vegetable oil. As used herein, "vegetable oil" refers to any triglyceride obtained from one or more plants. In an aspect, a vegetable oil provided herein is selected from the group consisting of soybean oil, cottonseed oil, canola oil, sunflower oil, palm oil, peanut oil, palm kernel oil, coconut oil, olive oil, corn oil, grape seed oil, hazelnut oil, linseed oil, sesame oil, safflower oil, or any combination thereof. In another aspect, a composition provided herein comprises vegetable shortening.

In another aspect, a composition provided herein comprises an essential oil. As used herein, "essential oil" refers to any hydrophobic liquid comprising volatile aroma compounds from one or more plants that repels mites. In another aspect, an essential oil provided herein is selected from the group consisting of wintergreen oil, tea tree oil, lemongrass oil, eucalyptus oil, cinnamon oil, neem oil, garlic oil, rosemary oil, oregano oil, sage oil, peppermint oil, and spearmint oil.

In one aspect, a composition provided herein comprises a vitamin. As used herein, a "vitamin" refers to any organic compound that is required by an organism to survive, typically in limited amounts. In an aspect, a vitamin provided herein comprises one or more vitamins selected from the list consisting of vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, and vitamin K.

In one aspect, a composition provided herein comprises a dietary mineral. As used herein, a "dietary mineral" refers to any chemical element that is required as an essential nutrient by a cell to perform one or more functions necessary for life. In an aspect, a dietary mineral provided herein comprises one or more dietary minerals selected from the group consisting of calcium, chromium, magnesium, manganese, sodium, potassium, and zinc.

In one aspect, a composition provided herein comprises an amino acid supplement. In an aspect, an amino acid supplement provided herein comprises one or more amino acids selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, and derivatives thereof.

In one aspect, a composition provided herein comprises a hydrocolloid. Without being limiting, hydrocolloids can maintain particles in suspension when mixed with water or other liquids. In an aspect, a hydrocolloid is selected from the group consisting of xanthan gum, locust bean gum, an alginate, a carrageenan, gum arabic, guar gum, carboxymethylcellulose, pectin, and agar. In an aspect, a composition provided herein comprises between 0% and 5%, between 0% and 4%, between 0% and 3%, between 0% and 2%, between 0% and 1%, between 0% and 0.5%, between 0.01% and 5%, between 0.01% and 4%, between 0.01% and 3%, between 0.01% and 2%, between 0.01% and 1%, or between 0.01% and 0.5% of a hydrocolloid by weight.

In an aspect, a composition provided herein comprises an ingredient selected from the group consisting of a hydrocolloid, a vegetable oil, an essential oil, a vitamin, a dietary mineral, an amino acid supplement, or any combination thereof.

dsRNAs to Target Mites

It has been shown that nucleic acid molecules can be provided in a diet to *Varroa* mites to down-regulate the expression of a *Varroa* mite gene product. See, for example, U.S. Pat. Nos. 8,962,584; 9,540,642; and 9,662,348, each of which is incorporated by reference herein in its entirety. Non-limiting examples of gene products include messenger RNAs (mRNAs), proteins, and small RNAs. Nucleic acid molecules that are complementary to *Varroa* mite gene products can be used to cause mortality of a *Varroa* mite, to reduce the fecundity of a *Varroa* mite, to prevent *Varroa* mite infestation of a beehive, to treat a *Varroa* mite infestation of a beehive, or make a *Varroa* mite more susceptible to additional treatments that cause mortality of a *Varroa* mite (e.g., commercial miticides).

As used herein, the term "fecundity" refers to the ability to produce offspring; higher fecundity refers to the ability to produce more offspring, while reduced fecundity refers to the ability to produce fewer offspring. For example, without being limiting, an untreated *Varroa* mite may lay up to six eggs, while a *Varroa* mite treated with a composition provided herein with reduced fecundity may only lay up to five eggs. In an aspect, a method provided herein comprises reducing the fecundity of an arthropod. In another aspect, a method provided herein comprises reducing the fecundity of a mite. In a further aspect, a method provided herein comprises reducing the fecundity of a *Varroa destructor* mite.

In an aspect, reduced fecundity comprises a reduction in mite egg production in a beehive or bee colony of at least 1%, at least 5%, at least 10%, at least 20%, at least 30%, at least 40%, at least 50%, at least 60%, at least 70%, at least 80%, at least 90%, or at least 100% as compared to mite egg production an untreated control beehive or bee colony. In an aspect, reduced fecundity comprises a reduction in *Varroa destructor* mite egg production in a beehive or bee colony of at least 1%, at least 5%, at least 10%, at least 20%, at least 30%, at least 40%, at least 50%, at least 60%, at least 70%, at least 80%, at least 90%, or at least 100% as compared to *Varroa destructor* mite egg production an untreated control beehive or bee colony.

In an aspect, reduced fecundity comprises a below replacement rate level of reproduction. In an aspect, reduced fecundity comprises a replacement rate level of reproduction. As used herein, "replacement rate" refers to the fertility rate at which female mites produce enough offspring to sustain or maintain the population level in a beehive or bee colony. In the absence of female mortality between birth and the end of egg-laying, the replacement rate would be approximately 2. However, due to non-zero mortality rates, replacement rates are often higher than 2. For example, if the replacement rate is 2, a female *Varroa destructor* mite would need to produce 2 offspring to maintain the population level. If the replacement rate is 2, a female *Varroa destructor* mite that produces 3 offspring would be reproducing at a rate above the replacement rate.

In one aspect, methods provided herein comprise administering a composition provided herein to a bee. In another aspect, methods provided herein comprise administering a composition provided herein to a *Varroa destructor* mite. In another aspect, methods provided herein comprise administering a composition provided herein to an arthropod. In an aspect, methods provided herein comprise administering a composition provided herein to a mite.

In one aspect, administering a composition provided herein to a mite in a beehive reduces the lifespan of the mite as compared to the lifespan of a mite in a control beehive that was not administered the composition. In one aspect, administering a composition provided herein to a mite reduces the lifespan of the mite as compared to the lifespan of a control mite that was not administered the composition. In one aspect, administering a composition provided herein to a *Varroa destructor* mite in a beehive reduces the lifespan of the *Varroa destructor* mite as compared to the lifespan of a *Varroa destructor* mite in a control beehive that was not administered the composition. In one aspect, administering a composition provided herein to a *Varroa destructor* mite reduces the lifespan of the mite as compared to the lifespan of a control *Varroa destructor* mite that was not administered the composition.

In one aspect, administering a composition provided herein to a mite in a beehive reduces the fecundity of the mite as compared to the fecundity of a mite in a control beehive that was not administered the composition. In one aspect, administering a composition provided herein to a mite reduces the fecundity of the mite as compared to the fecundity of a control mite that was not administered the composition. In one aspect, administering a composition provided herein to a *Varroa destructor* mite in a beehive reduces the fecundity of the *Varroa destructor* mite as compared to the fecundity of a *Varroa destructor* mite in a control beehive that was not administered the composition. In one aspect, administering a composition provided herein to a *Varroa destructor* mite reduces the fecundity of the mite as compared to the fecundity of a control *Varroa destructor* mite that was not administered the composition.

In an aspect, in a method provided herein a bee is infested by at least one mite. In another aspect, in a method provided herein a beehive is infested by at least one mite. In still another aspect, a bee colony is infested by at least one mite. In an aspect, in a method provided herein a bee is infested by at least one *Varroa destructor* mite. In another aspect, in a method provided herein a beehive is infested by at least one *Varroa destructor* mite. In still another aspect, a bee colony is infested by at least one *Varroa destructor* mite.

In another aspect, in a method provided herein a beehive is infested by at least 5 mites, at least 10 mites, at least 25 mites, at least 50 mites, at least 75 mites, at least 100 mites, at least 200 mites, at least 500 mites, or at least 1000 mites. In still another aspect, a bee colony is infested by at least 5 mites, at least 10 mites, at least 25 mites, at least 50 mites, at least 75 mites, at least 100 mites, at least 200 mites, at least 500 mites, or at least 1000 mites. In another aspect, in a method provided herein a beehive is infested by at least 5 *Varroa destructor* mites, at least 10 *Varroa destructor* mites, at least 25 *Varroa destructor* mites, at least 50 *Varroa destructor* mites, at least 75 *Varroa destructor* mites, at least 100 *Varroa destructor* mites, at least 200 *Varroa destructor* mites, at least 500 *Varroa destructor* mites, or at least 1000 *Varroa destructor* mites. In still another aspect, a bee colony is infested by at least 5 *Varroa destructor* mites, at least 10 *Varroa destructor* mites, at least 25 *Varroa destructor* mites, at least 50 *Varroa destructor* mites, at least 75 *Varroa destructor* mites, at least 100 *Varroa destructor* mites, at least 200 *Varroa destructor* mites, at least 500 *Varroa destructor* mites, or at least 1000 *Varroa destructor* mites.

In one aspect, composition provided herein comprises a nucleic acid molecule. In another aspect, a composition provided herein comprises a nucleic acid molecule complementary to an arthropod gene product. In a further aspect, a composition provided herein comprises a nucleic acid molecule complementary to a mite gene product. In a further aspect, a composition provided herein comprises a nucleic acid molecule complementary to a *Varroa destructor* gene product. In another aspect, a composition provided herein comprises a nucleic acid molecule identical to an arthropod gene product. In a further aspect, a composition provided herein comprises a nucleic acid molecule identical to a mite gene product. In a further aspect, a composition provided herein comprises a nucleic acid molecule identical to a *Varroa destructor* gene product.

In another aspect, a composition provided herein comprises a nucleic acid molecule complementary to an arthropod gene product. In a further aspect, a composition provided herein comprises a nucleic acid molecule comprising at least 75%, at least 80%, at least 85%, at least 90%, at least 91%, at least 92%, at least 93%, at least 94%, at least 95%, at least 96%, at least 97%, at least 98%, or at least 99% complementary to a mite gene product. In a further aspect, a composition provided herein comprises a nucleic acid molecule comprising at least 75%, at least 80%, at least 85%, at least 90%, at least 91%, at least 92%, at least 93%, at least 94%, at least 95%, at least 96%, at least 97%, at least 98%, or at least 99% complementary to a *Varroa destructor* gene product. In another aspect, a composition provided herein comprises a nucleic acid molecule comprising at least 75%, at least 80%, at least 85%, at least 90%, at least 91%, at least 92%, at least 93%, at least 94%, at least 95%, at least 96%, at least 97%, at least 98%, or at least 99% identity to an arthropod gene product. In a further aspect, a composition provided herein comprises a nucleic acid molecule comprising at least 75%, at least 80%, at least 85%, at least 90%, at least 91%, at least 92%, at least 93%, at least 94%, at least 95%, at least 96%, at least 97%, at least 98%, or at least 99% identity to a mite gene product. In a further aspect, a composition provided herein comprises a nucleic acid molecule comprising at least 75%, at least 80%, at least 85%, at least 90%, at least 91%, at least 92%, at least 93%, at least 94%, at least 95%, at least 96%, at least 97%, at least 98%, or at least 99% identity to a *Varroa destructor* gene product.

In yet another aspect, a composition provided herein comprises at least one, at least two, at least three, at least four, at least five, at least six, at least seven, at least eight, at least nine, or at least ten different nucleic acid molecules complementary to at least one, at least two, at least three, at least four, at least five, at least six, at least seven, at least eight, at least nine, or at least ten different arthropod gene products. In yet another aspect, a composition provided herein comprises at least one, at least two, at least three, at least four, at least five, at least six, at least seven, at least eight, at least nine, or at least ten different nucleic acid molecules complementary to at least one, at least two, at least three, at least four, at least five, at least six, at least seven, at least eight, at least nine, or at least ten different mite gene products. In yet another aspect, a composition provided herein comprises at least one, at least two, at least three, at least four, at least five, at least six, at least seven, at least eight, at least nine, or at least ten different nucleic acid molecules complementary to at least one, at least two, at least three, at least four, at least five, at least six, at least seven, at least eight, at least nine, or at least ten different *Varroa destructor* gene products.

In an aspect, a composition provided herein comprises a first nucleic acid molecule and a second nucleic acid molecule, wherein the first nucleic acid molecule is complementary to a first *Varroa destructor* gene product and the second nucleic acid molecule is complementary to a second *Varroa destructor* gene product.

In an aspect, a nucleic acid molecule provided herein is a single-stranded nucleic acid molecule. In another aspect, a nucleic acid molecule provided herein is a double-stranded nucleic acid molecule. In one aspect, a nucleic acid molecule provided herein is a deoxyribonucleic acid (DNA) molecule. In another aspect, a nucleic acid molecule provided herein is a ribonucleic acid (RNA) molecule. In a further aspect, a nucleic acid molecule provided herein is a double-stranded RNA (dsRNA) molecule.

In an aspect, a nucleic acid molecule provided herein is transcribable. In another aspect, a nucleic acid molecule provided herein is non-transcribable.

In an aspect, a nucleic acid molecule provided herein is a small RNA molecule. Non-limiting examples of small RNA molecules include microRNAs (miRNAs), small interfering RNAs (siRNAs), ribosomal RNAs (rRNAs), transfer RNAs (tRNAs), trans-acting siRNAs (ta-siRNAs), hairpin RNAs (hpRNAs), Piwi-interacting RNAs (piwiRNAs), small nucleolar RNAs (snoRNAs), heterochromatic siRNAs (hc-siRNAs), activating RNAs (acRNAs), natural anti-sense siRNA (nat-siRNA), cis-acting siRNAs, long miRNAs, epigenetically-activated siRNAs, and precursors thereof. In an aspect, a nucleic acid molecule provided herein is selected from the group consisting of a microRNA, a small interfering RNA (siRNA), a trans-acting siRNA, a hairpin RNA, a Piwi-interacting RNA, a small nucleolar RNA, a heterochromatic siRNA, an activating RNA, a natural anti-sense siRNA, a cis-acting siRNA, a long miRNA, an epigenetically-activated siRNA, or precursors thereof.

In an aspect, a nucleic acid molecule provided herein comprises at least 20 nucleotides, at least 25 nucleotides, at least 30 nucleotides, at least 40 nucleotides, at least 50 nucleotides, at least 75 nucleotides, at least 100 nucleotides, at least 150 nucleotides, at least 200 nucleotides, at least 300 nucleotides, at least 400 nucleotides, at least 500 nucleotides, at least 600 nucleotides, at least 700 nucleotides, at least 750 nucleotides, at least 800 nucleotides, at least 900 nucleotides, at least 1000 nucleotides, at least 2500 nucleotides, or at least 5000 nucleotides in length.

In an aspect, a nucleic acid molecule provided herein comprises between 20 and 5000 nucleotides, between 20 and 2500 nucleotides, between 20 and 1000 nucleotides, between 20 and 900 nucleotides, between 20 and 800 nucleotides, between 20 and 700 nucleotides, between 20 and 600 nucleotides, between 20 and 500 nucleotides, between 20 and 400 nucleotides, between 20 and 300 nucleotides, between 20 and 200 nucleotides, between 20 and 150 nucleotides, between 20 and 100 nucleotides, between 20 and 75 nucleotides, between 20 and 50 nucleotides, between 20 and 40 nucleotides, between 20 and 30 nucleotides, between 20 and 25 nucleotides, between 20 and 28 nucleotides, between 50 and 500 nucleotides, or between 100 and 1000 nucleotides in length.

In one aspect, a nucleic acid molecule provided herein is identical or complementary to at least 20, at least 21, at least 22, at least 23, at least 24, at least 25, at least 26, at least 27, at least 28, at least 29, or at least 30 contiguous nucleotides of an arthropod mRNA. In one aspect, a nucleic acid molecule provided herein is identical or complementary to at least 18, at least 19, at least 20, at least 21, at least 22, at least 23, at least 24, at least 25, at least 26, at least 27, at least 28, at least 29, or at least 30 contiguous nucleotides of a mite mRNA. In one aspect, a nucleic acid molecule provided herein is identical or complementary to at least 18, at least 19, at least 20, at least 21, at least 22, at least 23, at least 24, at least 25, at least 26, at least 27, at least 28, at least 29, or at least 30 contiguous nucleotides of a *Varroa destructor* mRNA.

In one aspect, a dsRNA provided herein comprises at least one strand that is identical or complementary to at least 20, at least 21, at least 22, at least 23, at least 24, at least 25, at least 26, at least 27, at least 28, at least 29, or at least 30 contiguous nucleotides of an arthropod mRNA. In one aspect, a dsRNA provided herein comprises at least one strand that is identical or complementary to at least 18, at least 19, at least 20, at least 21, at least 22, at least 23, at least 24, at least 25, at least 26, at least 27, at least 28, at least 29, or at least 30 contiguous nucleotides of a mite mRNA. In one aspect, a dsRNA provided herein comprises at least one strand that is identical or complementary to at least 18, at least 19, at least 20, at least 21, at least 22, at least 23, at least 24, at least 25, at least 26, at least 27, at least 28, at least 29, or at least 30 contiguous nucleotides of a *Varroa destructor* mRNA.

In an aspect, a dsRNA provided herein is capable of inhibiting the expression of an arthropod mRNA. As used herein, "expression" refers to the transcription of a DNA molecule to an RNA molecule and/or the translation of an RNA molecule into a protein. In another aspect, a dsRNA provided herein is capable of inhibiting the transcription of an arthropod mRNA. In another aspect, a dsRNA provided herein is capable of inhibiting the translation of an arthropod mRNA. In an aspect, a dsRNA provided herein is capable of inhibiting the expression of a mite mRNA. In another aspect, a dsRNA provided herein is capable of inhibiting the transcription of a mite mRNA. In another aspect, a dsRNA provided herein is capable of inhibiting the translation of a mite mRNA. In an aspect, a dsRNA provided herein is capable of inhibiting the expression of a *Varroa destructor* mRNA. In another aspect, a dsRNA provided herein is capable of inhibiting the transcription of a *Varroa destructor* mRNA. In another aspect, a dsRNA provided herein is capable of inhibiting the translation of a *Varroa destructor* mRNA.

In an aspect, administering a nucleic acid molecule provided herein to an arthropod results in the down-regulation of at least one mRNA of the arthropod. In an aspect, administering a dsRNA provided herein to an arthropod results in the down-regulation of at least one mRNA of the arthropod. In an aspect, administering a nucleic acid molecule provided herein to a mite results in the down-regulation of at least one mRNA of the mite. In an aspect, administering a dsRNA provided herein to a mite results in the down-regulation of at least one mRNA of the mite. In an aspect, administering a nucleic acid molecule provided herein to a *Varroa destructor* mite results in the down-regulation of at least one mRNA of the *Varroa destructor* mite. In an aspect, administering a dsRNA provided herein to a *Varroa destructor* mite results in the down-regulation of at least one mRNA of the *Varroa destructor* mite.

In an aspect, administering a nucleic acid molecule provided herein to an arthropod results in the down-regulation of at least one protein of the arthropod. In an aspect, administering a dsRNA provided herein to an arthropod results in the down-regulation of at least one protein of the arthropod. In an aspect, administering a nucleic acid molecule provided herein to a mite results in the down-regulation of at least one protein of the mite. In an aspect, administering a dsRNA provided herein to a mite results in the down-regulation of at least one protein of the mite. In an aspect, administering a nucleic acid molecule provided herein to a *Varroa destructor* mite results in the down-regulation of at least one protein of the *Varroa destructor* mite. In an aspect, administering a dsRNA provided herein to a *Varroa destructor* mite results in the down-regulation of at least one protein of the *Varroa destructor* mite.

*Varroa* mites parasitize larval, pupal, and adult bees and reproduce in the pupal brood cells. *Varroa* mites feed on brood food inside brood cells. *Varroa* mites also use their mouths to puncture the exoskeleton of a bee and feed on the bee. These wound sites in the exoskeleton harbor bacterial infections, such as *Melissococcus pluton*, which causes European foulbrood.

Many viruses are known to infect bees and cause loss of bee life and/or reduce bee productivity. Viruses can cause physiological changes, behavioral changes, or both, in infected bees. Arthropods (e.g., mites) are known as, or suspected to be, vectors that transmit many viruses to susceptible bees and other arthropods. In an aspect, a nucleic acid molecule provided herein is identical or complementary to at least 20, at least 21, at least 22, at least 23, at least 24, at least 25, at least 26, at least 27, at least 28, at least 29, or at least 30 contiguous nucleotides of an arthropod virus nucleic acid. In another aspect, a dsRNA provided herein comprises at least one strand that is identical to, or complementary to, at least 20, at least 21, at least 22, at least 23, at least 24, at least 25, at least 26, at least 27, at least 28, at least 29, or at least 30 contiguous nucleotides of an arthropod virus nucleic acid.

As used herein, a "bee virus" refers to any virus capable of infecting a bee. Without being limiting, bee viruses can be transmitted directly from bee-to-bee, through infected water or food, or via a vector such as a *Varroa* mite. *Varroa* mites are suspected of transmitting numerous viruses to bees. If left untreated *Varroa* infestations typically result in colony-level mortality. Treatment of viral infections by down-regulation of a particular viral gene product has shown to be successful in eliminating virally induced infections in the bee (see U.S. Patent Publication 2009/0118214).

In an aspect, an arthropod virus provided herein is a bee virus. In another aspect, a bee virus is selected from the group consisting of acute bee paralysis virus, aphid lethal paralysis virus, *Apis* iridescent virus, *Apis mellifera* filamentous virus, Arkansas bee virus, bee virus X, bee virus Y, Berkeley bee virus, Big Sioux River virus, black queen cell virus, chronic bee paralysis virus, cloudy wing virus, deformed wing virus, Egypt bee virus, invertebrate iridescent virus type 6, Israeli acute paralysis virus, kakugo virus, Kashmir bee virus, Lake Sinai virus-1, Lake Sinai virus-2, sacbrood virus, satellite virus, slow bee paralysis virus, Thai sacbrood virus, tobacco ringspot virus, and *Varroa destructor* virus. In an aspect, a bee virus is selected from the group consisting of acute bee paralysis virus, Kashmir bee virus, and Israeli acute paralysis virus. In another aspect, a bee virus is selected from the group consisting of aphid lethal paralysis virus and Big Sioux River virus. In a further aspect, a bee virus is selected from the group consisting of deformed wing virus, Kakugo virus, *Varroa destructor* virus, and Egypt bee virus. In still another aspect, a bee virus is selected from the group consisting of sacbrood virus and Thai sacbrood virus. In still a further aspect, a bee virus is selected from the group consisting of chronic bee paralysis virus and satellite virus. In an aspect, a bee virus is selected from the group consisting of bee virus X and bee virus Y. In one aspect, a bee virus is selected from the group consisting of Lake Sinai virus-1 and Lake Sinai virus-2. In an aspect, a bee virus is selected from the group consisting of Arkansas bee virus and Berkeley bee virus.

In an aspect, a nucleic acid molecule provided herein is not 100% complementary or identical to 19 or more contiguous nucleotides of a bee mRNA. In an aspect, a nucleic acid molecule provided herein is not 100% complementary or identical to 19 or more contiguous nucleotides of a human mRNA. In another aspect, a nucleic acid molecule provided herein is not 100% complementary or identical to 19 or more contiguous nucleotides of any bee genome sequence. In a further aspect, a nucleic acid molecule provided herein is not 100% complementary or identical to 19 or more contiguous nucleotides of any human genome sequence.

In one aspect, the concentration of a nucleic acid molecule in a composition provided herein is at least 0.00001 mg/mL, at least 0.00005 mg/mL, at least 0.0001 mg/mL, at least 0.0005 mg/mL, at least 0.001 mg/mL, at least 0.005 mg/mL, at least 0.01 mg/mL, at least 0.05 mg/mL, at least 0.1 mg/mL, at least 0.5 mg/mL, at least 1 mg/mL, at least 5 mg/mL, at least 10 mg/mL, at least 15 mg/mL, at least 20 mg/mL, or at least 50 mg/mL. In one aspect, the concentration of a nucleic acid molecule in a composition provided herein is at least 0.00001 mg/mL. In one aspect, the concentration of a nucleic acid molecule in a composition provided herein is 0.00005 mg/mL. In one aspect, the concentration of a nucleic acid molecule in a composition provided herein is at least 0.0001 mg/mL. In one aspect, the concentration of a nucleic acid molecule in a composition provided herein is at least 0.0005 mg/mL. In one aspect, the concentration of a nucleic acid molecule in a composition provided herein is at least 0.001 mg/mL. In one aspect, the concentration of a nucleic acid molecule in a composition provided herein is at least 0.005 mg/mL. In one aspect, the concentration of a nucleic acid molecule in a composition provided herein is at least 0.01 mg/mL. In one aspect, the concentration of a nucleic acid molecule in a composition provided herein is at least 0.05 mg/mL. In one aspect, the concentration of a nucleic acid molecule in a composition provided herein is at least 0.1 mg/mL. In one aspect, the concentration of a nucleic acid molecule in a composition provided herein is at least 0.5 mg/mL. In one aspect, the concentration of a nucleic acid molecule in a composition provided herein is at least 1 mg/mL. In one aspect, the concentration of a nucleic acid molecule in a composition provided herein is at least 5 mg/mL. In one aspect, the concentration of a nucleic acid molecule in a composition provided herein is at least 10 mg/mL. In one aspect, the concentration of a nucleic acid molecule in a composition provided herein is at least 15 mg/mL. In one aspect, the concentration of a nucleic acid molecule in a composition provided herein is at least 20 mg/mL. In one aspect, the concentration of a nucleic acid molecule in a composition provided herein is at least 50 mg/mL.

In another aspect, the concentration of a nucleic acid molecule in a composition provided herein is between 0.00001 mg/mL and 20 mg/mL, between 0.00005 mg/mL and 20 mg/mL, between 0.0001 mg/mL and 20 mg/mL, between 0.0005 mg/mL and 20 mg/mL, between 0.001 mg/mL and 20 mg/mL, between 0.005 mg/mL and 20 mg/mL, between 0.01 mg/mL and 20 mg/mL, between 0.05 mg/mL and 20 mg/mL, between 0.1 mg/mL and 20 mg/mL, between 0.5 mg/mL and 20 mg/mL, between 1 mg/mL and 20 mg/mL, between 5 mg/mL and 20 mg/mL, between 10 mg/mL and 20 mg/mL, or between 15 mg/mL and 20 mg/mL. In another aspect, the concentration of a nucleic acid molecule in a composition provided herein is between 0.001 mg/mL and 10 mg/mL, between 0.001 mg/mL and 5 mg/mL, between 0.001 mg/mL and 1 mg/mL, between 0.001 mg/mL and 0.5 mg/mL, or between 0.001 mg/mL and 0.1 mg/mL.

In one aspect, a nucleic acid molecule provided herein is present in brood food. In another aspect, a nucleic acid molecule provided herein is present in royal jelly. In yet another aspect, a nucleic acid molecule provided herein is present in brood food. In another aspect, nucleic acid molecule dsRNA provided herein is present in wax. In another aspect, a nucleic acid molecule provided herein is present in water.

In yet another aspect, a dsRNA provided herein is present in brood food. In a further aspect, a dsRNA provided herein is present in royal jelly. In another aspect, a dsRNA provided herein is present in wax. In another aspect, a dsRNA provided herein is present in water.

Without being limiting, *Varroa* mites can ingest nucleic acids that are complementary to, and down-regulate, viral RNAs harbored and/or transmitted by *Varroa* mites by ingesting any composition (e.g., brood food, royal jelly, wax, water) that comprises the nucleic acids. Without being limiting, *Varroa* mites can absorb nucleic acids that are complementary to, and down-regulate, viral RNAs harbored and/or transmitted by *Varroa* mites by contacting any composition (e.g., brood food, royal jelly, wax, water) that comprises the nucleic acids.

Without being limiting, *Varroa* mites can ingest nucleic acids that are complementary to, and down-regulate, *Varroa* mite messenger RNAs by ingesting any composition (e.g., brood food, royal jelly, wax, water) that comprises the nucleic acids. Without being limiting, *Varroa* mites can absorb nucleic acids that are complementary to, and down-regulate, *Varroa* mite messenger RNAs by contacting any composition (e.g., brood food, royal jelly, wax, water) that comprises the nucleic acids.

In an aspect, this disclosure provides a method of treating or preventing a *Varroa destructor* mite infestation of a beehive comprising administering a composition comprising: (a) at least one carbohydrate; (b) at least one dsRNA comprising a nucleotide sequence complementary to 20 or more contiguous nucleotides of a *Varroa destructor* mite messenger RNA (mRNA); and (c) at least one food-grade preservative to the beehive, thereby treating or preventing the *Varroa destructor* mite infestation. In another aspect, this disclosure provides a method of treating or preventing a *Varroa destructor* mite infestation of a beehive comprising administering a composition comprising: (a) at least one carbohydrate; (b) at least one nucleic acid molecule comprising a nucleotide sequence complementary to 20 or more contiguous nucleotides of a *Varroa destructor* mite messenger RNA (mRNA); and (c) at least one food-grade preservative to the beehive, thereby treating or preventing the *Varroa destructor* mite infestation.

Dual Treatment

In an aspect, this disclosure provides a method of treating or preventing an arthropod infestation of a beehive or bee colony comprising: (a) providing to the beehive or bee colony a composition comprising a nucleic acid molecule that is complementary or identical to at least 21 contiguous nucleotides of an arthropod messenger RNA (mRNA); and (b) providing an agent to control mites to the beehive or bee colony, thereby treating or preventing the arthropod infestation of the beehive or bee colony. In another aspect, this disclosure provides a method of treating or preventing a mite infestation of a beehive or bee colony comprising: (a) providing to the beehive or bee colony a composition comprising a nucleic acid molecule that is complementary or identical to at least 21 contiguous nucleotides of a mite messenger RNA (mRNA); and (b) providing an agent to control mites to the beehive or bee colony, thereby treating or preventing the mite infestation of the beehive or bee colony. In still another aspect, this disclosure provides a method of treating or preventing a *Varroa destructor* mite infestation of a beehive or bee colony comprising: (a) providing to the beehive or bee colony a composition comprising a nucleic acid molecule that is complementary or identical to at least 21 contiguous nucleotides of a *Varroa destructor* mite messenger RNA (mRNA); and (b) providing an agent to control mites to the beehive or bee colony, thereby treating or preventing the *Varroa destructor* mite infestation of the beehive or bee colony.

In another aspect, this disclosure provides a method of causing mortality or reducing the fecundity of an arthropod comprising: (a) providing a composition comprising a nucleic acid molecule complementary to an arthropod messenger RNA (mRNA) to the arthropod; and (b) providing an agent to control mites to the arthropod, thereby causing mortality or reducing the fecundity of the arthropod. In another aspect, this disclosure provides a method of causing mortality or reducing the fecundity of a mite comprising: (a) providing a composition comprising a nucleic acid molecule complementary to a mite messenger RNA (mRNA) to the mite; and (b) providing an agent to control mites to the mite, thereby causing mortality or reducing the fecundity of the mite. In another aspect, this disclosure provides a method of causing mortality or reducing the fecundity of a *Varroa destructor* mite comprising: (a) providing a composition comprising a nucleic acid molecule complementary to a *Varroa destructor* mite messenger RNA (mRNA) to the *Varroa destructor* mite; and (b) providing an agent to control mites to the *Varroa destructor* mite, thereby causing mortality or reducing the fecundity of the *Varroa destructor* mite. In an aspect, a method provided herein causes mortality of an arthropod within 1 day of providing a composition comprising a nucleic acid sequence. In an aspect, a method provided herein causes mortality of an arthropod within 2 days of providing a composition comprising a nucleic acid sequence. In an aspect, a method provided herein causes mortality of an arthropod within 3 days of providing a composition comprising a nucleic acid sequence. In an aspect, a method provided herein causes mortality of an arthropod within 4 days of providing a composition comprising a nucleic acid sequence. In an aspect, a method provided herein causes mortality of an arthropod within 5 days of providing a composition comprising a nucleic acid sequence. In an aspect, a method provided herein causes mortality of an arthropod within 6 days of providing a composition comprising a nucleic acid sequence. In an aspect, a method provided herein causes mortality of an arthropod within 7 days of providing a composition comprising a nucleic acid sequence. In an aspect, a method provided herein causes mortality of an arthropod within 8 days of providing a composition comprising a nucleic acid sequence. In an aspect, a method provided herein causes mortality of an arthropod within 9 days of providing a composition comprising a nucleic acid sequence. In an aspect, a method provided herein causes mortality of an arthropod within 10 days of providing a composition comprising a nucleic acid sequence. In an aspect, a method provided herein causes mortality of an arthropod within 11 days of providing a composition comprising a nucleic acid sequence. In an aspect, a method provided herein causes mortality of an arthropod within 12 days of providing a composition comprising a nucleic acid sequence. In an aspect, a method provided herein causes mortality of an arthropod within 13 days of providing a composition comprising a nucleic acid sequence. In an aspect, a method provided herein causes mortality of an arthropod within 14 days of providing a composition comprising a nucleic acid sequence. In an aspect, a method provided herein causes mortality of an arthropod within 15 days of providing a composition comprising a nucleic acid sequence. In an aspect, a method provided herein causes mortality of an arthropod within 20 days of providing a composition comprising a nucleic acid sequence. In an aspect, a method provided herein causes mortality of an arthropod within 25 days of providing a composition comprising a nucleic acid sequence. In an aspect, a method provided herein causes mortality of an arthropod within 30 days of providing a composition comprising a nucleic acid sequence.

In an aspect, a method provided herein causes mortality of a mite within 1 day of providing a composition comprising a nucleic acid sequence. In an aspect, a method provided herein causes mortality of a mite within 2 days of providing a composition comprising a nucleic acid sequence. In an aspect, a method provided herein causes mortality of a mite within 3 days of providing a composition comprising a nucleic acid sequence. In an aspect, a method provided herein causes mortality of a mite within 4 days of providing a composition comprising a nucleic acid sequence. In an aspect, a method provided herein causes mortality of a mite within 5 days of providing a composition comprising a nucleic acid sequence. In an aspect, a method provided herein causes mortality of a mite within 6 days of providing a composition comprising a nucleic acid sequence. In an aspect, a method provided herein causes mortality of a mite within 7 days of providing a composition comprising a nucleic acid sequence. In an aspect, a method provided herein causes mortality of a mite within 8 days of providing a composition comprising a nucleic acid sequence. In an aspect, a method provided herein causes mortality of a mite within 9 days of providing a composition comprising a nucleic acid sequence. In an aspect, a method provided herein causes mortality of a mite within 10 days of providing a composition comprising a nucleic acid sequence. In an aspect, a method provided herein causes mortality of a mite within 11 days of providing a composition comprising a nucleic acid sequence. In an aspect, a method provided herein causes mortality of a mite within 12 days of providing a composition comprising a nucleic acid sequence. In an aspect, a method provided herein causes mortality of a mite within 13 days of providing a composition comprising a nucleic acid sequence. In an aspect, a method provided herein causes mortality of a mite within 14 days of providing a composition comprising a nucleic acid sequence. In an aspect, a method provided herein causes mortality of a mite within 15 days of providing a composition comprising a nucleic acid sequence. In an aspect, a method provided herein causes mortality of a mite within 20 days of providing a composition comprising a nucleic acid sequence. In an aspect, a method provided herein causes mortality of a mite within 25 days of providing a composition comprising a nucleic acid sequence. In an aspect, a method provided herein causes mortality of a mite within 30 days of providing a composition comprising a nucleic acid sequence.

In an aspect, a method provided herein causes mortality of a *Varroa destructor* mite within 1 day of providing a composition comprising a nucleic acid sequence. In an aspect, a method provided herein causes mortality of a *Varroa destructor* mite within 2 days of providing a composition comprising a nucleic acid sequence. In an aspect, a method provided herein causes mortality of a *Varroa destructor* mite within 3 days of providing a composition comprising a nucleic acid sequence. In an aspect, a method provided herein causes mortality of a *Varroa destructor* mite within 4 days of providing a composition comprising a nucleic acid sequence. In an aspect, a method provided herein causes mortality of a *Varroa destructor* mite within 5 days of providing a composition comprising a nucleic acid sequence. In an aspect, a method provided herein causes mortality of a *Varroa destructor* mite within 6 days of providing a composition comprising a nucleic acid sequence. In an aspect, a method provided herein causes mortality of a *Varroa destructor* mite within 7 days of providing a composition comprising a nucleic acid sequence. In an aspect, a method provided herein causes mortality of a *Varroa destructor* mite within 8 days of providing a composition comprising a nucleic acid sequence. In an aspect, a method provided herein causes mortality of a *Varroa destructor* mite within 9 days of providing a composition comprising a nucleic acid sequence. In an aspect, a method provided herein causes mortality of a *Varroa destructor* mite within 10 days of providing a composition comprising a nucleic acid sequence. In an aspect, a method provided herein causes mortality of a *Varroa destructor* mite within 11 days of providing a composition comprising a nucleic acid sequence. In an aspect, a method provided herein causes mortality of a *Varroa destructor* mite within 12 days of providing a composition comprising a nucleic acid sequence. In an aspect, a method provided herein causes mortality of a *Varroa destructor* mite within 13 days of providing a composition comprising a nucleic acid sequence. In an aspect, a method provided herein causes mortality of a *Varroa destructor* mite within 14 days of providing a composition comprising a nucleic acid sequence. In an aspect, a method provided herein causes mortality of a *Varroa destructor* mite within 15 days of providing a composition comprising a nucleic acid sequence. In an aspect, a method provided herein causes mortality of a *Varroa destructor* mite within 20 days of providing a composition comprising a nucleic acid sequence. In an aspect, a method provided herein causes mortality of a *Varroa destructor* mite within 25 days of providing a composition comprising a nucleic acid sequence. In an aspect, a method provided herein causes mortality of a *Varroa destructor* mite within 30 days of providing a composition comprising a nucleic acid sequence.

In an aspect, a method provided herein causes mortality of an arthropod within 1 day of providing a miticide. In an aspect, a method provided herein causes mortality of an arthropod within 2 days of providing a miticide. In an aspect, a method provided herein causes mortality of an arthropod within 3 days of providing a miticide. In an aspect, a method provided herein causes mortality of an arthropod within 4 days of providing a miticide. In an aspect, a method provided herein causes mortality of an arthropod within 5 days of providing a miticide. In an aspect, a method provided herein causes mortality of an arthropod within 6 days of providing a miticide. In an aspect, a method provided herein causes mortality of an arthropod within 7 days of providing a miticide. In an aspect, a method provided herein causes mortality of an arthropod within 8 days of providing a miticide. In an aspect, a method provided herein causes mortality of an arthropod within 9 days of providing a miticide. In an aspect, a method provided herein causes mortality of an arthropod within 10 days of providing a miticide. In an aspect, a method provided herein causes mortality of an arthropod within 11 days of providing a miticide. In an aspect, a method provided herein causes mortality of an arthropod within 12 days of providing a miticide. In an aspect, a method provided herein causes mortality of an arthropod within 13 days of providing a miticide. In an aspect, a method provided herein causes mortality of an arthropod within 14 days of providing a miticide. In an aspect, a method provided herein causes mortality of an arthropod within 15 days of providing a miticide. In an aspect, a method provided herein causes mortality of an arthropod within 20 days of providing a miticide. In an aspect, a method provided herein causes mortality of an arthropod within 25 days of providing a miticide. In an aspect, a method provided herein causes mortality of an arthropod within 30 days of providing a miticide.

In an aspect, a method provided herein causes mortality of an arthropod within 1 day of providing an agent to control mites. In an aspect, a method provided herein causes mortality of an arthropod within 2 days of providing an agent to control mites. In an aspect, a method provided herein causes mortality of an arthropod within 3 days of providing an agent to control mites. In an aspect, a method provided herein causes mortality of an arthropod within 4 days of providing an agent to control mites. In an aspect, a method provided herein causes mortality of an arthropod within 5 days of providing an agent to control mites. In an aspect, a method provided herein causes mortality of an arthropod within 6 days of providing an agent to control mites. In an aspect, a method provided herein causes mortality of an arthropod within 7 days of providing an agent to control mites. In an aspect, a method provided herein causes mortality of an arthropod within 8 days of providing an agent to control mites. In an aspect, a method provided herein causes mortality of an arthropod within 9 days of providing an agent to control mites. In an aspect, a method provided herein causes mortality of an arthropod within 10 days of providing an agent to control mites. In an aspect, a method provided herein causes mortality of an arthropod within 11 days of providing an agent to control mites. In an aspect, a method provided herein causes mortality of an arthropod within 12 days of providing an agent to control mites. In an aspect, a method provided herein causes mortality of an arthropod within 13 days of providing an agent to control mites. In an aspect, a method provided herein causes mortality of an arthropod within 14 days of providing an agent to control mites. In an aspect, a method provided herein causes mortality of an arthropod within 15 days of providing an agent to control mites. In an aspect, a method provided herein causes mortality of an arthropod within 20 days of providing an agent to control mites. In an aspect, a method provided herein causes mortality of an arthropod within 25 days of providing an agent to control mites. In an aspect, a method provided herein causes mortality of an arthropod within 30 days of providing an agent to control mites.

In an aspect, a method provided herein causes mortality of a mite within 1 day of providing a miticide. In an aspect, a method provided herein causes mortality of a mite within 2 days of providing a miticide. In an aspect, a method provided herein causes mortality of a mite within 3 days of providing a miticide. In an aspect, a method provided herein causes mortality of a mite within 4 days of providing a miticide. In an aspect, a method provided herein causes mortality of a mite within 5 days of providing a miticide. In an aspect, a method provided herein causes mortality of a mite within 6 days of providing a miticide. In an aspect, a method provided herein causes mortality of a mite within 7 days of providing a miticide. In an aspect, a method provided herein causes mortality of a mite within 8 days of providing a miticide. In an aspect, a method provided herein causes mortality of a mite within 9 days of providing a miticide. In an aspect, a method provided herein causes mortality of a mite within 10 days of providing a miticide. In an aspect, a method provided herein causes mortality of a mite within 11 days of providing a miticide. In an aspect, a method provided herein causes mortality of a mite within 12 days of providing a miticide. In an aspect, a method provided herein causes mortality of a mite within 13 days of providing a miticide. In an aspect, a method provided herein causes mortality of a mite within 14 days of providing a miticide. In an aspect, a method provided herein causes mortality of a mite within 15 days of providing a miticide. In an aspect, a method provided herein causes mortality of a mite within 20 days of providing a miticide. In an aspect, a method provided herein causes mortality of a mite within 25 days of providing a miticide. In an aspect, a method provided herein causes mortality of a mite within 30 days of providing a miticide. In an aspect, a method provided herein causes mortality of a mite within 1 day of providing an agent to control mites. In an aspect, a method provided herein causes mortality of a mite within 2 days of providing an agent to control mites. In an aspect, a method provided herein causes mortality of a mite within 3 days of providing an agent to control mites. In an aspect, a method provided herein causes mortality of a mite within 4 days of providing an agent to control mites. In an aspect, a method provided herein causes mortality of a mite within 5 days of providing an agent to control mites. In an aspect, a method provided herein causes mortality of a mite within 6 days of providing an agent to control mites. In an aspect, a method provided herein causes mortality of a mite within 7 days of providing an agent to control mites. In an aspect, a method provided herein causes mortality of a mite within 8 days of providing an agent to control mites. In an aspect, a method provided herein causes mortality of a mite within 9 days of providing an agent to control mites. In an aspect, a method provided herein causes mortality of a mite within 10 days of providing an agent to control mites. In an aspect, a method provided herein causes mortality of a mite within 11 days of providing an agent to control mites. In an aspect, a method provided herein causes mortality of a mite within 12 days of providing an agent to control mites. In an aspect, a method provided herein causes mortality of a mite within 13 days of providing an agent to control mites. In an aspect, a method provided herein causes mortality of a mite within 14 days of providing an agent to control mites. In an aspect, a method provided herein causes mortality of a mite within 15 days of providing an agent to control mites. In an aspect, a method provided herein causes mortality of a mite within 20 days of providing an agent to control mites. In an aspect, a method provided herein causes mortality of a mite within 25 days of providing an agent to control mites. In an aspect, a method provided herein causes mortality of a mite within 30 days of providing an agent to control mites.

In an aspect, a method provided herein causes mortality of a *Varroa destructor* mite within 1 day of providing a miticide. In an aspect, a method provided herein causes mortality of a *Varroa destructor* mite within 2 days of providing a miticide. In an aspect, a method provided herein causes mortality of a *Varroa destructor* mite within 3 days of providing a miticide. In an aspect, a method provided herein causes mortality of a *Varroa destructor* mite within 4 days of providing a miticide. In an aspect, a method provided herein causes mortality of a *Varroa destructor* mite within 5 days of providing a miticide. In an aspect, a method provided herein causes mortality of a *Varroa destructor* mite within 6 days of providing a miticide. In an aspect, a method provided herein causes mortality of a *Varroa destructor* mite within 7 days of providing a miticide. In an aspect, a method provided herein causes mortality of a *Varroa destructor* mite within 8 days of providing a miticide. In an aspect, a method provided herein causes mortality of a *Varroa destructor* mite within 9 days of providing a miticide. In an aspect, a method provided herein causes mortality of a *Varroa destructor* mite within 10 days of providing a miticide. In an aspect, a method provided herein causes mortality of a *Varroa destructor* mite within 11 days of providing a miticide. In an aspect, a method provided herein causes mortality of a *Varroa destructor* mite within 12 days of providing a miticide. In an aspect, a method provided herein causes mortality of a *Varroa destructor* mite within 13 days of providing a miticide. In an aspect, a method provided herein causes mortality of a *Varroa destructor* mite within 14 days of providing a miticide. In an aspect, a method provided herein causes mortality of a *Varroa destructor* mite within 15 days of providing a miticide. In an aspect, a method provided herein causes mortality of a *Varroa destructor* mite within 20 days of providing a miticide. In an aspect, a method provided herein causes mortality of a *Varroa destructor* mite within 25 days of providing a miticide. In an aspect, a method provided herein causes mortality of a *Varroa destructor* mite within 30 days of providing a miticide.

In an aspect, a method provided herein causes mortality of a *Varroa destructor* mite within 1 day of providing an agent to control mites. In an aspect, a method provided herein causes mortality of a *Varroa destructor* mite within 2 days of providing an agent to control mites. In an aspect, a method provided herein causes mortality of a *Varroa destructor* mite within 3 days of providing an agent to control mites. In an aspect, a method provided herein causes mortality of a *Varroa destructor* mite within 4 days of providing an agent to control mites. In an aspect, a method provided herein causes mortality of a *Varroa destructor* mite within 5 days of providing an agent to control mites. In an aspect, a method provided herein causes mortality of a *Varroa destructor* mite within 6 days of providing an agent to control mites. In an aspect, a method provided herein causes mortality of a *Varroa destructor* mite within 7 days of providing an agent to control mites. In an aspect, a method provided herein causes mortality of a *Varroa destructor* mite within 8 days of providing an agent to control mites. In an aspect, a method provided herein causes mortality of a *Varroa destructor* mite within 9 days of providing an agent to control mites. In an aspect, a method provided herein causes mortality of a *Varroa destructor* mite within 10 days of providing an agent to control mites. In an aspect, a method provided herein causes mortality of a *Varroa destructor* mite within 11 days of providing an agent to control mites. In an aspect, a method provided herein causes mortality of a *Varroa destructor* mite within 12 days of providing an agent to control mites. In an aspect, a method provided herein causes mortality of a *Varroa destructor* mite within 13 days of providing an agent to control mites. In an aspect, a method provided herein causes mortality of a *Varroa destructor* mite within 14 days of providing an agent to control mites. In an aspect, a method provided herein causes mortality of a *Varroa destructor* mite within 15 days of providing an agent to control mites. In an aspect, a method provided herein causes mortality of a *Varroa destructor* mite within 20 days of providing an agent to control mites. In an aspect, a method provided herein causes mortality of a *Varroa destructor* mite within 25 days of providing an agent to control mites. In an aspect, a method provided herein causes mortality of a *Varroa destructor* mite within 30 days of providing an agent to control mites.

As used herein, an "agent to control mites" refers to any composition that can be used to cause mortality or stunting of a mite, reduce the reproductive rate or success of a mite, reduce the feeding frequency or duration of a mite, reduce the mobility of a mite, disrupt the rest pattern of a mite, perturb the life cycle of a mite, prevent or slow molting of a mite, or any combination thereof. In an aspect, an agent to control mites comprises a miticide. In an aspect, an agent to control mites comprises an essential oil. In an aspect, an agent to control mites comprises a non-selective organic acid. In an aspect, an agent to control mites comprises an aqueous solution. In another aspect, an agent to control mites comprises a liquid. In another aspect, an agent to control mites comprises a powder.

As used herein, a "miticide" refers to any chemical agent that is injurious or lethal to a mite. A miticide can cause mortality of a mite; reduce the lifespan of a mite; reduce or eliminate the reproductive capabilities of a mite; or any combination thereof. Non-limiting examples of miticides include Apivar® (amitraz), Apistan® (fluvalinate), CheckMite+® (coumaphos), Hivastan® (fenpyroximate), Sucrocide®, Apiguard®/Thymovar® (thymol), ApiLife Var®, Mite-Away Quick Strips® (formic acid), formic acid, oxalic acid, and HopGuard® II (hops beta acids). In an aspect, a miticide provided herein is selected from the group consisting of Apivar® (amitraz), Apistan® (fluvalinate), CheckMite+® (coumaphos), Hivastan® (fenpyroximate), Sucrocide®, Apiguard®/Thymovar® (thymol), ApiLife Var®, Mite-Away Quick Strips® (formic acid), formic acid, oxalic acid, and HopGuard® II (hops beta acids).

Bee colonies in temperate regions typically undergo changes in their population size as the year progresses. In winter, bee colonies reduce their metabolism, referred to as the "dormant phase," and few to no new offspring are being produced. As spring begins, the bee population increases exponentially (the "population increase phase") before peaking (the "population peak phase") sometime during the summer. As autumn approaches, the population of the colony declines (the "population decline phase)" before returning once again to the dormant phase in winter. Those in the art will appreciate that these phases can be skewed, depending on geographic location and environmental factors, such that the population peak phase could occur in spring or autumn, and that the population decline phase could begin in winter, and the population phases are not tied to particular seasons or months of the year.

These phases can also be skewed by honey flow. As used herein, "honey flow" refers to a time period when one or more major nectar sources in bloom and the weather is favorable for bees to fly and collect nectar in abundance. Depending on the geographic location and local climate, honey flow can peak in the spring, summer, or autumn. Honey flow can last anywhere from a few days to many weeks. In one aspect, honey flow occurs during spring. In another aspect, honey flow occurs during summer. In a further aspect, honey flow occurs during autumn. In an aspect, honey flow comprises at least 2 days. In another aspect, honey flow comprises at least 3 days. In another aspect, honey flow comprises at least 5 days. In another aspect, honey flow comprises at least 2 weeks. In another aspect, honey flow comprises at least 3 weeks. In another aspect, honey flow comprises at least 4 weeks. In another aspect, honey flow comprises at least 5 weeks. In another aspect, honey flow comprises at least 6 weeks. In another aspect, honey flow comprises at least 7 weeks. In another aspect, honey flow comprises at least 8 weeks. In another aspect, honey flow comprises at least 9 weeks. In another aspect, honey flow comprises at least 10 weeks. In another aspect, honey flow comprises at least 11 weeks. In another aspect, honey flow comprises at least 12 weeks.

In an aspect, honey flow overlaps with the population increase phase of a hive. In another aspect, honey flow overlaps with the population peak phase of a hive.

In an aspect, a beehive or bee colony experiences at least one honey flow period between two consecutive dormant phases. In another aspect, a beehive or bee colony experiences at least two honey flow periods between two consecutive dormant phases. In another aspect, a beehive or bee colony experiences at least three honey flow periods between two consecutive dormant phases. In another aspect, a beehive or bee colony experiences at least four honey flow periods between two consecutive dormant phases. In another aspect, a beehive or bee colony experiences at least five honey flow periods between two consecutive dormant phases.

In an aspect, a composition provided herein is provided to a beehive or bee colony during the dormant phase of the beehive or bee colony life cycle. In an aspect, an agent to control mites provided herein is provided to a beehive or bee colony during the dormant phase of the beehive or bee colony life cycle. In an aspect, a miticide provided herein is provided to a beehive or bee colony during the dormant phase of the beehive or bee colony life cycle. In an aspect, a nucleic acid molecule provided herein is provided to a beehive or bee colony during the dormant phase of the beehive or bee colony life cycle. In an aspect, a dsRNA provided herein is provided to a beehive or bee colony during the dormant phase of the beehive or bee colony life cycle. In an aspect, a dsRNA provided herein is provided to a beehive or bee colony during honey flow and an agent to control mites provided herein is provided to the beehive or bee colony during the dormant phase of the beehive or bee colony life cycle.

In an aspect, a composition provided herein is provided to a beehive or bee colony during the population increase phase of the beehive or bee colony life cycle. In an aspect, an agent to control mites provided herein is provided to a beehive or bee colony during the population increase phase of the beehive or bee colony life cycle. In an aspect, a miticide provided herein is provided to a beehive or bee colony during the population increase phase of the beehive or bee colony life cycle. In an aspect, a nucleic acid molecule provided herein is provided to a beehive or bee colony during the population increase phase of the beehive or bee colony life cycle. In an aspect, a dsRNA provided herein is provided to a beehive or bee colony during the population increase phase of the beehive or bee colony life cycle.

In an aspect, a composition provided herein is provided to a beehive or bee colony during the population peak phase of the beehive or bee colony life cycle. In an aspect, an agent to control mites provided herein is provided to a beehive or bee colony during the population peak phase of the beehive or bee colony life cycle. In an aspect, a miticide provided herein is provided to a beehive or bee colony during the population peak phase of the beehive or bee colony life cycle. In an aspect, a nucleic acid molecule provided herein is provided to a beehive or bee colony during the population peak phase of the beehive or bee colony life cycle. In an aspect, a dsRNA provided herein is provided to a beehive or bee colony during the population peak phase of the beehive or bee colony life cycle.

In an aspect, a composition provided herein is provided to a beehive or bee colony during the population decrease phase of the beehive or bee colony life cycle. In an aspect, an agent to control mites provided herein is provided to a beehive or bee colony during the population decrease phase of the beehive or bee colony life cycle. In an aspect, a miticide provided herein is provided to a beehive or bee colony during the population decrease phase of the beehive or bee colony life cycle. In an aspect, a nucleic acid molecule provided herein is provided to a beehive or bee colony during the population decrease phase of the beehive or bee colony life cycle. In an aspect, a dsRNA provided herein is provided to a beehive or bee colony during the population decrease phase of the beehive or bee colony life cycle.

In an aspect, a composition provided herein is provided to a beehive or bee colony before a honey flow period. In an aspect, an agent to control mites provided herein is provided to a beehive or bee colony before a honey flow period. In an aspect, a miticide provided herein is provided to a beehive or bee colony before a honey flow period. In an aspect, a nucleic acid molecule provided herein is provided to a beehive or bee colony before a honey flow period. In an aspect, a dsRNA provided herein is provided to a beehive or bee colony before a honey flow period. In an aspect, a composition provided herein is provided to a beehive or bee colony during a honey flow period. In an aspect, a nucleic acid molecule provided herein is provided to a beehive or bee colony during a honey flow period. In an aspect, a dsRNA provided herein is provided to a beehive or bee colony during a honey flow period. In an aspect, a composition provided herein is provided to a beehive or bee colony after a honey flow period. In an aspect, an agent to control mites provided herein is provided to a beehive or bee colony after a honey flow period. In an aspect, a miticide provided herein is provided to a beehive or bee colony after a honey flow period. In an aspect, a nucleic acid molecule provided herein is provided to a beehive or bee colony after a honey flow period. In an aspect, a dsRNA provided herein is provided to a beehive or bee colony after a honey flow period.

In an aspect, a composition provided herein is provided to a beehive or bee colony when the ratio of *Varroa destructor* mites to bees in the beehive or bee colony is at least 1 *Varroa destructor* mite per 100 bees. In an aspect, a composition provided herein is provided to a beehive or bee colony when the ratio of *Varroa destructor* mites to bees in the beehive or bee colony is at least 2 *Varroa destructor* mites per 100 bees. In an aspect, a composition provided herein is provided to a beehive or bee colony when the ratio of *Varroa destructor* mites to bees in the beehive or bee colony is at least 3 *Varroa destructor* mites per 100 bees. In an aspect, a composition provided herein is provided to a beehive or bee colony when the ratio of *Varroa destructor* mites to bees in the beehive or bee colony is at least 4 *Varroa destructor* mites per 100 bees. In an aspect, a composition provided herein is provided to a beehive or bee colony when the ratio of *Varroa destructor* mites to bees in the beehive or bee colony is at least 5 *Varroa destructor* mites per 100 bees. In an aspect, a composition provided herein is provided to a beehive or bee colony when the ratio of *Varroa destructor* mites to bees in the beehive or bee colony is at least 6 *Varroa destructor* mites per 100 bees. In an aspect, a composition provided herein is provided to a beehive or bee colony when the ratio of *Varroa destructor* mites to bees in the beehive or bee colony is at least 7 *Varroa destructor* mites per 100 bees. In an aspect, a composition provided herein is provided to a beehive or bee colony when the ratio of *Varroa destructor* mites to bees in the beehive or bee colony is at least 8 *Varroa destructor* mites per 100 bees. In an aspect, a composition provided herein is provided to a beehive or bee colony when the ratio of *Varroa destructor* mites to bees in the beehive or bee colony is at least 9 *Varroa destructor* mites per 100 bees. In an aspect, a composition provided herein is provided to a beehive or bee colony when the ratio of *Varroa destructor* mites to bees in the beehive or bee colony is at least 10 *Varroa destructor* mites per 100 bees.

In an aspect, a miticide provided herein is provided to a beehive or bee colony when the ratio of *Varroa destructor* mites to bees in the beehive or bee colony is at least 1 *Varroa destructor* mite per 100 bees. In an aspect, a miticide provided herein is provided to a beehive or bee colony when the ratio of *Varroa destructor* mites to bees in the beehive or bee colony is at least 2 *Varroa destructor* mites per 100 bees. In an aspect, a miticide provided herein is provided to a beehive or bee colony when the ratio of *Varroa destructor* mites to bees in the beehive or bee colony is at least 3 *Varroa destructor* mites per 100 bees. In an aspect, a miticide provided herein is provided to a beehive or bee colony when the ratio of *Varroa destructor* mites to bees in the beehive or bee colony is at least 4 *Varroa destructor* mites per 100 bees. In an aspect, a miticide provided herein is provided to a beehive or bee colony when the ratio of *Varroa destructor* mites to bees in the beehive or bee colony is at least 5 *Varroa destructor* mites per 100 bees. In an aspect, a miticide provided herein is provided to a beehive or bee colony when the ratio of *Varroa destructor* mites to bees in the beehive or bee colony is at least 6 *Varroa destructor* mites per 100 bees. In an aspect, a miticide provided herein is provided to a beehive or bee colony when the ratio of *Varroa destructor* mites to bees in the beehive or bee colony is at least 7 *Varroa destructor* mites per 100 bees. In an aspect, a miticide provided herein is provided to a beehive or bee colony when the ratio of *Varroa destructor* mites to bees in the beehive or bee colony is at least 8 *Varroa destructor* mites per 100 bees. In an aspect, a miticide provided herein is provided to a beehive or bee colony when the ratio of *Varroa destructor* mites to bees in the beehive or bee colony is at least 9 *Varroa destructor* mites per 100 bees. In an aspect, a miticide provided herein is provided to a beehive or bee colony when the ratio of *Varroa destructor* mites to bees in the beehive or bee colony is at least 10 *Varroa destructor* mites per 100 bees.

In an aspect, an agent to control mites provided herein is provided to a beehive or bee colony when the ratio of *Varroa destructor* mites to bees in the beehive or bee colony is at least 1 *Varroa destructor* mite per 100 bees. In an aspect, an agent to control mites provided herein is provided to a beehive or bee colony when the ratio of *Varroa destructor* mites to bees in the beehive or bee colony is at least 2 *Varroa destructor* mites per 100 bees. In an aspect, an agent to control mites provided herein is provided to a beehive or bee colony when the ratio of *Varroa destructor* mites to bees in the beehive or bee colony is at least 3 *Varroa destructor* mites per 100 bees. In an aspect, an agent to control mites provided herein is provided to a beehive or bee colony when the ratio of *Varroa destructor* mites to bees in the beehive or bee colony is at least 4 *Varroa destructor* mites per 100 bees. In an aspect, an agent to control mites provided herein is provided to a beehive or bee colony when the ratio of *Varroa destructor* mites to bees in the beehive or bee colony is at least 5 *Varroa destructor* mites per 100 bees. In an aspect, an agent to control mites provided herein is provided to a beehive or bee colony when the ratio of *Varroa destructor* mites to bees in the beehive or bee colony is at least 6 *Varroa destructor* mites per 100 bees. In an aspect, an agent to control mites provided herein is provided to a beehive or bee colony when the ratio of *Varroa destructor* mites to bees in the beehive or bee colony is at least 7 *Varroa destructor* mites per 100 bees. In an aspect, an agent to control mites provided herein is provided to a beehive or bee colony when the ratio of *Varroa destructor* mites to bees in the beehive or bee colony is at least 8 *Varroa destructor* mites per 100 bees. In an aspect, an agent to control mites provided herein is provided to a beehive or bee colony when the ratio of *Varroa destructor* mites to bees in the beehive or bee colony is at least 9 *Varroa destructor* mites per 100 bees. In an aspect, an agent to control mites provided herein is provided to a beehive or bee colony when the ratio of *Varroa destructor* mites to bees in the beehive or bee colony is at least 10 *Varroa destructor* mites per 100 bees.

In an aspect, a nucleic acid molecule provided herein is provided to a beehive or bee colony when the ratio of *Varroa destructor* mites to bees in the beehive or bee colony is at least 1 *Varroa destructor* mite per 100 bees. In an aspect, a nucleic acid molecule provided herein is provided to a beehive or bee colony when the ratio of *Varroa destructor* mites to bees in the beehive or bee colony is at least 2 *Varroa destructor* mites per 100 bees. In an aspect, a nucleic acid molecule provided herein is provided to a beehive or bee colony when the ratio of *Varroa destructor* mites to bees in the beehive or bee colony is at least 3 *Varroa destructor* mites per 100 bees. In an aspect, a nucleic acid molecule provided herein is provided to a beehive or bee colony when the ratio of *Varroa destructor* mites to bees in the beehive or bee colony is at least 4 *Varroa destructor* mites per 100 bees. In an aspect, a nucleic acid molecule provided herein is provided to a beehive or bee colony when the ratio of *Varroa destructor* mites to bees in the beehive or bee colony is at least 5 *Varroa destructor* mites per 100 bees. In an aspect, a nucleic acid molecule provided herein is provided to a beehive or bee colony when the ratio of *Varroa destructor* mites to bees in the beehive or bee colony is at least 6 *Varroa destructor* mites per 100 bees. In an aspect, a nucleic acid molecule provided herein is provided to a beehive or bee colony when the ratio of *Varroa destructor* mites to bees in the beehive or bee colony is at least 7 *Varroa destructor* mites per 100 bees. In an aspect, a nucleic acid molecule provided herein is provided to a beehive or bee colony when the ratio of *Varroa destructor* mites to bees in the beehive or bee colony is at least 8 *Varroa destructor* mites per 100 bees. In an aspect, a nucleic acid molecule provided herein is provided to a beehive or bee colony when the ratio of *Varroa destructor* mites to bees in the beehive or bee colony is at least 9 *Varroa destructor* mites per 100 bees. In an aspect, a nucleic acid molecule provided herein is provided to a beehive or bee colony when the ratio of *Varroa destructor* mites to bees in the beehive or bee colony is at least 10 *Varroa destructor* mites per 100 bees.

In an aspect, a dsRNA provided herein is provided to a beehive or bee colony when the ratio of *Varroa destructor* mites to bees in the beehive or bee colony is at least 1 *Varroa destructor* mite per 100 bees. In an aspect, a dsRNA provided herein is provided to a beehive or bee colony when the ratio of *Varroa destructor* mites to bees in the beehive or bee colony is at least 2 *Varroa destructor* mites per 100 bees. In an aspect, a dsRNA provided herein is provided to a beehive or bee colony when the ratio of *Varroa destructor* mites to bees in the beehive or bee colony is at least 3 *Varroa destructor* mites per 100 bees. In an aspect, a dsRNA provided herein is provided to a beehive or bee colony when the ratio of *Varroa destructor* mites to bees in the beehive or bee colony is at least 4 *Varroa destructor* mites per 100 bees. In an aspect, a dsRNA provided herein is provided to a beehive or bee colony when the ratio of *Varroa destructor* mites to bees in the beehive or bee colony is at least 5 *Varroa destructor* mites per 100 bees. In an aspect, a dsRNA provided herein is provided to a beehive or bee colony when the ratio of *Varroa destructor* mites to bees in the beehive or bee colony is at least 6 *Varroa destructor* mites per 100 bees. In an aspect, a dsRNA provided herein is provided to a beehive or bee colony when the ratio of *Varroa destructor* mites to bees in the beehive or bee colony is at least 7 *Varroa destructor* mites per 100 bees. In an aspect, a dsRNA provided herein is provided to a beehive or bee colony when the ratio of *Varroa destructor* mites to bees in the beehive or bee colony is at least 8 *Varroa destructor* mites per 100 bees. In an aspect, a dsRNA provided herein is provided to a beehive or bee colony when the ratio of *Varroa destructor* mites to bees in the beehive or bee colony is at least 9 *Varroa destructor* mites per 100 bees. In an aspect, a dsRNA provided herein is provided to a beehive or bee colony when the ratio of *Varroa destructor* mites to bees in the beehive or bee colony is at least 10 *Varroa destructor* mites per 100 bees.

In an aspect, a composition comprising a nucleic acid molecule and a miticide are provided to a beehive or bee colony on the same day. In an aspect, a composition comprising a nucleic acid molecule and a miticide are provided to an arthropod on the same day. In an aspect, a composition comprising a nucleic acid molecule and a miticide are provided to a mite on the same day. In an aspect, a composition comprising a nucleic acid molecule and a miticide are provided to a *Varroa destructor* mite on the same day.

In an aspect, a composition comprising a nucleic acid molecule and an agent to control mites are provided to a beehive or bee colony on the same day. In an aspect, a composition comprising a nucleic acid molecule and an agent to control mites are provided to an arthropod on the same day. In an aspect, a composition comprising a nucleic acid molecule and an agent to control mites are provided to a mite on the same day. In an aspect, a composition comprising a nucleic acid molecule and an agent to control mites are provided to a *Varroa destructor* mite on the same day.

In an aspect, a composition comprising a nucleic acid molecule is provided to a beehive or bee colony before a miticide is provided to the beehive or bee colony. In an aspect, a composition comprising a nucleic acid molecule is provided to an arthropod before a miticide is provided to the arthropod. In an aspect, a composition comprising a nucleic acid molecule is provided to a mite before a miticide is provided to the mite. In an aspect, a composition comprising a nucleic acid molecule is provided to a *Varroa destructor* mite before a miticide is provided to the *Varroa destructor* mite.

In an aspect, a composition comprising a nucleic acid molecule is provided to a beehive or bee colony before an agent to control mites is provided to the beehive or bee colony. In an aspect, a composition comprising a nucleic acid molecule is provided to an arthropod before an agent to control mites is provided to the arthropod. In an aspect, a composition comprising a nucleic acid molecule is provided to a mite before an agent to control mites is provided to the mite. In an aspect, a composition comprising a nucleic acid molecule is provided to a *Varroa destructor* mite before an agent to control mites is provided to the *Varroa destructor* mite.

In an aspect, a miticide is provided to a beehive or bee colony before a composition comprising a nucleic acid molecule is provided to the beehive or bee colony. In an aspect, a miticide is provided to an arthropod before a composition comprising a nucleic acid molecule is provided to the arthropod. In an aspect, a miticide is provided to a mite before a composition comprising a nucleic acid molecule is provided to the mite. In an aspect, a miticide is provided to a *Varroa destructor* mite before a composition comprising a nucleic acid molecule is provided to the *Varroa destructor* mite.

In an aspect, an agent to control mites is provided to a beehive or bee colony before a composition comprising a nucleic acid molecule is provided to the beehive or bee colony. In an aspect, an agent to control mites is provided to an arthropod before a composition comprising a nucleic acid molecule is provided to the arthropod. In an aspect, an agent to control mites is provided to a mite before a composition comprising a nucleic acid molecule is provided to the mite. In an aspect, an agent to control mites is provided to a *Varroa destructor* mite before a composition comprising a nucleic acid molecule is provided to the *Varroa destructor* mite.

In an aspect, a composition comprising a nucleic acid molecule and a miticide are provided to a beehive or a bee colony at least 1 day apart. In an aspect, a composition comprising a nucleic acid molecule and a miticide are provided to a beehive or a bee colony at least 2 days apart. In an aspect, a composition comprising a nucleic acid molecule and a miticide are provided to a beehive or a bee colony at least 3 days apart. In an aspect, a composition comprising a nucleic acid molecule and a miticide are provided to a beehive or a bee colony at least 4 days apart. In an aspect, a composition comprising a nucleic acid molecule and a miticide are provided to a beehive or a bee colony at least 5 days apart. In an aspect, a composition comprising a nucleic acid molecule and a miticide are provided to a beehive or a bee colony at least 6 days apart. In an aspect, a composition comprising a nucleic acid molecule and a miticide are provided to a beehive or a bee colony at least 7 days apart. In an aspect, a composition comprising a nucleic acid molecule and a miticide are provided to a beehive or a bee colony at least 8 days apart. In an aspect, a composition comprising a nucleic acid molecule and a miticide are provided to a beehive or a bee colony at least 9 days apart. In an aspect, a composition comprising a nucleic acid molecule and a miticide are provided to a beehive or a bee colony at least 10 days apart. In an aspect, a composition comprising a nucleic acid molecule and a miticide are provided to a beehive or a bee colony at least 11 days apart. In an aspect, a composition comprising a nucleic acid molecule and a miticide are provided to a beehive or a bee colony at least 12 days apart. In an aspect, a composition comprising a nucleic acid molecule and a miticide are provided to a beehive or a bee colony at least 13 days apart. In an aspect, a composition comprising a nucleic acid molecule and a miticide are provided to a beehive or a bee colony at least 14 days apart. In an aspect, a composition comprising a nucleic acid molecule and a miticide are provided to a beehive or a bee colony at least 15 days apart. In an aspect, a composition comprising a nucleic acid molecule and a miticide are provided to a beehive or a bee colony at least 20 days apart. In an aspect, a composition comprising a nucleic acid molecule and a miticide are provided to a beehive or a bee colony at least 25 days apart. In an aspect, a composition comprising a nucleic acid molecule and a miticide are provided to a beehive or a bee colony at least 30 days apart. In an aspect, a composition comprising a nucleic acid molecule and a miticide are provided to a beehive or a bee colony at least 45 days apart. In an aspect, a composition comprising a nucleic acid molecule and a miticide are provided to a beehive or a bee colony at least 60 days apart. In an aspect, a composition comprising a nucleic acid molecule and a miticide are provided to a beehive or a bee colony at least 90 days apart. In an aspect, a composition comprising a nucleic acid molecule and a miticide are provided to a beehive or a bee colony at least 120 days apart. In an aspect, a composition comprising a nucleic acid molecule and a miticide are provided to a beehive or a bee colony at least 150 days apart. In an aspect, a composition comprising a nucleic acid molecule and a miticide are provided to a beehive or a bee colony at least 180 days apart.

In an aspect, a composition comprising a nucleic acid molecule and an agent to control mites are provided to a beehive or a bee colony at least 1 day apart. In an aspect, a composition comprising a nucleic acid molecule and an agent to control mites are provided to a beehive or a bee colony at least 2 days apart. In an aspect, a composition comprising a nucleic acid molecule and an agent to control mites are provided to a beehive or a bee colony at least 3 days apart. In an aspect, a composition comprising a nucleic acid molecule and an agent to control mites are provided to a beehive or a bee colony at least 4 days apart. In an aspect, a composition comprising a nucleic acid molecule and an agent to control mites are provided to a beehive or a bee colony at least 5 days apart. In an aspect, a composition comprising a nucleic acid molecule and an agent to control mites are provided to a beehive or a bee colony at least 6 days apart. In an aspect, a composition comprising a nucleic acid molecule and an agent to control mites are provided to a beehive or a bee colony at least 7 days apart. In an aspect, a composition comprising a nucleic acid molecule and an agent to control mites are provided to a beehive or a bee colony at least 8 days apart. In an aspect, a composition comprising a nucleic acid molecule and an agent to control mites are provided to a beehive or a bee colony at least 9 days apart. In an aspect, a composition comprising a nucleic acid molecule and an agent to control mites are provided to a beehive or a bee colony at least 10 days apart. In an aspect, a composition comprising a nucleic acid molecule and an agent to control mites are provided to a beehive or a bee colony at least 11 days apart. In an aspect, a composition comprising a nucleic acid molecule and an agent to control mites are provided to a beehive or a bee colony at least 12 days apart. In an aspect, a composition comprising a nucleic acid molecule and an agent to control mites are provided to a beehive or a bee colony at least 13 days apart. In an aspect, a composition comprising a nucleic acid molecule and an agent to control mites are provided to a beehive or a bee colony at least 14 days apart. In an aspect, a composition comprising a nucleic acid molecule and an agent to control mites are provided to a beehive or a bee colony at least 15 days apart. In an aspect, a composition comprising a nucleic acid molecule and an agent to control mites are provided to a beehive or a bee colony at least 20 days apart. In an aspect, a composition comprising a nucleic acid molecule and an agent to control mites are provided to a beehive or a bee colony at least 25 days apart. In an aspect, a composition comprising a nucleic acid molecule and an agent to control mites are provided to a beehive or a bee colony at least 30 days apart. In an aspect, a composition comprising a nucleic acid molecule and an agent to control mites are provided to a beehive or a bee colony at least 45 days apart. In an aspect, a composition comprising a nucleic acid molecule and an agent to control mites are provided to a beehive or a bee colony at least 60 days apart. In an aspect, a composition comprising a nucleic acid molecule and an agent to control mites are provided to a beehive or a bee colony at least 90 days apart. In an aspect, a composition comprising a nucleic acid molecule and an agent to control mites are provided to a beehive or a bee colony at least 120 days apart. In an aspect, a composition comprising a nucleic acid molecule and an agent to control mites are provided to a beehive or a bee colony at least 150 days apart. In an aspect, a composition comprising a nucleic acid molecule and an agent to control mites are provided to a beehive or a bee colony at least 180 days apart.

In an aspect, a composition comprising a nucleic acid molecule and a miticide are provided to an arthropod at least 1 day apart. In an aspect, a composition comprising a nucleic acid molecule and a miticide are provided to an arthropod at least 2 days apart. In an aspect, a composition comprising a nucleic acid molecule and a miticide are provided to an arthropod at least 3 days apart. In an aspect, a composition comprising a nucleic acid molecule and a miticide are provided to an arthropod at least 4 days apart. In an aspect, a composition comprising a nucleic acid molecule and a miticide are provided to an arthropod at least 5 days apart. In an aspect, a composition comprising a nucleic acid molecule and a miticide are provided to an arthropod at least 6 days apart. In an aspect, a composition comprising a nucleic acid molecule and a miticide are provided to an arthropod at least 7 days apart. In an aspect, a composition comprising a nucleic acid molecule and a miticide are provided to an arthropod at least 8 days apart. In an aspect, a composition comprising a nucleic acid molecule and a miticide are provided to an arthropod at least 9 days apart. In an aspect, a composition comprising a nucleic acid molecule and a miticide are provided to an arthropod at least 10 days apart. In an aspect, a composition comprising a nucleic acid molecule and a miticide are provided to an arthropod at least 11 days apart. In an aspect, a composition comprising a nucleic acid molecule and a miticide are provided to an arthropod at least 12 days apart. In an aspect, a composition comprising a nucleic acid molecule and a miticide are provided to an arthropod at least 13 days apart. In an aspect, a composition comprising a nucleic acid molecule and a miticide are provided to an arthropod at least 14 days apart. In an aspect, a composition comprising a nucleic acid molecule and a miticide are provided to an arthropod at least 15 days apart. In an aspect, a composition comprising a nucleic acid molecule and a miticide are provided to an arthropod at least 20 days apart. In an aspect, a composition comprising a nucleic acid molecule and a miticide are provided to an arthropod at least 25 days apart. In an aspect, a composition comprising a nucleic acid molecule and a miticide are provided to an arthropod at least 30 days apart. In an aspect, a composition comprising a nucleic acid molecule and a miticide are provided to an arthropod at least 35 days apart. In an aspect, a composition comprising a nucleic acid molecule and a miticide are provided to an arthropod at least 40 days apart. In an aspect, a composition comprising a nucleic acid molecule and a miticide are provided to an arthropod at least 45 days apart. In an aspect, a composition comprising a nucleic acid molecule and a miticide are provided to an arthropod at least 50 days apart. In an aspect, a composition comprising a nucleic acid molecule and a miticide are provided to an arthropod at least 60 days apart. In an aspect, a composition comprising a nucleic acid molecule and a miticide are provided to an arthropod at least 90 days apart. In an aspect, a composition comprising a nucleic acid molecule and a miticide are provided to an arthropod at least 120 days apart. In an aspect, a composition comprising a nucleic acid molecule and a miticide are provided to an arthropod at least 150 days apart. In an aspect, a composition comprising a nucleic acid molecule and a miticide are provided to an arthropod at least 180 days apart.

In an aspect, a composition comprising a nucleic acid molecule and an agent to control mites are provided to an arthropod at least 1 day apart. In an aspect, a composition comprising a nucleic acid molecule and an agent to control mites are provided to an arthropod at least 2 days apart. In an aspect, a composition comprising a nucleic acid molecule and an agent to control mites are provided to an arthropod at least 3 days apart. In an aspect, a composition comprising a nucleic acid molecule and an agent to control mites are provided to an arthropod at least 4 days apart. In an aspect, a composition comprising a nucleic acid molecule and an agent to control mites are provided to an arthropod at least 5 days apart. In an aspect, a composition comprising a nucleic acid molecule and an agent to control mites are provided to an arthropod at least 6 days apart. In an aspect, a composition comprising a nucleic acid molecule and an agent to control mites are provided to an arthropod at least 7 days apart. In an aspect, a composition comprising a nucleic acid molecule and an agent to control mites are provided to an arthropod at least 8 days apart. In an aspect, a composition comprising a nucleic acid molecule and an agent to control mites are provided to an arthropod at least 9 days apart. In an aspect, a composition comprising a nucleic acid molecule and an agent to control mites are provided to an arthropod at least 10 days apart. In an aspect, a composition comprising a nucleic acid molecule and an agent to control mites are provided to an arthropod at least 11 days apart. In an aspect, a composition comprising a nucleic acid molecule and an agent to control mites are provided to an arthropod at least 12 days apart. In an aspect, a composition comprising a nucleic acid molecule and an agent to control mites are provided to an arthropod at least 13 days apart. In an aspect, a composition comprising a nucleic acid molecule and an agent to control mites are provided to an arthropod at least 14 days apart. In an aspect, a composition comprising a nucleic acid molecule and an agent to control mites are provided to an arthropod at least 15 days apart. In an aspect, a composition comprising a nucleic acid molecule and an agent to control mites are provided to an arthropod at least 20 days apart. In an aspect, a composition comprising a nucleic acid molecule and an agent to control mites are provided to an arthropod at least 25 days apart. In an aspect, a composition comprising a nucleic acid molecule and an agent to control mites are provided to an arthropod at least 30 days apart. In an aspect, a composition comprising a nucleic acid molecule and an agent to control mites are provided to an arthropod at least 35 days apart. In an aspect, a composition comprising a nucleic acid molecule and an agent to control mites are provided to an arthropod at least 40 days apart. In an aspect, a composition comprising a nucleic acid molecule and an agent to control mites are provided to an arthropod at least 45 days apart. In an aspect, a composition comprising a nucleic acid molecule and an agent to control mites are provided to an arthropod at least 50 days apart. In an aspect, a composition comprising a nucleic acid molecule and an agent to control mites are provided to an arthropod at least 60 days apart. In an aspect, a composition comprising a nucleic acid molecule and an agent to control mites are provided to an arthropod at least 90 days apart. In an aspect, a composition comprising a nucleic acid molecule and an agent to control mites are provided to an arthropod at least 120 days apart. In an aspect, a composition comprising a nucleic acid molecule and an agent to control mites are provided to an arthropod at least 150 days apart. In an aspect, a composition comprising a nucleic acid molecule and an agent to control mites are provided to an arthropod at least 180 days apart.

In an aspect, a composition comprising a nucleic acid molecule and a miticide are provided to a mite at least 1 day apart. In an aspect, a composition comprising a nucleic acid molecule and a miticide are provided to a mite at least 2 days apart. In an aspect, a composition comprising a nucleic acid molecule and a miticide are provided to a mite at least 3 days apart. In an aspect, a composition comprising a nucleic acid molecule and a miticide are provided to a mite at least 4 days apart. In an aspect, a composition comprising a nucleic acid molecule and a miticide are provided to a mite at least 5 days apart. In an aspect, a composition comprising a nucleic acid molecule and a miticide are provided to a mite at least 6 days apart. In an aspect, a composition comprising a nucleic acid molecule and a miticide are provided to a mite at least 7 days apart. In an aspect, a composition comprising a nucleic acid molecule and a miticide are provided to a mite at least 8 days apart. In an aspect, a composition comprising a nucleic acid molecule and a miticide are provided to a mite at least 9 days apart. In an aspect, a composition comprising a nucleic acid molecule and a miticide are provided to a mite at least 10 days apart. In an aspect, a composition comprising a nucleic acid molecule and a miticide are provided to a mite at least 11 days apart. In an aspect, a composition comprising a nucleic acid molecule and a miticide are provided to a mite at least 12 days apart. In an aspect, a composition comprising a nucleic acid molecule and a miticide are provided to a mite at least 13 days apart. In an aspect, a composition comprising a nucleic acid molecule and a miticide are provided to a mite at least 14 days apart. In an aspect, a composition comprising a nucleic acid molecule and a miticide are provided to a mite at least 15 days apart. In an aspect, a composition comprising a nucleic acid molecule and a miticide are provided to a mite at least 20 days apart. In an aspect, a composition comprising a nucleic acid molecule and a miticide are provided to a mite at least 25 days apart. In an aspect, a composition comprising a nucleic acid molecule and a miticide are provided to a mite at least 30 days apart. In an aspect, a composition comprising a nucleic acid molecule and a miticide are provided to a mite at least 45 days apart. In an aspect, a composition comprising a nucleic acid molecule and a miticide are provided to a mite at least 60 days apart. In an aspect, a composition comprising a nucleic acid molecule and a miticide are provided to a mite at least 90 days apart. In an aspect, a composition comprising a nucleic acid molecule and a miticide are provided to a mite at least 120 days apart. In an aspect, a composition comprising a nucleic acid molecule and a miticide are provided to a mite at least 150 days apart. In an aspect, a composition comprising a nucleic acid molecule and a miticide are provided to a mite at least 180 days apart.

In an aspect, a composition comprising a nucleic acid molecule and an agent to control mites are provided to a mite at least 1 day apart. In an aspect, a composition comprising a nucleic acid molecule and an agent to control mites are provided to a mite at least 2 days apart. In an aspect, a composition comprising a nucleic acid molecule and an agent to control mites are provided to a mite at least 3 days apart. In an aspect, a composition comprising a nucleic acid molecule and an agent to control mites are provided to a mite at least 4 days apart. In an aspect, a composition comprising a nucleic acid molecule and an agent to control mites are provided to a mite at least 5 days apart. In an aspect, a composition comprising a nucleic acid molecule and an agent to control mites are provided to a mite at least 6 days apart. In an aspect, a composition comprising a nucleic acid molecule and an agent to control mites are provided to a mite at least 7 days apart. In an aspect, a composition comprising a nucleic acid molecule and an agent to control mites are provided to a mite at least 8 days apart. In an aspect, a composition comprising a nucleic acid molecule and an agent to control mites are provided to a mite at least 9 days apart. In an aspect, a composition comprising a nucleic acid molecule and an agent to control mites are provided to a mite at least 10 days apart. In an aspect, a composition comprising a nucleic acid molecule and an agent to control mites are provided to a mite at least 11 days apart. In an aspect, a composition comprising a nucleic acid molecule and an agent to control mites are provided to a mite at least 12 days apart. In an aspect, a composition comprising a nucleic acid molecule and an agent to control mites are provided to a mite at least 13 days apart. In an aspect, a composition comprising a nucleic acid molecule and an agent to control mites are provided to a mite at least 14 days apart. In an aspect, a composition comprising a nucleic acid molecule and an agent to control mites are provided to a mite at least 15 days apart. In an aspect, a composition comprising a nucleic acid molecule and an agent to control mites are provided to a mite at least 20 days apart. In an aspect, a composition comprising a nucleic acid molecule and an agent to control mites are provided to a mite at least 25 days apart. In an aspect, a composition comprising a nucleic acid molecule and an agent to control mites are provided to a mite at least 30 days apart. In an aspect, a composition comprising a nucleic acid molecule and an agent to control mites are provided to a mite at least 45 days apart. In an aspect, a composition comprising a nucleic acid molecule and an agent to control mites are provided to a mite at least 60 days apart. In an aspect, a composition comprising a nucleic acid molecule and an agent to control mites are provided to a mite at least 90 days apart. In an aspect, a composition comprising a nucleic acid molecule and an agent to control mites are provided to a mite at least 120 days apart. In an aspect, a composition comprising a nucleic acid molecule and an agent to control mites are provided to a mite at least 150 days apart. In an aspect, a composition comprising a nucleic acid molecule and an agent to control mites are provided to a mite at least 180 days apart.

In an aspect, a composition comprising a nucleic acid molecule and a miticide are provided to a *Varroa destructor* mite at least 1 day apart. In an aspect, a composition comprising a nucleic acid molecule and a miticide are provided to a *Varroa destructor* mite at least 2 days apart. In an aspect, a composition comprising a nucleic acid molecule and a miticide are provided to a *Varroa destructor* mite at least 3 days apart. In an aspect, a composition comprising a nucleic acid molecule and a miticide are provided to a *Varroa destructor* mite at least 4 days apart. In an aspect, a composition comprising a nucleic acid molecule and a miticide are provided to a *Varroa destructor* mite at least 5 days apart. In an aspect, a composition comprising a nucleic acid molecule and a miticide are provided to a *Varroa destructor* mite at least 6 days apart. In an aspect, a composition comprising a nucleic acid molecule and a miticide are provided to a *Varroa destructor* mite at least 7 days apart. In an aspect, a composition comprising a nucleic acid molecule and a miticide are provided to a *Varroa destructor* mite at least 8 days apart. In an aspect, a composition comprising a nucleic acid molecule and a miticide are provided to a *Varroa destructor* mite at least 9 days apart. In an aspect, a composition comprising a nucleic acid molecule and a miticide are provided to a *Varroa destructor* mite at least 10 days apart. In an aspect, a composition comprising a nucleic acid molecule and a miticide are provided to a *Varroa destructor* mite at least 11 days apart. In an aspect, a composition comprising a nucleic acid molecule and a miticide are provided to a *Varroa destructor* mite at least 12 days apart. In an aspect, a composition comprising a nucleic acid molecule and a miticide are provided to a *Varroa destructor* mite at least 13 days apart. In an aspect, a composition comprising a nucleic acid molecule and a miticide are provided to a *Varroa destructor* mite at least 14 days apart. In an aspect, a composition comprising a nucleic acid molecule and a miticide are provided to a *Varroa destructor* mite at least 15 days apart. In an aspect, a composition comprising a nucleic acid molecule and a miticide are provided to a *Varroa destructor* mite at least 20 days apart. In an aspect, a composition comprising a nucleic acid molecule and a miticide are provided to a *Varroa destructor* mite at least 25 days apart. In an aspect, a composition comprising a nucleic acid molecule and a miticide are provided to a *Varroa destructor* mite at least 30 days apart. In an aspect, a composition comprising a nucleic acid molecule and a miticide are provided to a *Varroa destructor* mite at least 25 days apart. In an aspect, a composition comprising a nucleic acid molecule and a miticide are provided to a *Varroa destructor* mite at least 45 days apart. In an aspect, a composition comprising a nucleic acid molecule and a miticide are provided to a *Varroa destructor* mite at least 60 days apart. In an aspect, a composition comprising a nucleic acid molecule and a miticide are provided to a *Varroa destructor* mite at least 90 days apart. In an aspect, a composition comprising a nucleic acid molecule and a miticide are provided to a *Varroa destructor* mite at least 120 days apart. In an aspect, a composition comprising a nucleic acid molecule and a miticide are provided to a *Varroa destructor* mite at least 150 days apart. In an aspect, a composition comprising a nucleic acid molecule and a miticide are provided to a *Varroa destructor* mite at least 180 days apart.

In an aspect, a composition comprising a nucleic acid molecule and an agent to control mites are provided to a *Varroa destructor* mite at least 1 day apart. In an aspect, a composition comprising a nucleic acid molecule and an agent to control mites are provided to a *Varroa destructor* mite at least 2 days apart. In an aspect, a composition comprising a nucleic acid molecule and an agent to control mites are provided to a *Varroa destructor* mite at least 3 days apart. In an aspect, a composition comprising a nucleic acid molecule and an agent to control mites are provided to a *Varroa destructor* mite at least 4 days apart. In an aspect, a composition comprising a nucleic acid molecule and an agent to control mites are provided to a *Varroa destructor* mite at least 5 days apart. In an aspect, a composition comprising a nucleic acid molecule and an agent to control mites are provided to a *Varroa destructor* mite at least 6 days apart. In an aspect, a composition comprising a nucleic acid molecule and an agent to control mites are provided to a *Varroa destructor* mite at least 7 days apart. In an aspect, a composition comprising a nucleic acid molecule and an agent to control mites are provided to a *Varroa destructor* mite at least 8 days apart. In an aspect, a composition comprising a nucleic acid molecule and an agent to control mites are provided to a *Varroa destructor* mite at least 9 days apart. In an aspect, a composition comprising a nucleic acid molecule and an agent to control mites are provided to a *Varroa destructor* mite at least 10 days apart. In an aspect, a composition comprising a nucleic acid molecule and an agent to control mites are provided to a *Varroa destructor* mite at least 11 days apart. In an aspect, a composition comprising a nucleic acid molecule and an agent to control mites are provided to a *Varroa destructor* mite at least 12 days apart. In an aspect, a composition comprising a nucleic acid molecule and an agent to control mites are provided to a *Varroa destructor* mite at least 13 days apart. In an aspect, a composition comprising a nucleic acid molecule and an agent to control mites are provided to a *Varroa destructor* mite at least 14 days apart. In an aspect, a composition comprising a nucleic acid molecule and an agent to control mites are provided to a *Varroa destructor* mite at least 15 days apart. In an aspect, a composition comprising a nucleic acid molecule and an agent to control mites are provided to a *Varroa destructor* mite at least 20 days apart. In an aspect, a composition comprising a nucleic acid molecule and an agent to control mites are provided to a *Varroa destructor* mite at least 25 days apart. In an aspect, a composition comprising a nucleic acid molecule and an agent to control mites are provided to a *Varroa destructor* mite at least 30 days apart. In an aspect, a composition comprising a nucleic acid molecule and an agent to control mites are provided to a *Varroa destructor* mite at least 45 days apart. In an aspect, a composition comprising a nucleic acid molecule and an agent to control mites are provided to a *Varroa destructor* mite at least 60 days apart. In an aspect, a composition comprising a nucleic acid molecule and an agent to control mites are provided to a *Varroa destructor* mite at least 90 days apart. In an aspect, a composition comprising a nucleic acid molecule and an agent to control mites are provided to a *Varroa destructor* mite at least 120 days apart. In an aspect, a composition comprising a nucleic acid molecule and an agent to control mites are provided to a *Varroa destructor* mite at least 150 days apart. In an aspect, a composition comprising a nucleic acid molecule and an agent to control mites are provided to a *Varroa destructor* mite at least 180 days apart.

Having now generally described the invention, the same will be more readily understood through reference to the following examples that are provided by way of illustration and are not intended to be limiting of the present invention, unless specified.

EXAMPLES

Example 1

A. Preparation of Citric Buffer

A citric acid —$Na_2HPO_4$ buffer (citric buffer) was prepared from 0.1 M citric acid monohydrate ($C_6H_8O_7.H_2O$) and 0.2 M sodium phosphate dibasic ($Na_2HPO_4$) stock solutions. A working citric buffer stock solution of pH 5.3 was created by combining 44.25 mL of 0.1 M citric acid monohydrate with 55.75 mL of 0.2 M sodium phosphate dibasic.

The citric buffer was used to adjust and stabilize the pH of several bee and/or *Varroa destructor* mite ingestible compositions comprising sucrose and a trigger nucleic acid. Several dilutions of the citric buffer stock were tested (Table 1) to determine how much citric buffer is required to obtain at a pH as close to 5.4 as possible. pH values below 5.5 are desired because sodium benzoate and potassium sorbate are known to be most effective at acidic pH values.

TABLE 1

Determining the pH of concentrations of citric buffer with dsRNA*

| Ingredient | No Buffer | 1.7% Citric Buffer | 4.6% Citric Buffer | 9.8% Citric Buffer | 100% Citric Buffer |
|---|---|---|---|---|---|
| 85% sucrose solution | 4760 μL | 4706 μL | 4706 μL | 4706 μL | 4706 μL |
| Trigger nucleic acid solution (16.6 mg/mL) | 120 μL | 120 μL | 120 μL | 120 μL | 120 μL |
| Citric Buffer (pH 5.3) | 0 μL | 3 μL | 8 μL | 17 μL | 174 μL |
| ddH$_2$O | 174 μL | 171 μL | 166 μL | 157 μL | 0 μL |
| Measured pH | 6.3 | 6.3 | 6.27 | 6.0 | 5.6 |

*Percent citric buffer is calculated as percent volume of total free volume (174 μL) in 5 mL total The trigger nucleic acid solution (20 mM NaPO$_4$; 150 mM NaCl) has a pH of 6.5, and this solution could influence the amount of citric buffer (pH 5.3) required to reach a final pH as close to 5.4 as possible. In order to test this, the pH of several citric buffer concentrations were tested without the addition of the trigger nucleic acid solution (Table 2).

TABLE 2

Determining the pH of concentrations of citric buffer without dsRNA*

| Ingredient | No Buffer | 51% Citric Buffer | 68% Citric Buffer | 85% Citric Buffer | 100% Citric Buffer |
|---|---|---|---|---|---|
| 85% sucrose solution | 4706 μL | 4706 μL | 4706 μL | 4706 μL | 4706 μL |
| Trigger nucleic acid solution (16.6 mg/mL) | 0 μL | 0 μL | 0 μL | 0 μL | 0 μL |
| Citric Buffer (pH 5.3) | 0 μL | 150 μL | 200 μL | 250 μL | 294 μL |
| ddH$_2$O | 294 μL | 144 μL | 94 μL | 44 μL | 0 μL |
| Measured pH | 6.8 | 5.7 | 5.7 | 5.7 | 5.6 |

*Percent citric buffer is calculated as percent volume of total free volume (294 μL) in 5 mL total B. Preparation of Food Grade Preservatives Separate working solutions of sodium benzoate and potassium sorbate are prepared in citric buffer (pH 5.3) and pH is measured as shown in Table 3.

TABLE 3

Measured pH of food grade preservatives in citric buffer

| Preservative | Amount Added | Citric Buffer Volume | Final Concentration of Preservative | pH |
|---|---|---|---|---|
| Sodium Benzoate | 2000 mg | 40 mL | 50 mg/mL | 5.47 |
| Potassium Sorbate | 2000 mg | 40 mL | 50 mg/mL | 6.13 |

It was determined that potassium sorbate has low solubility in citric buffer, so a second working stock with a higher concentration was produced in ddH$_2$O (Table 4). This minimized the volume of potassium sorbate that would need to be added to the final compositions and thus would not influence the final pH of the compositions.

TABLE 4

Measured pH of food grade preservatives in citric buffer and ddH$_2$O

| Preservative | Amount Added | Citric Buffer Volume | ddH$_2$O Volume | Final Concentration of Preservative | pH |
|---|---|---|---|---|---|
| Sodium Benzoate | 4000 mg | 40 mL | 0 mL | 100 mg/mL | 5.7 |
| Potassium Sorbate | 4000 mg | 0 mL | 40 mL | 100 mg/mL | 8.8 |

C. Preparation of Beehive Microbiota

Contaminating stock was generated by collecting natural contaminators from 10 beehive feeders. This was done by shaking 1 liter of 30% sucrose solution in empty beehive feeders for approximately two minutes, then collecting the sucrose solution. The collected solutions were incubated at 35° C. for four days. The sucrose solutions were visibly contaminated at this point.

Approximately 20 μL from each sucrose solution was spread on different LB TSA (Luria Bertani trypticase soy agar) agar plates to confirm the viability of bacteria in the sucrose solutions. Similarly, approximately 20 μL from each sucrose solution was spread on different SDA (Sabouraud dextrose agar) agar plates to confirm the viability of fungi in the sucrose solutions.

After confirming that all sucrose stock solutions were viable, all 10 contaminated sucrose stock solutions were combined and homogenized. The combined stock contamination solution was divided into approximately 800 mL aliquots and centrifuged at 6000×G for 10 minutes at 4° C. to recover a pellet of microorganisms. The supernatants were removed and the recovered pellets were then resuspended in 10 mL of 1×PBS (phosphate buffered saline) and divided into 1 mL aliquots.

The 1 mL aliquots were again centrifuged at 6000×G for 10 minutes at 4° C. to recover pellets after the removal of the supernatant. The pellets were divided into three groups to determine the optimal storage conditions for the contamination stock: (1) dry pellet; (2) pellet resuspended in 500 μL of 50% glycerol prepared in 1×PBS; and (3) pellet resuspended in 500 μL of 50% glycerol prepared in ddH$_2$O. All of the pellets were then frozen overnight at −80° C.

An aliquot from each storage group was thawed on ice. The dry pellet was resuspended in 1 mL 1×PBS, while 500 μL of 1×PBS was added to the pellets in in glycerol from groups (2) and (3) before resuspending the pellets in solution. Starter cultures were grown in 5 mL of sterile LB broth at 37° C., shaking at 200 rpm, for 4 hours. Optical density at 600 nm ($OD_{600}$) was measured for each sample. See Table 5.

TABLE 5

| $OD_{600}$ of contamination stock groups | |
|---|---|
| Sample-Storage method | $OD_{600}$ |
| Control (uncontaminated LB) | 0.05 |
| Group (1)-Dry pellet | 0.179 |
| Group (2)-50% glycerol + 1x PBS | 0.097 |
| Group (3)-50% glycerol + $ddH_2O$ | 0.087 |

Approximately 20 μL of contamination stock from each storage method starter culture, and approximately 20 μL of the resuspended pellets, were plated on both TSA and SDA plates and allowed to grow overnight at 37° C. to again confirm the viability of the contamination stocks.

D. Testing the Ability of Food Grade Preservatives to Enhance dsRNA Stability

The trigger nucleic acid molecule (SEQ ID NO: 1, see Table 6) tested herein comprises 376 nucleotides (CAM376). CAM376 is homologous to a *Varroa destructor* calmodulin gene and is nearly identical to SEQ ID NO: 3 (SEQ ID NO: 3 comprises deletions at nucleotide positions 109, 200, 239, and 270 of instant SEQ ID NO: 1) from U.S. Pat. No. 9,540,642, (which is incorporated by reference herein in its entirety), which has been shown to down-regulate expression of a calmodulin gene in *Varroa destructor*. A working stock of 20 mg/mL was prepared in citric buffer (pH 5.3).

TABLE 6

| Trigger nucleic acid molecule | | |
|---|---|---|
| SEQ ID NO. | Name | Sequence |
| 1 | CAM376 | GGAACAGATCGCCGAGTTCAAAGAGGCGTTTAGCCTGTTTGACAA GGACGGAGATGGCACGATCACGACAAAGGAGCTCGGTACGGTAAT GCGATCTCTCGGCCAGAACCCCACTGAGGCTGAACTGCAGGACAT GATCAACGAGGTCGACGCCGACGGCTCCGGAACGATAGATTTCCC TGAGTTCCTCACAATGATGGCAAGAAAGATGAAGGACACCGACTC GGAGGAGGAGATCCGAGAGGCGTTCCGCGTATTCGACAAGGATGG CAACGGTTTCATTTCGGCGGCCGAGCTCAGGCACGTTATGACCAA CCITGGCGAGAAGCTTACGGACGAGGAGGTAGATGAGATGATTCG GGAGGCAGATATTGAC |
| 2 | CAM373 | ACAGATCGCCGAGTTCAAAGAGGCGTTTAGCCTGTTTGACAAGGA CGGAGATGGCACGATCACGACAAAGGAGCTCGGTACGGTAATGCG ATCTCTCGGCCAGAACCCCACTGAGGCTGACTGCAGGACATGAT CAACGAGGTCGACGCCGACGGCTCCGGAACGATAGATTTCCCTGA GTTCCTCACAATGATGGCAAGAAAGATGAAGGACACCGACTCGGA GGAGGAGATCCGAGAGGCGTTCCGCGTATTCGACAAGGATGGCAA CGGTTTCATTTCGGCGGCCGAGCTCAGGCACGTTATGACCAACCT TGGCGAGAAGCTTACGGACGAGGAGGTAGATGAGATGATTCGGGA GGCAGATATTGAC |
| 3 | | GGAACAGATCGCCGAGTTCAAAGAGGCGTTTAGCCTGTTTGACAA GGACGGAGATGGCACGATCACGACAAAGGAGCTCGGTACGGTAAT GCGATCTCTCGGCCAGAACCCACTGAGGCTGAACTGCAGGACATG ATCAACGAGGTCGACGCCGACGGCTCCGGAACGATAGATTTCCCT GAGTTCCTCACAATGATGCAAGAAAGATGAAGGACACCGACTCGG AGGAGGAGATCGAGAGGCGTTCCGCGTATTCGACAAGGATGCAAC GGTTTCATTTCGGCGGCCGAGCTCAGGCACGTTATGACCAACCTT GGCGAGAAGCTTACGGACGAGGAGGTAGATGAGATGATTCGGGAG GCAGATATTGAC |

Five formulations (Table 7) using the citric buffer of Example 1A and the preservatives of Example 1B were tested to determine the stability of the trigger nucleic acid molecule (SEQ ID NO: 1) in a) only sucrose (control); b) sucrose with preservatives; c) sucrose and citric buffer; d) sucrose with equal amounts of each preservative in citric buffer; and e) sucrose with sodium benzoate to potassium sorbate in a 1:0.5 ratio in citric buffer.

TABLE 7

Tested formulations

| Formulation Number | Composition of Formulation | Measured pH of Formulation |
|---|---|---|
| 1 | 80% sucrose with CAM 376 (0.4 mg/mL) | 6 |
| 2 | 80% sucrose with CAM 376 (0.4 mg/mL), sodium benzoate (0.1% w/v), and potassium sorbate (0.1% w/v) | 6 |
| 3 | 80% sucrose with CAM376 (0.4 mg/mL) in citric buffer (pH 5.3) | 5 |
| 4 | 80% sucrose with CAM 376 (0.4 mg/mL), sodium benzoate (0.1% w/v), and potassium sorbate (0.1% w/v) in citric buffer (pH 5.3) | 5 |
| 5 | 80% sucrose with CAM 376 (0.4 mg/mL), sodium benzoate (0.1% w/v), and potassium sorbate (0.05% w/v) in citric buffer (pH 5.3) | 5 |

Contamination Stock pellets from Group (1) in Example 1C were resuspended in 1 mL of 1× phosphate buffered saline (PBS) on ice, then the eluted Contamination Stock was added to each Formulation of Table 7 to a final concentration of 80× (12.5 µL/mL).

In order to test the stability of CAM376 in each Formulation, each Formulation was divided into triplicate (3 mL/replicate; 9 mL total) and kept in a 35° C. water bath. At several time points (Day 0, Day 4, Day 7, Day 10, Day 14, Day 17, and Day 21) a 100 µL was removed from each replicate from Formulation.

Each 100 µL aliquot was diluted with 300 µL of ddH$_2$O. From the diluted aliquots, 100 µL was used for ultra-pure liquid chromatography (UPLC) for quantitative measurement, and 4 µL was loaded into a 2% TAE agarose gel for quantitative/qualitative measurement (see FIG. 1). UPLC measurements were taken for Day 0, Day 4, Day 7, and Day 10 (see FIG. 2 and Table 8). For Day 0, only one UPLC measurement was taken prior to splitting the original Formulation into triplicates.

TABLE 8

UPLC measurements* of CAM376 in tested Formulations

| Formulation | Day 0 | Day 4 | Day 7 | Day 10 |
|---|---|---|---|---|
| 1A | 312.99 | 148.97 | 0 | 0 |
| 1B |  | 187.2 | 0 | 0 |
| 1C |  | 189.74 | 0 | 0 |
| 2A | 285.39 | 297.24 | 242.38 | 251.77 |
| 2B |  | 296.4 | 224.7 | 236.68 |
| 2C |  | 305.49 | 239.2 | 246.39 |
| 3A | 249.41 | 178.01 | 31.17 | 0 |
| 3B |  | 191.64 | 30.78 | 0 |
| 3C |  | 201.05 | 20.76 | 0 |
| 4A | 320.05 | 344.55 | 247.35 | 240.18 |
| 4B |  | 272.71 | 235 | 231.91 |
| 4C |  | 326.73 | 260.81 | 232.69 |
| 5A | 319.76 | 323.87 | 228.12 | 237.09 |
| 5B |  | 344.21 | 254.89 | 213.99 |
| 5C |  | 285.46 | 252.69 | 271.96 |

*-Measurement values provide the area beneath the peak curve

Figures 1, 1C:
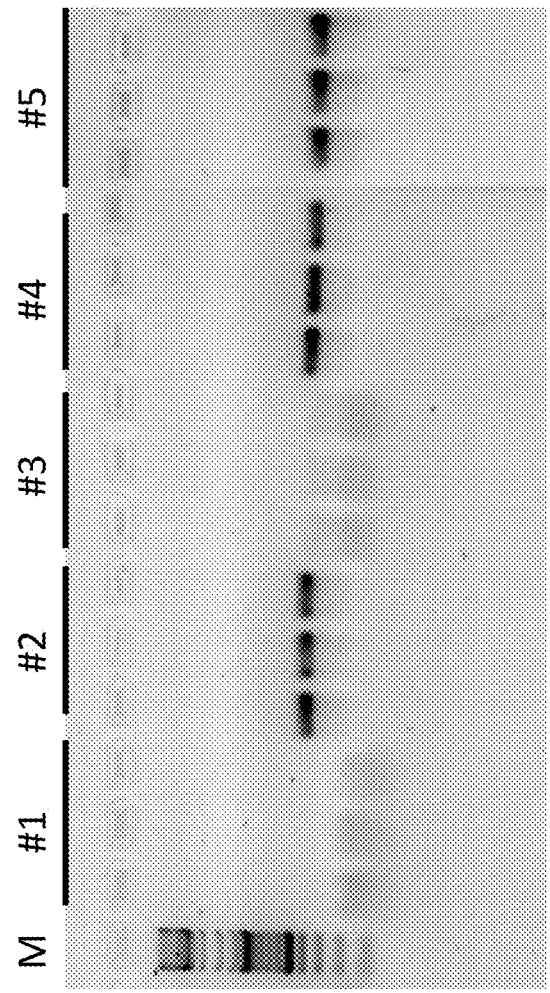
FIG. 1C depicts CAM376 at Day 7.
Figure 1D:
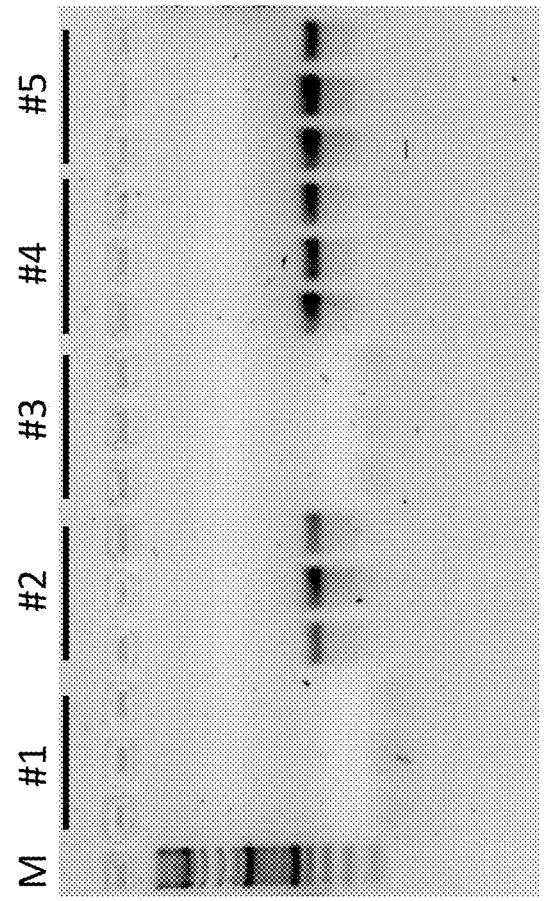
FIG. 1D depicts CAM376 at Day 10.
Figures 1, 1E:
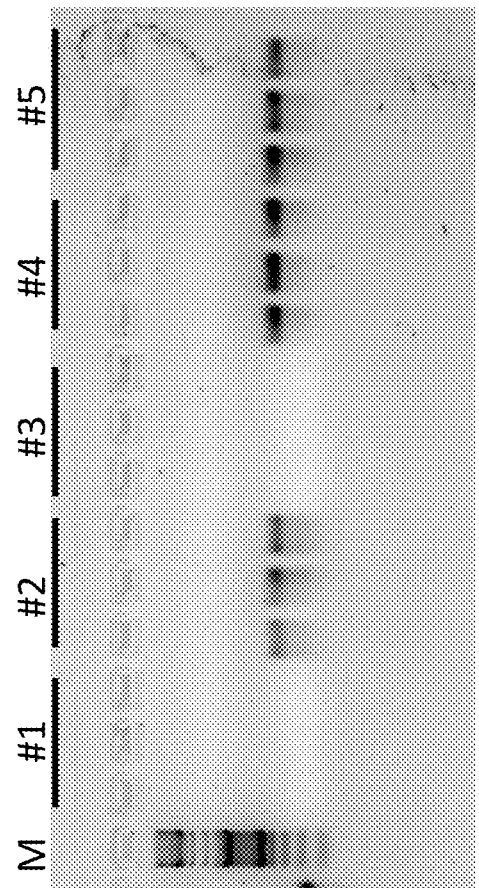
FIG. 1E depicts CAM376 at Day 14.
Figures 1, 1F:
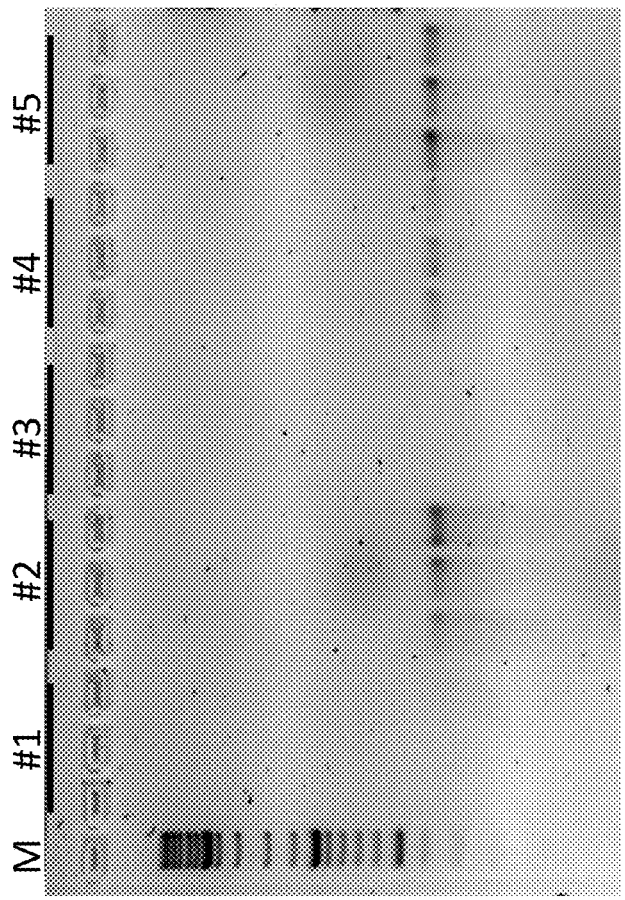
FIG. 1F depicts CAM376 at Day 17.
Figure 1G:
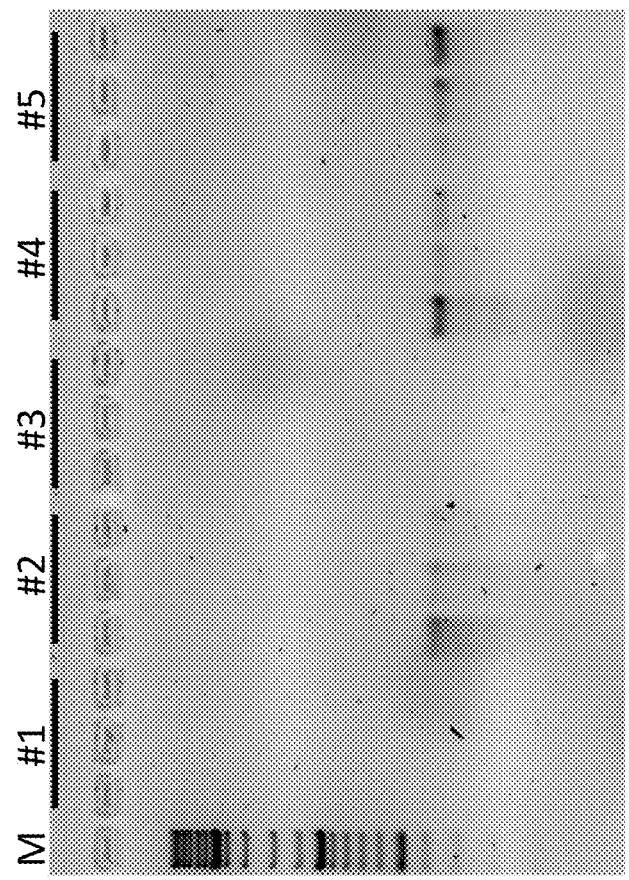
FIG. 1G depicts CAM376 at Day 20.
Figures 2, 2A:
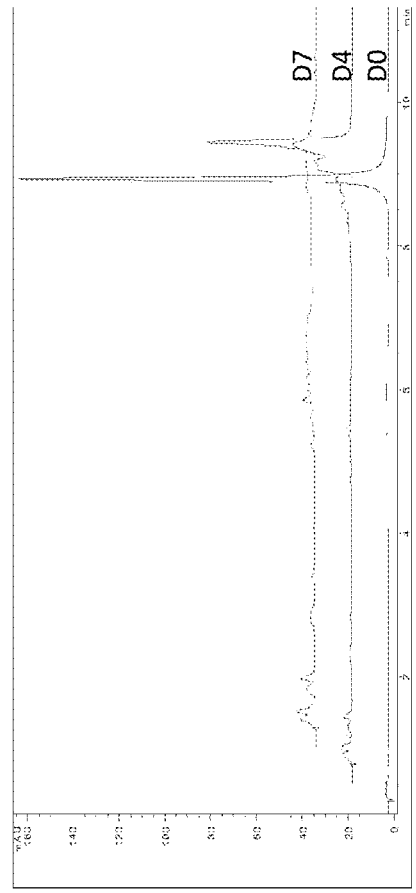
FIG. 2 demonstrates the degradation, or lack thereof, of CAM376 at various time points in the presence of a contaminating microbiota solution and also in the presence or absence of food-grade preservatives and/or citric buffer at various time points using ultra-pure liquid chromatography (UPLC). A starting concentration of 0.4 mg/mL was used for CAM376 in each experimental group.
FIG. 2A depicts UPLC results for CAM376 in an 80% sucrose solution at day 0 (D0; (prior to the addition of the contaminating microbiota solution), day 4 (D4), and day 7 (D7). The peaks on the right side of the graph demonstrate the presence of CAM376 at D0 and D4, but not D7.
Figures 2, 2B:
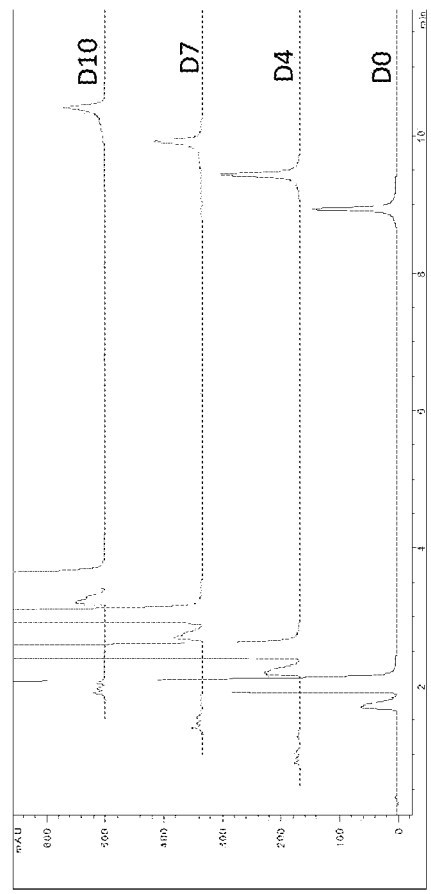
FIG. 2B depicts UPLC results for CAM376 in an 80% sucrose solution with 0.1% (w/v) sodium benzoate and 0.1% (w/v) potassium sorbate at D0, D4, D7, and day 10 (D10). The peaks on the left side of the graph represent the food-grade preservatives sodium benzoate and potassium sorbate. The peaks on the right side of the graph represent the continued presence of CAM376.
Figures 2, 2C:
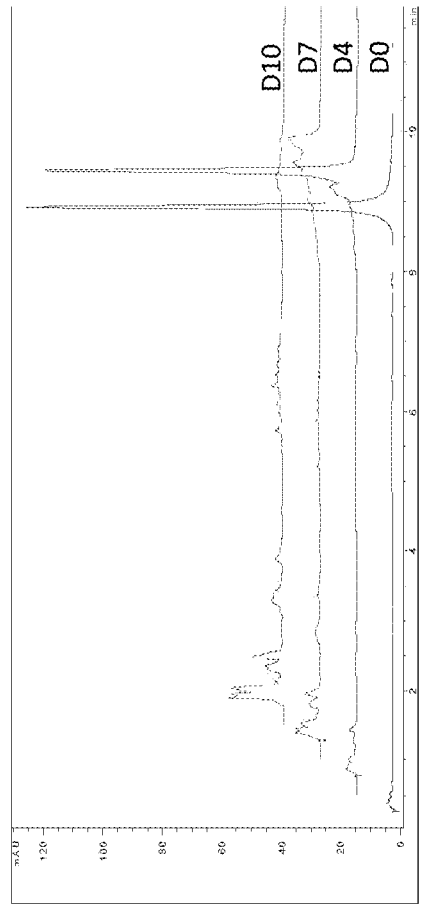
FIG. 2C depicts UPLC results for CAM376 in an 80% sucrose solution with citric buffer at D0, D4, D7, and D10. The peaks on the left side of the graph represent degraded double-stranded RNAs. The peaks on the right side of the graph demonstrate the presence of CAM376 at D0, D4, and D7, but not D10.
Figures 2, 2D:
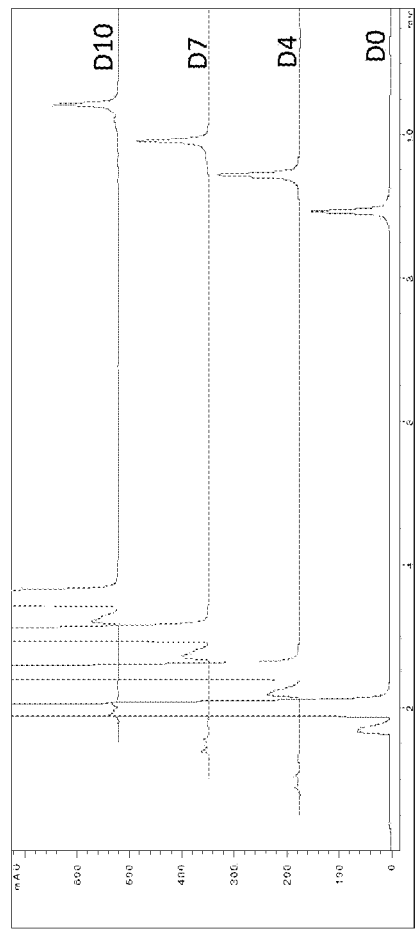
FIG. 2D depicts UPLC results for CAM376 in an 80% sucrose solution with 0.1% (w/v) sodium benzoate, 0.1% (w/v) potassium sorbate, and citric buffer at D0, D4, D7, and D10. The large peaks on the left side of the graph represent sodium benzoate and potassium sorbate. The peaks on the right side of the graph demonstrate the presence of CAM376 at all four time points.
Figures 2, 2E:
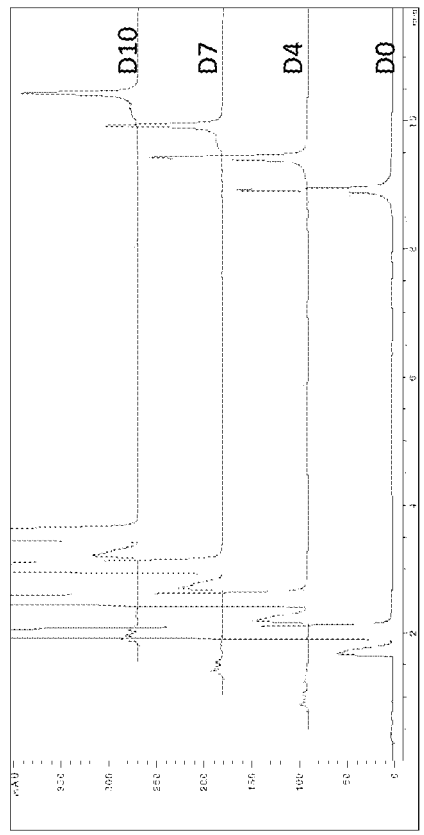
FIG. 2E depicts UPLC results for CAM376 in an 80% sucrose solution with 0.1% (w/v) sodium benzoate, 0.05% (w/v) potassium sorbate, and citric buffer at D0, D4, D7, and D10. The large peaks on the left side of the graph represent sodium benzoate and potassium sorbate. The peaks on the right side of the graph demonstrate the presence of CAM376 at all four time points.

CAM376 degenerated rapidly in Formulation #1 and was not detectable via UPLC or agarose gel by Day 7 (Table 8; FIGS. 1C and 2). Similarly, CAM376 degraded quickly in Formulation #3, and was not detectable via UPLC or agarose gel by Day 10 (Table 8; FIGS. 1D and 2). CAM376 degraded more slowly in Formulations #2, #4, and #5, and non-degraded DNA was still detectable via UPLC on Day 10 (Table 8; FIG. 2) and via agarose gel on Day 20 (FIG. 1G).

The results demonstrate that the addition of sodium benzoate and potassium sorbate prolong the life span of nucleic acid molecules when subjected to the natural microbiome present in beehive feeders.

Example 2. Testing the Ability of a Single Food-Grade Preservative to Protect a dsRNA Four additional formulations were created to test the ability of sodium benzoate alone to protect a dsRNA from degradation. See Table 9. Sodium benzoate was prepared in a solution with a pH of 4.5.

TABLE 9

Tested formulations

| Formulation Number | Composition of Formulation | Measured pH of Formulation |
|---|---|---|
| 6 | 66% sucrose with CAM 373 (0.4 mg/mL) | 6 |
| 7 | 66% sucrose with CAM 373 (0.4 mg/mL) and sodium benzoate (0.1% w/v) | 6 |
| 8 | 80% sucrose with CAM373 (0.4 mg/mL) | 6 |
| 9 | 80% sucrose with CAM 373 (0.4 mg/mL), and sodium benzoate (0.1% w/v) | 6 |

Contamination Stock from Example 1C was eluted in 1 mL of 1× phosphate buffered saline (PBS) on ice, then the eluted Contamination Stock was added to each Formulation of Table 8 to a final concentration of 80× (12.5 µL/mL).

In order to test the stability of CAM376 in each Formulation, each Formulation was divided into triplicate (3 mL/replicate; 9 mL total) and kept in a 35° C. water bath. At several time points (Day 0, Day 5, Day 7, Day 14, Day 21, Day 28, and Day 35) a 100 µL was removed from each replicate from Formulation.

Each 100 µL aliquot was diluted with 300 µL of ddH$_2$O. From the diluted aliquots, 100 µL was used for ultra-pure liquid chromatography (UPLC) for quantitative measurement, and 4 µL was loaded into a 2% TAE agarose gel for quantitative/qualitative measurement (see FIG. 1). UPLC measurements were taken for Day 0, Day 4, Day 7, and Day 10 (see FIG. 2 and Table 7). For Day 0, only one UPLC measurement was taken prior to splitting the original Formulation into triplicates.

Figure 3A:
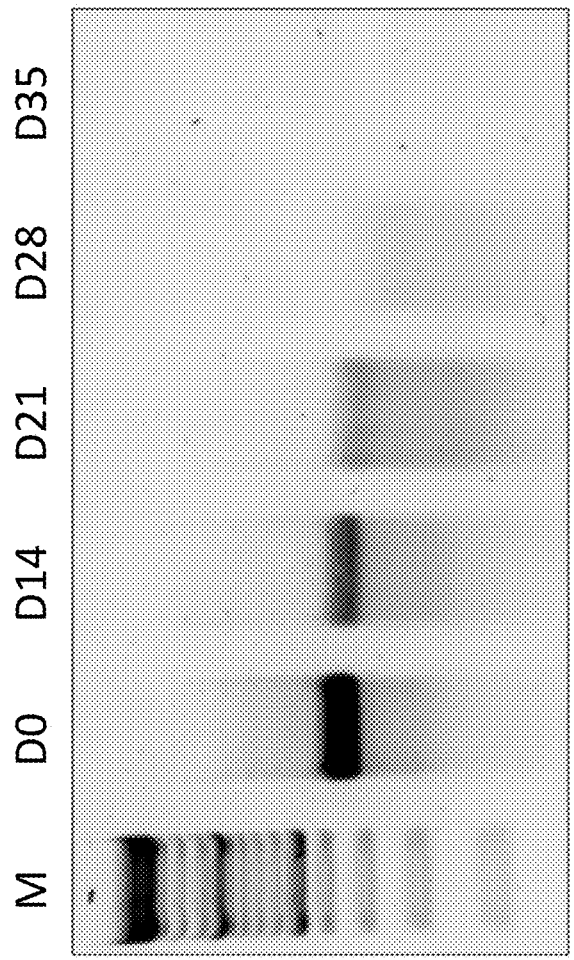
FIG. 3A depicts CAM376 in 66% sucrose solution.
Figures 3, 3B:
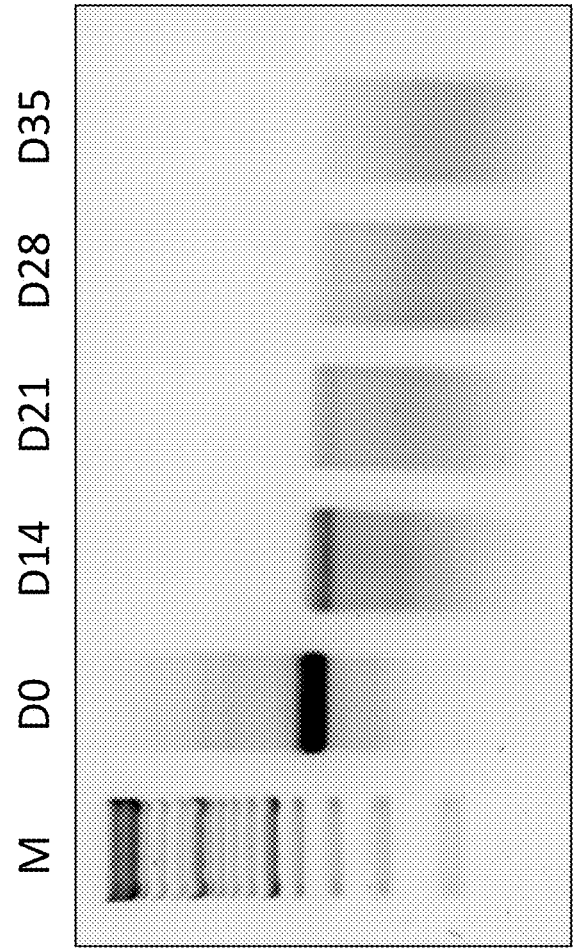
FIG. 3 shows CAM376 electrophoresed on 2% TAE (Tris base, acetic acid, EDTA) agarose gels. The agarose gels depict CAM376 at various time points in the presence of a contaminating microbiota solution and also in the presence or absence of 0.1% (w/v) sodium benzoate at various time points. A starting concentration of 0.4 mg/mL was used for CAM376 in each experimental group. In all parts of FIG. 3, M represents the nucleic acid length marker; D0 represents day 0; D14 represents day 14; D21 represents day 21; D28 represents day 28; and D35 represents day 35.
FIG. 3B depicts CAM376 in 66% sucrose solution and 0.1% sodium benzoate.
Figures 3, 3C:
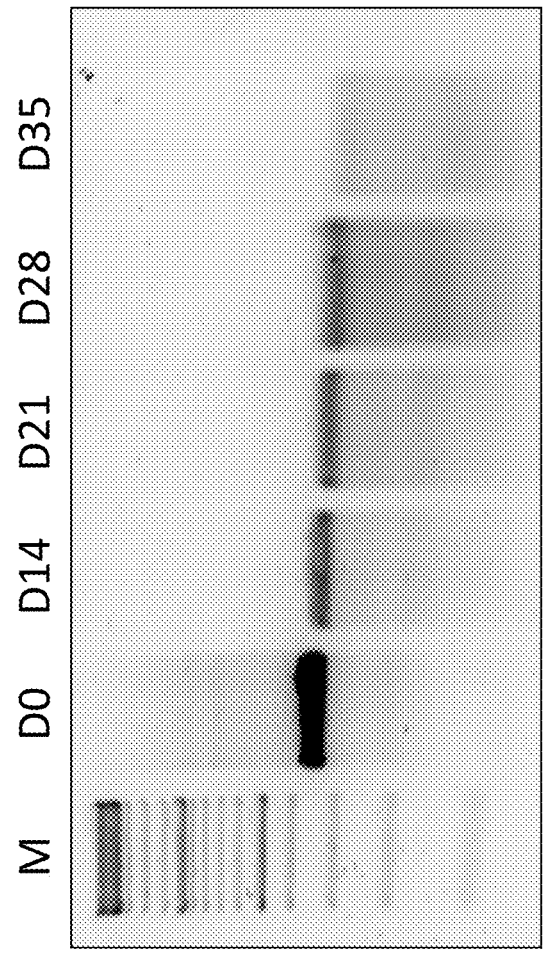
FIG. 3C depicts CAM376 in 80% sucrose solution.
Figures 3, 3D:
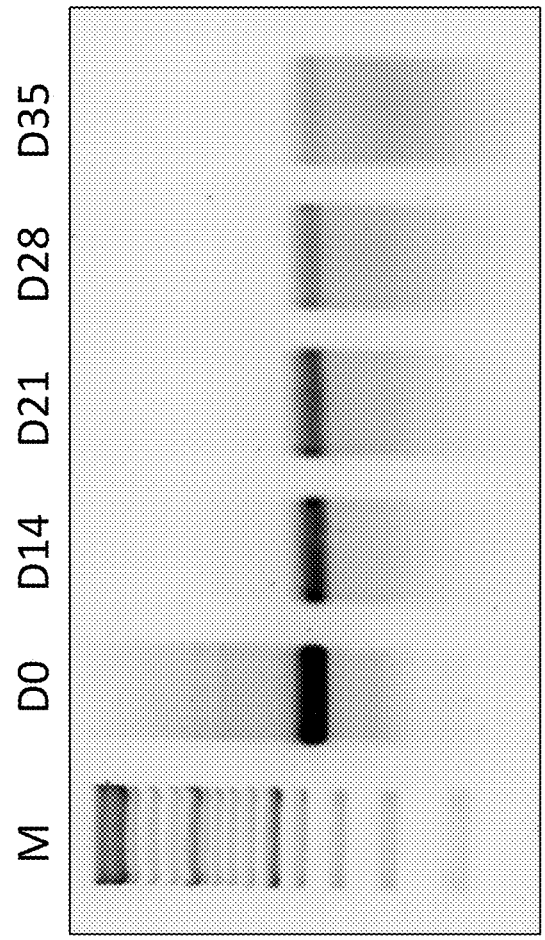
FIG. 3D depicts CAM376 in 80% sucrose solution and 0.1% sodium benzoate.
Figures 4, 4A:
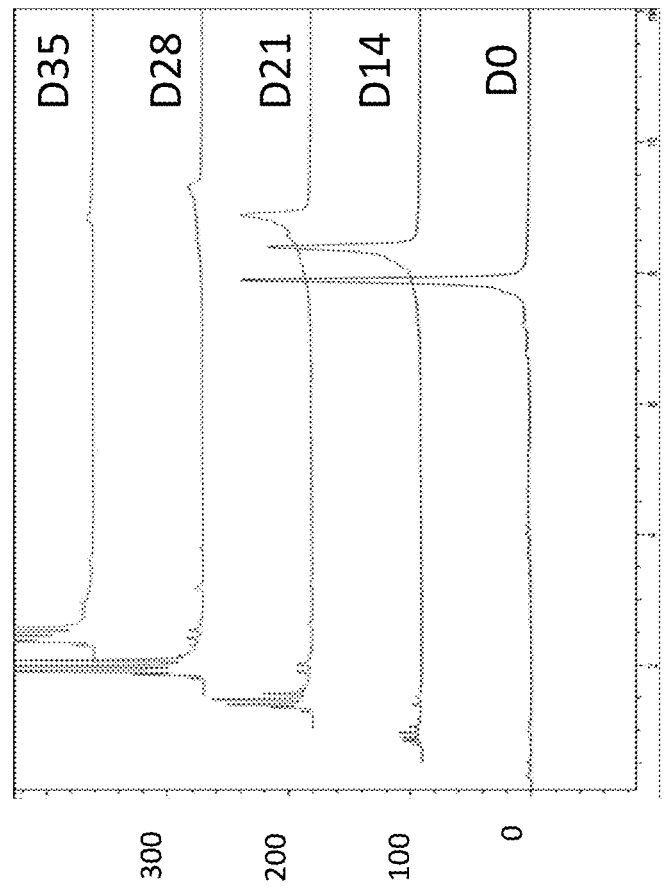
FIG. 4 demonstrates the degradation, or lack thereof, of CAM376 at various time points in the presence of a contaminating microbiota solution and also in the presence or absence 0.1% sodium benzoate at various time points using ultra-pure liquid chromatography (UPLC). A starting concentration of 0.4 mg/mL was used for CAM376 in each experimental group. In all parts of FIG. 4, D0 represents day 0; D14 represents day 14; D21 represents day 21; D28 represents day 28; and D35 represents day 35.
FIG. 4A depicts CAM376 in 66% sucrose solution. The peaks on the left depict CAM376 degradation products, while the peaks on the right depict intact CAM376.
Figures 4, 4B:
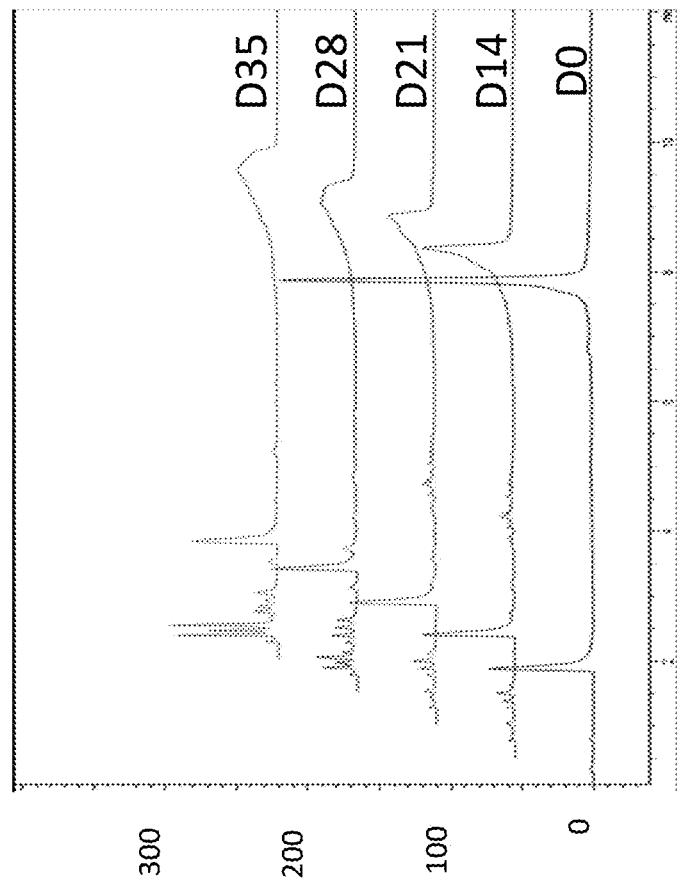
FIG. 4B depicts CAM376 in 66% sucrose solution and 0.1% sodium benzoate. The left-most peaks depict CAM376 degradation products, the middle peaks depict sodium benzoate, and the right peaks depict intact CAM376.
Figures 4, 4C:
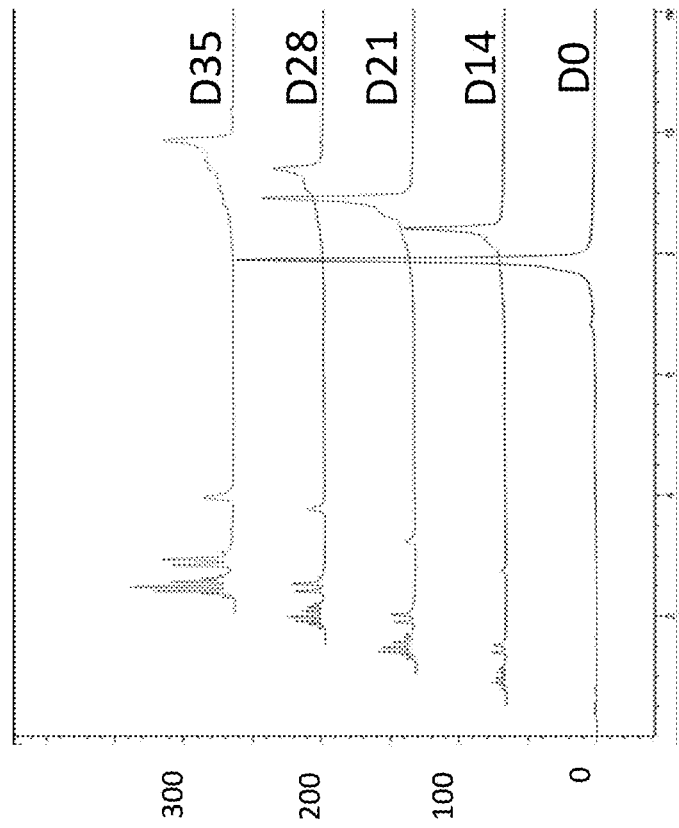
FIG. 4C depicts CAM376 in 80% sucrose solution. The peaks on the left depict CAM376 degradation products, while the peaks on the right depict intact CAM376.
Figures 4, 4D:
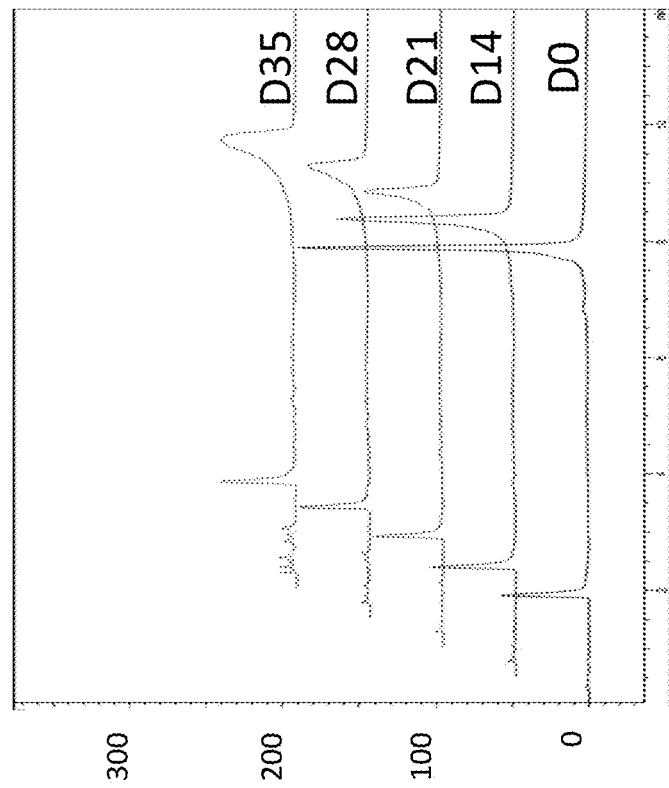
FIG. 4D depicts CAM376 in 80% sucrose solution and 0.1% sodium benzoate. The left-most peaks depict CAM376 degradation products, the middle peaks depict sodium benzoate, and the right peaks depict intact CAM376.

The dsRNA in Formulation 6 (66% sucrose) degraded steadily and was almost undetectable by Day 28. See FIGS. 3A and 4A. The dsRNA in Formulation 7 (66% sucrose and 0.1% sodium benzoate) also degraded steadily, although some dsRNA was still detectable by both UPLC and agarose gel at Day 28 and Day 35. See FIGS. 3B and 4B. The dsRNA in Formulation 8 (80% sucrose) was detectable at all time points measured, although the dsRNA degraded over time. See FIGS. 3C and 4C. The dsRNA in Formulation 9 (80% sucrose and 0.1% sodium benzoate) also degraded over time, but Formulation 9 retained the highest amount of dsRNA of these four Formulations at Day 35. See FIGS. 3D and 4D. Notably, the addition of a second food-grade preservative (e.g., potassium sorbate) in Example 1 above further improved the stability of dsRNAs over time.

Example 3. Testing the Efficacy of dsRNAs with and without Food-Grade Preservatives In order to test the efficacy of dsRNAs complementary to *Varroa destructor* mite miRNAs in the presence of food-grade preservatives, such compositions are tested in beehives. The beehives are naturally infected with *Varroa* mites prior to the start of the experiment. A control group of beehives is provided with compositions comprising CAM373 (SEQ ID NO: 2) dsRNAs only. A second group of beehives is provided with compositions comprising the dsRNAs and 0.1% (w/v) sodium benzoate and 0.1% (w/v) potassium sorbate.

The number of mites in the beehives and the strength of the beehives (e.g., the number of bees present) are assessed at weeks 1 (April), 7 (June), 13 (July), 18 (August), 24 (October), and 29 (January).

Example 4. Combining and Comparing dsRNAs Complementary to *Varroa* Mite mRNA and Miticide Treatment Treating beehives with miticides and double-stranded RNAs complementary to *Varroa destructor* mRNA may be advantageous in treating or preventing a *Varroa destructor* mite infestation of a beehive.

dsRNAs Targeting *Varroa* Calmodulin mRNA Augmented a Common Miticide Treatment

Four treatment groups were set up to determine whether CAM373 (SEQ ID NO: 2) dsRNAs complementary to the *Varroa destructor* mite for the Calmodulin mRNA can augment Apivar® treatment to prevent and/or reduce a *Varroa destructor* mite infestation of a beehive. Each beehive is naturally infected with *Varroa* mites prior to the start of the experiment.

Figure 5:
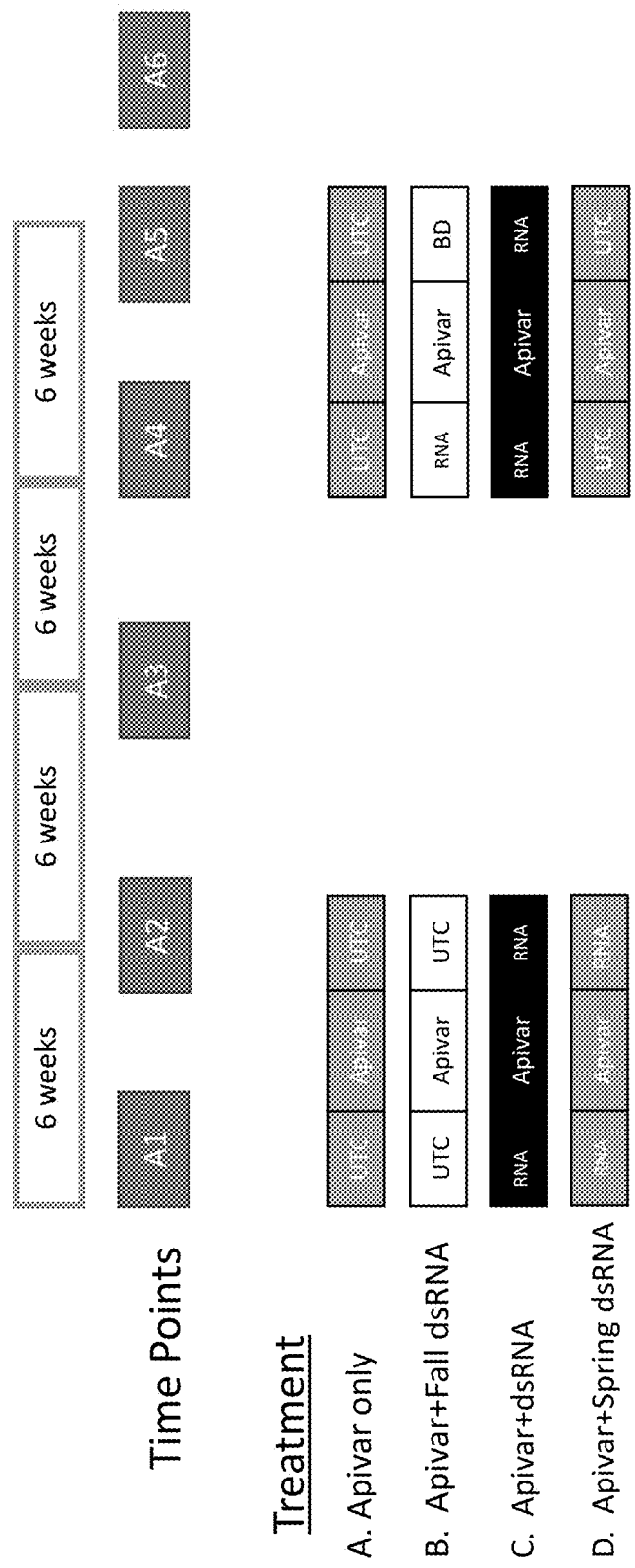
FIG. 5 is a graphic representation of the protocol used for the miticide (Apivar) treatment only or the miticide (Apivar) plus the dsRNA. The study was initiated in the Spring (Timepoint A1) when the dsRNA plus or minus miticide treatment were added to the hives (Treatments C and D). At Timepoint A2, six weeks later, an additional dsRNA treatment was added to Treatments C and D. Conversely, dsRNA was added to Treatments B (Apivar+Fall dsRNA) and C at 18 and 24 weeks. UTC=Untreated Control. BD=dsRNA.
Figure 6:
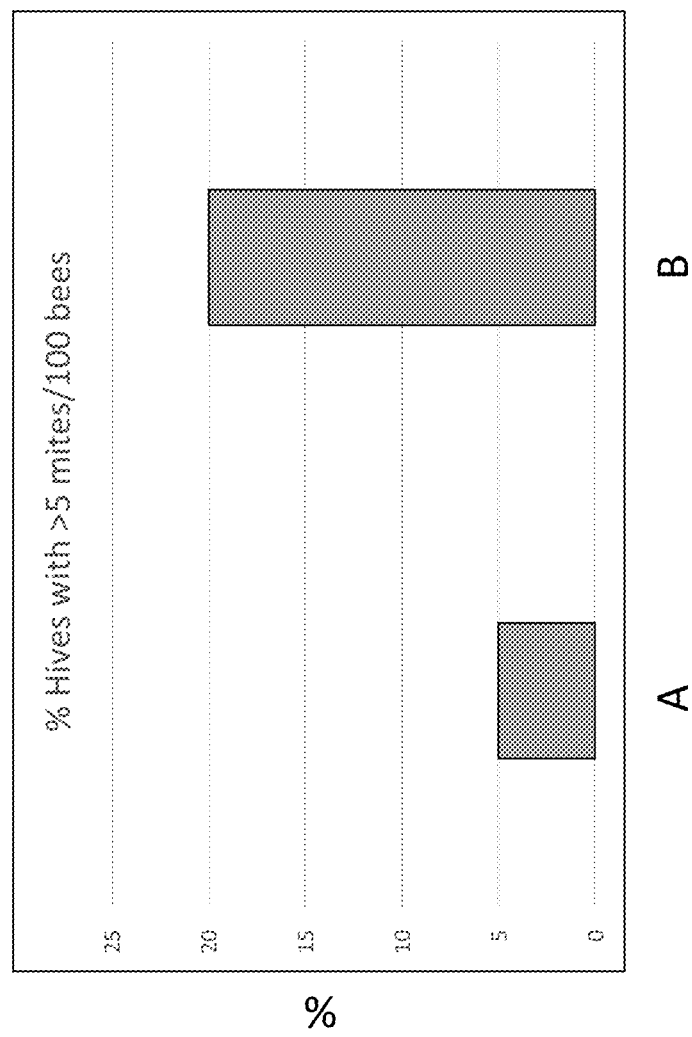
FIG. 6 illustrates the percent of bee hives with more than 5 mites per 100 bees. These data were taken at Timepoint A5 (see FIG. 5), after 24 weeks. The bar labeled A illustrates the overall percent hives in the Apivar+dsRNA treatment, while the bar labeled B illustrates the percent hives treated only with Apivar.

A general scheme of delivery for this protocol can be seen in FIG. 5. Four distinct treatments were provided. In the first group, the miticide Apivar® (amitraz) is provided as a plastic strip imbibed in the active amitraz as a one strip for each five frames to 40 beehives in Spring and again in Fall for a total duration of six weeks for each treatment. In the second group, Apivar® was first provided alone in the Spring and subsequently, Apivar® and a composition comprising the dsRNA (consisting of a 500 mL solution of 80% sucrose mixed with 1 gram of SEQ ID NO: 2 dsRNA) were provided to 40 beehives together in Fall. In the third group, Apivar® and a composition comprising the dsRNA were provided to 40 beehives in both Spring and Fall. In the fourth group, Apivar® and a composition comprising the dsRNA were provided to 40 beehives in Spring, while the Apivar® only treatment was given in Fall. The Apivar+dsRNA treatments are delivered simultaneously to the hive and replaced every six weeks. The number of mites in the beehives and the strength of the beehives (e.g., the number of bees present) were assessed at weeks 1 (A1), 7 (A2), 13 (A3), 18 (A4), 24 (A5) and 29 (A6). The main goal for the combined treatment was to keep the mite population below threshold. The threshold is established by the number of mites which will damage the hive. Historically, this threshold is set at five mites per one hundred bees (5 m/100 b). At the conclusion of 24 weeks (time point A5) the percent hives with more than five mites per one hundred bees was measured (FIG. 6). This measurement revealed that the Apivar® plus dsRNA treatment (treatment A.) resulted in significantly less hives with levels of mites above threshold.

Figure 7:
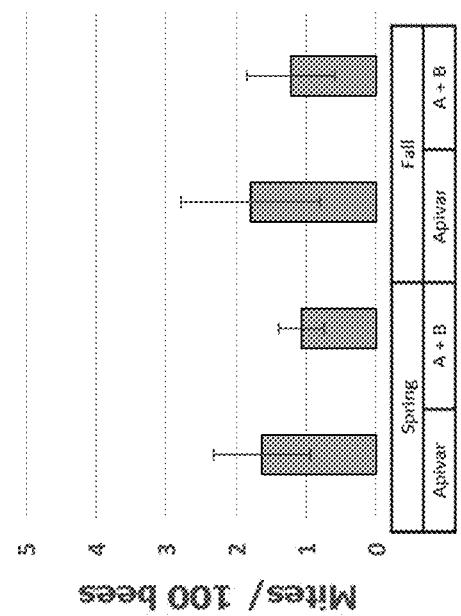
FIG. 7 is a graphic illustration of the number of mites per 100 bees in the Spring and Fall treatments with Apivar only (Apivar) or Apivar plus dsRNA (A+B).

Additionally, a breakdown of the data into Spring and Fall individual treatments revealed that the miticide+dsRNA treatments together provided better mite control than the miticide treatment alone (FIG. 7).

Figure 8:
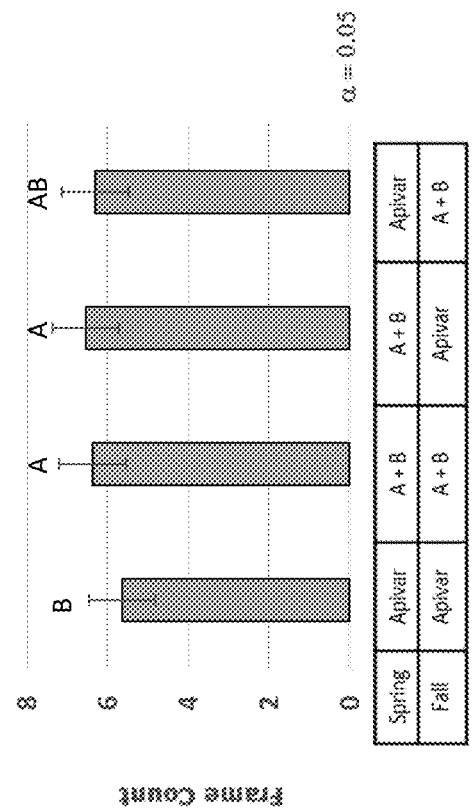
FIG. 8 is the final frame count at Timepoint A6 (29 weeks; see FIG. 5). Frames that were covered at least by 75% surface area with living bees were counted for both the Apivar only (Apivar) or the Apivar+dsRNA (A+B) treatments and plotted as illustrated.

At the completion of the field trial, colonies were assessed for hive strength by counting the number of frames that were covered by at least 75% with living bees. This provides a reasonable estimate of the number of bees in the colony. On average, colonies treated with Apivar and dsRNA had approximately twenty percent (20%) more bees than those that had received the Apivar only treatment (FIG. 8).

What is claimed is:

1. A method of treating or preventing an *Varroa destructor* infestation of a beehive or bee colony comprising:
   (a) providing to the beehive or bee colony a composition comprising a nucleic acid molecule, wherein the nucleic acid molecule is a dsRNA that comprises a sequence that is complementary or identical to at least 21 contiguous nucleotides of a *Varroa destructor* messenger RNA (mRNA); and sodium benzoate or potassium sorbate, or both; and
   (b) providing an agent to control mites to the beehive or bee colony, wherein the agent to control mites is amitraz;
   thereby treating or preventing the *Varroa destructor* infestation of the beehive or bee colony.

2. The method of claim 1, wherein the composition further comprises a carbohydrate.

3. The method of claim 2, wherein the carbohydrate is sucrose composition further comprises a food grade preservative.

4. The method of claim 1, wherein the nucleic acid molecule is provided before the agent to control mites.

5. The method of claim 1, wherein the agent to control mites is provided before the nucleic acid molecule.

6. The method of claim 1, wherein the at least one nucleic acid molecule and the agent to control mites are provided at least 1 day apart.

7. A method of causing mortality or reducing the fecundity of a *Varroa destructor* mite comprising:
   (a) providing to the *Varroa destructor* mite a composition comprising a nucleic acid molecule and sodium benzoate or potassium sorbate, or both, wherein the nucleic acid molecule is a dsRNA that comprises a sequence that is complementary to a *Varroa destructor* mite messenger RNA (mRNA); and
   (b) providing an agent to control mites to the *Varroa destructor* mite, wherein the agent to control mites is amitraz;
   thereby causing mortality or reducing the fecundity of the *Varroa destructor* mite.

8. The method of claim 7, wherein the mortality occurs within 30 days of providing the nucleic acid molecule.

9. The method of claim 7, wherein the reduced fecundity comprises a reduction in *Varroa destructor* mite egg production of at least 1% as compared to a *Varroa destructor* mite egg production in a control beehive not provided the nucleic acid molecule and agent to control mites.

10. The method of claim 7, wherein the *Varroa destructor* mite is present in a beehive or bee colony.

11. The method of claim 7, wherein the nucleic acid molecule is a double-stranded RNA (dsRNA) molecule.

12. The method of claim 7, wherein the nucleic acid molecule is complementary or identical to at least 19 contiguous nucleotides of a *Varroa destructor* m RNA.

13. The method of claim 7, wherein the composition further comprises a carbohydrate.

14. The method of claim 13, wherein the carbohydrate is sucrose.

15. The method of claim 7, wherein the nucleic acid molecule is provided before the agent to control mites.

16. The method of claim 7, wherein the agent to control mites is provided before the nucleic acid molecule.

17. The method of claim 7, wherein the at least one nucleic acid molecule and the agent to control mites are provided at least 1 day apart.

* * * * *

SEQUENCE LISTING

```
<160> NUMBER OF SEQ ID NOS: 3

<210> SEQ ID NO 1
<211> LENGTH: 376
<212> TYPE: DNA
<213> ORGANISM: Artificial Sequence
<220> FEATURE:
<223> OTHER INFORMATION: Synthetic sequence. CAM376

<400> SEQUENCE: 1
ggaacagatc gccgagttca aagaggcgtt tagcctgttt gacaaggacg gagatggcac      60
gatcacgaca aaggagctcg gtacggtaat gcgatctctc ggccagaacc ccactgaggc     120
tgaactgcag gacatgatca acgaggtcga cgccgacggc tccggaacga tagatttccc     180
tgagttcctc acaatgatgg caagaaagat gaaggacacc gactcggagg aggagatccg     240
agaggcgttc cgcgtattcg acaaggatgg caacggtttc atttcggcgg ccgagctcag     300
```

```
gcacgttatg accaaccttg gcgagaagct tacggacgag gaggtagatg agatgattcg    360
ggaggcagat attgac                                                    376

<210> SEQ ID NO 2
<211> LENGTH: 373
<212> TYPE: DNA
<213> ORGANISM: Artificial Sequence
<220> FEATURE:
<223> OTHER INFORMATION: Synthetic sequence. CAM373

<400> SEQUENCE: 2
acagatcgcc gagttcaaag aggcgtttag cctgtttgac aaggacggag atggcacgat     60
cacgacaaag gagctcggta cggtaatgcg atctctcggc cagaacccca ctgaggctga   120
actgcaggac atgatcaacg aggtcgacgc cgacggctcc ggaacgatag atttccctga   180
gttcctcaca atgatggcaa gaaagatgaa ggacaccgac tcggaggagg agatccgaga   240
ggcgttccgc gtattcgaca aggatggcaa cggtttcatt tcggcggccg agctcaggca   300
cgttatgacc aaccttggcg agaagcttac ggacgaggag gtagatgaga tgattcggga   360
ggcagatatt gac                                                      373

<210> SEQ ID NO 3
<211> LENGTH: 372
<212> TYPE: DNA
<213> ORGANISM: Artificial Sequence
<220> FEATURE:
<223> OTHER INFORMATION: Synthetic sequence. CAM

<400> SEQUENCE: 3
ggaacagatc gccgagttca agaggcgtt tagcctgttt gacaaggacg gagatggcac     60
gatcacgaca aaggagctcg gtacggtaat gcgatctctc ggccagaacc cactgaggct   120
gaactgcagg acatgatcaa cgaggtcgac gccgacggct ccggaacgat agatttccct   180
gagttcctca caatgatgca agaaagatga aggacaccga ctcggaggag gagatcgaga   240
ggcgttccgc gtattcgaca aggatgcaac ggtttcattt cggcggccga gctcaggcac   300
gttatgacca accttggcga gaagcttacg gacgaggagg tagatgagat gattcgggag   360
gcagatattg ac                                                       372
```